US010667720B2

(12) United States Patent
Wong et al.

(10) Patent No.: US 10,667,720 B2
(45) Date of Patent: Jun. 2, 2020

(54) APPARATUS AND METHODS FOR FIBER INTEGRATION AND REGISTRATION

(71) Applicant: Auris Health, Inc., Redwood City, CA (US)

(72) Inventors: Serena H. Wong, Menlo Park, CA (US); Jason J. Hsu, San Jose, CA (US); Francis Macnamara, Mountain View, CA (US); Gene Reis, San Jose, CA (US); Randall L. Schlesinger, San Mateo, CA (US); Neal A. Tanner, Mountain View, CA (US)

(73) Assignee: Auris Health, Inc., Redwood, CA (US)

( * ) Notice: Subject to any disclaimer, the term of this patent is extended or adjusted under 35 U.S.C. 154(b) by 0 days.

(21) Appl. No.: 15/258,470

(22) Filed: Sep. 7, 2016

(65) Prior Publication Data

US 2016/0374590 A1    Dec. 29, 2016

Related U.S. Application Data

(63) Continuation of application No. 14/860,291, filed on Sep. 21, 2015, now abandoned, which is a
(Continued)

(51) Int. Cl.
*G02B 6/00* (2006.01)
*G02B 6/38* (2006.01)
(Continued)

(52) U.S. Cl.
CPC .............. *A61B 5/065* (2013.01); *A61B 34/20* (2016.02); *G01B 11/24* (2013.01); *A61B 1/0051* (2013.01);
(Continued)

(58) Field of Classification Search
CPC ............ G02B 6/3887; G01D 5/35303; G01D 5/35383; A61B 5/06; A61B 5/0538
(Continued)

(56) References Cited

U.S. PATENT DOCUMENTS 3,572,325 A   3/1971   Bazell et al.
3,807,390 A   4/1974   Ostrowski et al.
(Continued)

FOREIGN PATENT DOCUMENTS

CA   2285342 A1   10/1998
CN   101500470   8/2009
(Continued)

OTHER PUBLICATIONS

"Fiber Optic Interferometer Fabry-Perot," viewed on Dec. 9, 2010, http://physicsanimations.com/sensors/English/interf.htm (5 pages).
(Continued)

*Primary Examiner* — Kaveh C Kianni
*Assistant Examiner* — Hung Q Lam
(74) *Attorney, Agent, or Firm* — Knobbe, Martens, Olson & Bear, LLP

(57) ABSTRACT

Systems and methods for integrating and/or registering a shape sensing fiber in or to various instruments are described herein. Registration fixtures and registration techniques for matching the coordinate system of a fiber to the coordinate system of an elongate instrument or other device are provided. Various systems and methods for integrating a shape sensing fiber into an elongate instrument or other device are also described herein.

23 Claims, 22 Drawing Sheets

Related U.S. Application Data continuation of application No. 13/314,057, filed on Dec. 7, 2011, now Pat. No. 9,138,166.

(60) Provisional application No. 61/513,488, filed on Jul. 29, 2011.

(51) Int. Cl.
    *G02B 6/06*           (2006.01)
    *A61B 5/06*           (2006.01)
    *A61B 34/20*          (2016.01)
    *G01B 11/24*         (2006.01)
    *G01L 1/24*            (2006.01)
    *A61M 25/01*         (2006.01)
    *A61B 1/005*         (2006.01)
    *A61B 17/00*         (2006.01)

(52) U.S. Cl.
    CPC .............. *A61B 2017/00292* (2013.01); *A61B 2034/2061* (2016.02); *A61B 2562/12* (2013.01); *A61M 25/0147* (2013.01); *A61M 2025/0166* (2013.01); *G01L 1/242* (2013.01)

(58) Field of Classification Search
    USPC .............. 385/12, 13, 65, 66, 68, 83, 84, 117
    See application file for complete search history.

(56) References Cited

U.S. PATENT DOCUMENTS

| | | |
|---|---|---|
| 3,913,565 A | 10/1975 | Kawahara |
| 4,294,234 A | 10/1981 | Matsuo |
| 4,392,485 A | 7/1983 | Hiltebrandt |
| 4,443,698 A | 4/1984 | Schiffner |
| 4,607,619 A | 8/1986 | Seike et al. |
| 4,690,175 A | 9/1987 | Ouchi et al. |
| 4,706,656 A | 11/1987 | Kubota |
| 4,741,326 A | 5/1988 | Sidall et al. |
| 4,745,908 A | 5/1988 | Wardle |
| 4,748,969 A | 6/1988 | Wardle |
| 4,750,475 A | 6/1988 | Yoshihashi |
| 4,761,073 A | 8/1988 | Meltz et al. |
| 4,771,766 A | 9/1988 | Aoshiro |
| 4,846,791 A | 7/1989 | Hattler et al. |
| 4,869,238 A | 9/1989 | Opie et al. |
| 4,906,496 A | 3/1990 | Hosono et al. |
| 4,907,168 A | 3/1990 | Boggs |
| 4,945,305 A | 7/1990 | Blood |
| 4,960,410 A | 10/1990 | Pinchuk |
| 4,967,732 A | 11/1990 | Inoue |
| 4,996,419 A | 2/1991 | Morey |
| 5,003,982 A | 4/1991 | Halperin |
| 5,007,705 A | 4/1991 | Morey et al. |
| 5,050,585 A | 9/1991 | Takahashi |
| 5,066,133 A | 11/1991 | Brienza |
| 5,067,346 A | 11/1991 | Field |
| 5,078,714 A | 1/1992 | Katims |
| 5,083,549 A | 1/1992 | Cho et al. |
| 5,086,401 A | 2/1992 | Glassman et al. |
| 5,106,387 A * | 4/1992 | Kittrell .............. A61B 1/00096 600/477 |
| 5,108,800 A | 4/1992 | Koo |
| 5,118,931 A | 6/1992 | Udd et al. |
| 5,125,909 A | 6/1992 | Heimberger |
| 5,144,960 A | 9/1992 | Mehra et al. |
| 5,168,864 A | 12/1992 | Shockey |
| 5,217,002 A | 6/1993 | Katsurada |
| 5,251,611 A | 10/1993 | Zehel |
| 5,257,617 A | 11/1993 | Takahashi |
| 5,261,391 A | 11/1993 | Inoue |
| 5,267,339 A | 11/1993 | Yamauchi et al. |
| 5,287,861 A | 2/1994 | Wilk |
| 5,313,934 A | 5/1994 | Wiita et al. |
| 5,339,799 A | 8/1994 | Kami et al. |
| 5,341,807 A | 8/1994 | Nardella |
| 5,368,015 A | 11/1994 | Wilk |
| 5,380,995 A | 1/1995 | Udd et al. |
| 5,386,818 A | 2/1995 | Schneebaum |
| 5,394,875 A | 3/1995 | Lewis et al. |
| 5,397,443 A | 3/1995 | Michaels |
| 5,397,891 A | 3/1995 | Udd et al. |
| 5,398,691 A | 3/1995 | Martin et al. |
| 5,401,956 A | 3/1995 | Dunphy et al. |
| 5,408,409 A | 4/1995 | Glassman et al. |
| 5,433,215 A | 7/1995 | Athanasiou et al. |
| 5,447,529 A | 9/1995 | Marchlinski et al. |
| 5,448,988 A | 9/1995 | Watanabe |
| 5,469,857 A | 11/1995 | Laurent et al. |
| 5,477,856 A | 12/1995 | Lundquist |
| 5,478,330 A | 12/1995 | Imran et al. |
| 5,482,029 A | 1/1996 | Sekiguchi |
| 5,489,270 A | 2/1996 | van Erp |
| 5,492,131 A | 2/1996 | Galel |
| 5,507,725 A | 4/1996 | Savage et al. |
| 5,533,985 A | 7/1996 | Wang |
| 5,553,611 A | 9/1996 | Budd et al. |
| 5,558,091 A | 9/1996 | Acker et al. |
| 5,563,967 A | 10/1996 | Haake |
| 5,580,200 A | 12/1996 | Fullerton |
| 5,591,965 A | 1/1997 | Udd |
| 5,600,330 A | 2/1997 | Blood |
| 5,627,927 A | 5/1997 | Udd |
| 5,630,783 A | 5/1997 | Steinberg |
| 5,631,973 A | 5/1997 | Green |
| 5,636,255 A | 6/1997 | Ellis |
| 5,662,108 A | 9/1997 | Budd et al. |
| 5,673,704 A | 10/1997 | Marchlinski et al. |
| 5,676,673 A | 10/1997 | Ferre et al. |
| 5,681,296 A | 10/1997 | Ishida |
| 5,697,377 A | 12/1997 | Wittkampf |
| 5,704,534 A | 1/1998 | Huitema et al. |
| 5,713,946 A | 2/1998 | Ben-Haim |
| 5,720,775 A | 2/1998 | Lamard |
| 5,722,959 A | 3/1998 | Bierman |
| 5,729,129 A | 3/1998 | Acker |
| 5,738,096 A | 4/1998 | Ben-Haim |
| 5,741,429 A | 4/1998 | Donadio, III |
| 5,749,362 A | 5/1998 | Funda et al. |
| 5,749,889 A | 5/1998 | Bacich et al. |
| 5,754,741 A | 5/1998 | Wang et al. |
| 5,762,458 A | 6/1998 | Wang et al. |
| 5,784,542 A | 7/1998 | Ohm et al. |
| 5,798,521 A | 8/1998 | Froggatt |
| 5,799,055 A | 8/1998 | Peshkin et al. |
| 5,810,716 A | 9/1998 | Mukherjee et al. |
| 5,815,640 A | 9/1998 | Wang et al. |
| 5,825,982 A | 10/1998 | Wright et al. |
| 5,828,059 A | 10/1998 | Udd |
| 5,833,608 A | 11/1998 | Acker |
| 5,836,869 A | 11/1998 | Kudo et al. |
| 5,836,874 A | 11/1998 | Swanson et al. |
| 5,836,990 A | 11/1998 | Li |
| 5,843,076 A | 12/1998 | Webster, Jr. et al. |
| 5,845,646 A | 12/1998 | Lemelson |
| 5,873,817 A | 2/1999 | Kokish et al. |
| 5,873,822 A | 2/1999 | Ferre et al. |
| 5,876,325 A | 3/1999 | Mizuno et al. |
| 5,878,193 A | 3/1999 | Wang et al. |
| 5,879,287 A | 3/1999 | Yoshihashi |
| 5,882,347 A | 3/1999 | Mouris-Laan |
| 5,888,191 A | 3/1999 | Akiba |
| 5,891,095 A | 4/1999 | Eggers et al. |
| 5,902,239 A | 5/1999 | Buurman |
| 5,910,129 A | 6/1999 | Koblish et al. |
| 5,911,694 A | 6/1999 | Ikeda et al. |
| 5,917,978 A | 6/1999 | Rutterman |
| 5,920,319 A | 7/1999 | Vining et al. |
| 5,921,924 A | 7/1999 | Avitall |
| 5,935,079 A | 8/1999 | Swanson et al. |
| 5,938,586 A | 8/1999 | Wilk |
| 5,938,587 A | 8/1999 | Taylor et al. |
| 5,950,629 A | 9/1999 | Taylor et al. |
| 5,953,683 A | 9/1999 | Hansen et al. |

(56) References Cited

U.S. PATENT DOCUMENTS

| | | |
|---|---|---|
| 5,983,126 A | 11/1999 | Wittkampf |
| 6,004,271 A | 12/1999 | Moore |
| 6,012,494 A | 1/2000 | Balazs |
| 6,016,439 A | 1/2000 | Acker |
| 6,019,724 A | 2/2000 | Gronningsaeter et al. |
| 6,035,082 A | 3/2000 | Murphy et al. |
| 6,061,587 A | 5/2000 | Kucharczyk et al. |
| 6,063,022 A | 5/2000 | Ben-Haim |
| 6,063,082 A | 5/2000 | Devore et al. |
| 6,063,095 A | 5/2000 | Wang et al. |
| 6,068,604 A | 5/2000 | Krause et al. |
| 6,069,420 A | 5/2000 | Mizzi et al. |
| 6,080,181 A | 6/2000 | Jensen et al. |
| 6,083,170 A | 7/2000 | Ben-Haim |
| 6,096,004 A | 8/2000 | Meglan et al. |
| 6,106,511 A | 8/2000 | Jensen |
| 6,129,668 A | 10/2000 | Haynor et al. |
| 6,132,368 A | 10/2000 | Cooper |
| 6,143,013 A | 11/2000 | Samson et al. |
| 6,144,026 A | 11/2000 | Udd et al. |
| 6,157,853 A | 12/2000 | Blume et al. |
| 6,161,032 A | 12/2000 | Acker |
| 6,172,499 B1 | 1/2001 | Ashe |
| 6,176,178 B1 | 1/2001 | Schor et al. |
| 6,197,015 B1 | 3/2001 | Wilson |
| 6,198,974 B1 | 3/2001 | Webster, Jr. |
| 6,201,984 B1 | 3/2001 | Funda et al. |
| 6,203,493 B1 | 3/2001 | Ben-Haim |
| 6,215,943 B1 | 4/2001 | Crotts et al. |
| 6,226,543 B1 | 5/2001 | Gilboa et al. |
| 6,228,028 B1 | 5/2001 | Klein et al. |
| 6,233,476 B1 | 5/2001 | Strommer et al. |
| 6,233,491 B1 | 5/2001 | Kordis et al. |
| 6,233,504 B1 | 5/2001 | Das et al. |
| 6,234,958 B1 | 5/2001 | Snoke et al. |
| 6,246,200 B1 | 6/2001 | Blumenkranz et al. |
| 6,253,770 B1 | 7/2001 | Acker et al. |
| 6,256,090 B1 | 7/2001 | Chen et al. |
| 6,266,551 B1 | 7/2001 | Osadchy et al. |
| 6,272,371 B1 | 8/2001 | Shlomo |
| 6,275,511 B1 | 8/2001 | Pan et al. |
| 6,275,628 B1 | 8/2001 | Jones et al. |
| 6,301,420 B1 | 10/2001 | Greenaway et al. |
| 6,301,496 B1 | 10/2001 | Reisfeld |
| 6,309,397 B1 | 10/2001 | Julian et al. |
| 6,310,828 B1 | 10/2001 | Mumm et al. |
| 6,312,435 B1 | 11/2001 | Wallace et al. |
| 6,315,715 B1 | 11/2001 | Taylor et al. |
| 6,331,181 B1 | 12/2001 | Tierney et al. |
| 6,364,888 B1 | 4/2002 | Niemeyer et al. |
| 6,366,722 B1 | 4/2002 | Murphy et al. |
| 6,370,411 B1 | 4/2002 | Osadchy et al. |
| 6,371,952 B1 | 4/2002 | Madhani et al. |
| 6,375,471 B1 | 4/2002 | Wendlandt et al. |
| 6,380,732 B1 | 4/2002 | Gilboa |
| 6,384,483 B1 | 5/2002 | Igarashi et al. |
| 6,389,187 B1 | 5/2002 | Greenaway et al. |
| 6,393,340 B2 | 5/2002 | Funda et al. |
| 6,398,731 B1 | 6/2002 | Mumm et al. |
| 6,400,979 B1 | 6/2002 | Stoianovici et al. |
| 6,404,497 B1 * | 6/2002 | Backman ............ A61B 5/0084 356/369 |
| 6,404,956 B1 | 6/2002 | Brennan, III et al. |
| 6,415,171 B1 | 7/2002 | Gueziec et al. |
| 6,424,885 B1 | 7/2002 | Niemeyer et al. |
| 6,426,796 B1 | 7/2002 | Pulliam et al. |
| 6,436,107 B1 | 8/2002 | Wang et al. |
| 6,464,632 B1 | 10/2002 | Taylor |
| 6,470,205 B2 | 10/2002 | Bosselmann et al. |
| 6,471,710 B1 | 10/2002 | Bucholtz |
| 6,485,411 B1 | 11/2002 | Konstorum |
| 6,491,626 B1 | 12/2002 | Stone et al. |
| 6,491,701 B2 | 12/2002 | Tierney et al. |
| 6,493,573 B1 | 12/2002 | Martinelli et al. |
| 6,493,608 B1 | 12/2002 | Niemeyer |
| 6,530,913 B1 | 3/2003 | Giba et al. |
| 6,537,205 B1 | 3/2003 | Smith |
| 6,544,230 B1 | 4/2003 | Flaherty et al. |
| 6,545,760 B1 | 4/2003 | Froggatt et al. |
| 6,550,342 B2 | 4/2003 | Croteau et al. |
| 6,551,273 B1 | 4/2003 | Olson et al. |
| 6,554,793 B1 | 4/2003 | Pauker et al. |
| 6,563,107 B2 | 5/2003 | Danisch et al. |
| 6,565,554 B1 | 5/2003 | Niemeyer |
| 6,571,639 B1 | 6/2003 | May et al. |
| 6,574,355 B2 | 6/2003 | Green |
| 6,580,938 B1 | 6/2003 | Acker |
| 6,587,750 B2 | 7/2003 | Gerbi et al. |
| 6,592,520 B1 | 7/2003 | Peszynski |
| 6,593,884 B1 | 7/2003 | Gilboa et al. |
| 6,594,552 B1 | 7/2003 | Nowlin |
| 6,610,007 B2 | 8/2003 | Belson et al. |
| 6,611,700 B1 | 8/2003 | Vilsmeier et al. |
| 6,615,155 B2 | 9/2003 | Gilboa |
| 6,618,612 B1 | 9/2003 | Acker et al. |
| 6,620,173 B2 | 9/2003 | Gerbi et al. |
| 6,626,899 B2 | 9/2003 | Houser et al. |
| 6,626,902 B1 | 9/2003 | Kucharczyk et al. |
| 6,659,939 B2 | 12/2003 | Moll et al. |
| 6,669,709 B1 | 12/2003 | Cohn et al. |
| 6,671,055 B1 | 12/2003 | Wavering et al. |
| 6,685,698 B2 | 2/2004 | Morley et al. |
| 6,697,664 B2 | 2/2004 | Kienzle, III et al. |
| 6,699,235 B2 | 3/2004 | Wallace et al. |
| 6,711,429 B1 | 3/2004 | Gilboa et al. |
| 6,716,166 B2 | 4/2004 | Govari |
| 6,716,178 B1 | 4/2004 | Kilpatrick et al. |
| 6,726,675 B1 | 4/2004 | Beyar |
| 6,726,699 B1 | 4/2004 | Wright et al. |
| 6,741,883 B2 | 5/2004 | Gildenberg |
| 6,746,422 B1 | 6/2004 | Noriega |
| 6,749,560 B1 | 6/2004 | Konstorum |
| 6,774,624 B2 | 8/2004 | Anderson et al. |
| 6,782,287 B2 | 8/2004 | Grzeszczuk et al. |
| 6,783,524 B2 | 8/2004 | Anderson et al. |
| 6,790,173 B2 | 9/2004 | Saadat |
| 6,796,963 B2 | 9/2004 | Carpenter et al. |
| 6,799,065 B1 | 9/2004 | Niemeyer |
| 6,817,973 B2 | 11/2004 | Merril et al. |
| 6,817,974 B2 | 11/2004 | Cooper et al. |
| 6,817,981 B2 | 11/2004 | Luce |
| 6,826,343 B2 | 11/2004 | Davis et al. |
| 6,827,710 B1 | 12/2004 | Mooney et al. |
| 6,827,712 B2 | 12/2004 | Tovey et al. |
| 6,837,846 B2 | 1/2005 | Jaffe |
| 6,850,817 B1 | 2/2005 | Green |
| 6,852,107 B2 | 2/2005 | Wang et al. |
| 6,858,003 B2 | 2/2005 | Evans et al. |
| 6,868,195 B2 | 3/2005 | Fujita |
| 6,876,786 B2 | 4/2005 | Chliaguine et al. |
| 6,888,623 B2 | 5/2005 | Clements |
| 6,892,090 B2 | 5/2005 | Verard et al. |
| 6,898,337 B2 | 5/2005 | Averett et al. |
| 6,905,460 B2 | 6/2005 | Wang et al. |
| 6,908,428 B2 | 6/2005 | Aizenfeld |
| 6,921,362 B2 | 7/2005 | Ouchi |
| 6,923,048 B2 | 8/2005 | Willsch et al. |
| 6,950,570 B1 | 9/2005 | Novotny |
| 6,958,035 B2 | 10/2005 | Friedman et al. |
| 6,963,792 B1 | 11/2005 | Green |
| 6,965,708 B2 | 11/2005 | Luo et al. |
| 6,974,455 B2 | 12/2005 | Garabedian et al. |
| 6,987,897 B2 | 1/2006 | Elster et al. |
| 6,994,094 B2 | 2/2006 | Schwartz |
| 6,996,430 B1 | 2/2006 | Gilboa et al. |
| 7,008,401 B2 | 3/2006 | Thompson et al. |
| 7,010,182 B2 | 3/2006 | Pennington |
| 7,021,173 B2 | 4/2006 | Stoianovici et al. |
| 7,038,190 B2 | 5/2006 | Udd et al. |
| 7,042,573 B2 | 5/2006 | Froggatt |
| 7,046,866 B2 | 5/2006 | Sahlgren et al. |
| 7,074,179 B2 | 7/2006 | Wang et al. |
| 7,087,049 B2 | 8/2006 | Nowlin et al. |
| 7,130,700 B2 | 10/2006 | Gardeski et al. |

(56) References Cited

U.S. PATENT DOCUMENTS

| | | |
|---|---|---|
| 7,154,081 B1 | 12/2006 | Friedersdorf et al. |
| 7,169,141 B2 | 1/2007 | Brock et al. |
| 7,225,012 B1 | 5/2007 | Susil et al. |
| 7,280,863 B2 | 10/2007 | Shachar |
| 7,297,142 B2 | 11/2007 | Brock |
| 7,320,700 B2 | 1/2008 | Cooper et al. |
| 7,330,245 B2 | 2/2008 | Froggatt |
| 7,331,967 B2 | 2/2008 | Lee et al. |
| 7,343,195 B2 | 3/2008 | Strommer et al. |
| 7,371,210 B2 | 5/2008 | Brock et al. |
| 7,404,824 B1 | 7/2008 | Webler et al. |
| 7,494,494 B2 | 2/2009 | Stoianovici et al. |
| 7,538,883 B2 | 5/2009 | Froggatt |
| 7,540,866 B2 | 6/2009 | Viswanathan et al. |
| 7,561,276 B2 | 7/2009 | Boyd |
| 7,562,660 B2 | 7/2009 | Saadat |
| 7,594,903 B2 | 9/2009 | Webler et al. |
| 7,645,230 B2 | 1/2010 | Mikkaichi |
| 7,645,231 B2 | 1/2010 | Akiba |
| 7,742,805 B2 | 6/2010 | Furnish et al. |
| 7,772,541 B2 | 8/2010 | Froggatt et al. |
| 7,781,724 B2 | 8/2010 | Childers et al. |
| 7,789,827 B2 | 9/2010 | Landry |
| 7,789,875 B2 | 9/2010 | Brock et al. |
| 7,850,642 B2 | 12/2010 | Moll et al. |
| 7,922,693 B2 | 4/2011 | Reis |
| 7,930,065 B2 | 4/2011 | Larkin et al. |
| 7,947,050 B2 | 5/2011 | Lee et al. |
| 7,947,051 B2 | 5/2011 | Lee et al. |
| 7,963,288 B2 | 6/2011 | Rosenberg et al. |
| 7,972,298 B2 | 7/2011 | Wallace et al. |
| 8,050,523 B2 | 11/2011 | Younge et al. |
| 8,052,621 B2 | 11/2011 | Wallace et al. |
| 8,052,636 B2 | 11/2011 | Moll et al. |
| 8,083,691 B2 | 11/2011 | Goldenberg et al. |
| 8,092,397 B2 | 1/2012 | Wallace et al. |
| 8,190,238 B2 | 5/2012 | Moll et al. |
| 8,219,178 B2 | 7/2012 | Smith et al. |
| 8,246,536 B2 | 8/2012 | Ochi |
| 8,290,571 B2 | 10/2012 | Younge et al. |
| 8,317,746 B2 | 11/2012 | Sewell et al. |
| 8,333,204 B2 | 12/2012 | Saadat |
| 8,372,019 B2 | 2/2013 | Goldenberg et al. |
| 8,377,077 B2 | 2/2013 | Reis |
| 8,388,556 B2 | 3/2013 | Wallace et al. |
| 8,391,957 B2 | 3/2013 | Carlson et al. |
| 8,409,234 B2 | 4/2013 | Stahler et al. |
| 8,444,637 B2 | 5/2013 | Podmore et al. |
| 8,460,236 B2 | 6/2013 | Roelle et al. |
| 8,498,691 B2 | 7/2013 | Moll et al. |
| 8,515,215 B2 | 8/2013 | Younge et al. |
| 8,523,883 B2 | 9/2013 | Saadat |
| 8,602,031 B2 | 12/2013 | Reis et al. |
| 8,657,781 B2 | 2/2014 | Sewell et al. |
| 8,672,837 B2 | 3/2014 | Roelle et al. |
| 8,705,903 B2 | 4/2014 | Younge et al. |
| 8,720,448 B2 | 5/2014 | Reis et al. |
| 8,758,231 B2 | 6/2014 | Bunch et al. |
| 8,780,339 B2 | 7/2014 | Udd |
| 8,811,777 B2 | 8/2014 | Younge et al. |
| 8,818,143 B2 | 8/2014 | Younge et al. |
| 8,821,376 B2 | 9/2014 | Tolkowsky |
| 8,827,947 B2 | 9/2014 | Bosman et al. |
| 8,827,948 B2 | 9/2014 | Romo et al. |
| 8,864,655 B2 | 10/2014 | Ramamurthy et al. |
| 8,894,589 B2 | 11/2014 | Leo et al. |
| 8,894,610 B2 | 11/2014 | MacNamara et al. |
| 8,961,533 B2 | 2/2015 | Stahler et al. |
| 8,989,528 B2 | 3/2015 | Udd |
| 9,014,851 B2 | 4/2015 | Wong et al. |
| 9,057,600 B2 | 6/2015 | Walker et al. |
| 9,066,740 B2 | 6/2015 | Carlson et al. |
| 9,138,166 B2 | 9/2015 | Wong et al. |
| 9,173,713 B2 | 11/2015 | Hart et al. |
| 9,186,046 B2 | 11/2015 | Ramamurthy et al. |
| 9,186,047 B2 | 11/2015 | Ramamurthy et al. |
| 9,204,933 B2 | 12/2015 | Reis et al. |
| 9,254,123 B2 | 2/2016 | Alvarez et al. |
| 9,271,663 B2 | 3/2016 | Walker et al. |
| 9,289,578 B2 | 3/2016 | Walker et al. |
| 9,314,306 B2 | 4/2016 | Yu |
| 9,358,076 B2 | 6/2016 | Moll et al. |
| 9,404,734 B2 | 8/2016 | Ramamurthy et al. |
| 9,408,669 B2 | 8/2016 | Kokish et al. |
| 9,427,551 B2 | 8/2016 | Leeflang et al. |
| 9,441,954 B2 | 9/2016 | Ramamurthy et al. |
| 9,452,018 B2 | 9/2016 | Yu |
| 9,480,820 B2 | 11/2016 | Goldenberg et al. |
| 9,498,291 B2 | 11/2016 | Balaji et al. |
| 9,498,601 B2 | 11/2016 | Tanner et al. |
| 9,500,472 B2 | 11/2016 | Ramamurthy et al. |
| 9,500,473 B2 | 11/2016 | Ramamurthy et al. |
| 9,504,604 B2 | 11/2016 | Alvarez |
| 9,532,840 B2 | 1/2017 | Wong et al. |
| 9,561,083 B2 | 2/2017 | Yu et al. |
| 9,566,414 B2 | 2/2017 | Wong et al. |
| 9,591,990 B2 * | 3/2017 | Chen .................. A61B 5/06 |
| 9,622,827 B2 | 4/2017 | Yu et al. |
| 9,629,595 B2 | 4/2017 | Walker et al. |
| 9,636,184 B2 | 5/2017 | Lee et al. |
| 9,636,483 B2 | 5/2017 | Hart et al. |
| 9,710,921 B2 | 7/2017 | Wong et al. |
| 9,713,509 B2 | 7/2017 | Schuh et al. |
| 9,726,476 B2 | 8/2017 | Ramamurthy et al. |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,818,681 B2 | 11/2017 | Machida |
| 9,827,061 B2 | 11/2017 | Balaji et al. |
| 9,844,353 B2 | 12/2017 | Walker et al. |
| 9,844,412 B2 | 12/2017 | Bogusky et al. |
| 9,867,635 B2 | 1/2018 | Alvarez et al. |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 10,016,900 B1 | 7/2018 | Meyer et al. |
| 10,022,192 B1 | 7/2018 | Ummalaneni |
| 10,046,140 B2 | 8/2018 | Kokish et al. |
| 10,123,755 B2 | 11/2018 | Walker et al. |
| 10,130,427 B2 | 11/2018 | Tanner et al. |
| 10,145,747 B1 | 12/2018 | Lin et al. |
| 10,159,532 B1 | 12/2018 | Ummalaneni et al. |
| 2001/0004676 A1 | 6/2001 | Ouchi |
| 2001/0009976 A1 | 7/2001 | Panescu et al. |
| 2001/0021843 A1 | 9/2001 | Bosselmann et al. |
| 2001/0029366 A1 | 10/2001 | Swanson et al. |
| 2002/0064330 A1 | 5/2002 | Croteau et al. |
| 2002/0087169 A1 | 7/2002 | Brock et al. |
| 2002/0138009 A1 | 9/2002 | Brockway et al. |
| 2002/0156369 A1 | 10/2002 | Chakeres |
| 2002/0166955 A1 | 11/2002 | Ogawa |
| 2002/0177789 A1 | 11/2002 | Ferry et al. |
| 2003/0016898 A1 | 1/2003 | Baruch et al. |
| 2003/0050649 A1 | 3/2003 | Brock et al. |
| 2003/0055360 A1 | 3/2003 | Zeleznik et al. |
| 2003/0073908 A1 | 4/2003 | Desai |
| 2003/0074011 A1 | 4/2003 | Gilboa et al. |
| 2003/0109780 A1 | 6/2003 | Goste-Maniere et al. |
| 2003/0130564 A1 | 7/2003 | Martone et al. |
| 2003/0135204 A1 | 7/2003 | Lee et al. |
| 2003/0158545 A1 | 8/2003 | Hovda et al. |
| 2003/0163199 A1 | 8/2003 | Chu et al. |
| 2003/0188585 A1 | 10/2003 | Esser et al. |
| 2003/0195502 A1 | 10/2003 | Garabedian et al. |
| 2003/0195664 A1 | 10/2003 | Nowlin et al. |
| 2004/0015122 A1 | 1/2004 | Zhang et al. |
| 2004/0034282 A1 | 2/2004 | Quaid, III |

(56) References Cited

U.S. PATENT DOCUMENTS

| | | |
|---|---|---|
| 2004/0034300 A1 | 2/2004 | Verard et al. |
| 2004/0034365 A1 | 2/2004 | Lentz et al. |
| 2004/0054322 A1 | 3/2004 | Vargas |
| 2004/0138525 A1 | 7/2004 | Saadat et al. |
| 2004/0152972 A1 | 8/2004 | Hunter |
| 2004/0165810 A1 | 8/2004 | Fujita |
| 2004/0171929 A1 | 9/2004 | Leitner et al. |
| 2004/0176751 A1 | 9/2004 | Weitzner et al. |
| 2004/0193013 A1 | 9/2004 | Isakawa et al. |
| 2004/0193146 A1 | 9/2004 | Lee et al. |
| 2004/0208413 A1 | 10/2004 | Scandale et al. |
| 2004/0220588 A1 | 11/2004 | Kermode et al. |
| 2004/0249246 A1 | 12/2004 | Campos |
| 2005/0004515 A1 | 1/2005 | Hart et al. |
| 2005/0027397 A1 | 2/2005 | Niemeyer |
| 2005/0033149 A1 | 2/2005 | Strommer et al. |
| 2005/0036140 A1 | 2/2005 | Elster et al. |
| 2005/0054934 A1 | 3/2005 | Furnish et al. |
| 2005/0059960 A1 | 3/2005 | Simaan et al. |
| 2005/0085728 A1 | 4/2005 | Fukuda |
| 2005/0125005 A1 | 6/2005 | Fujikura |
| 2005/0131460 A1 | 6/2005 | Gifford, III et al. |
| 2005/0137478 A1 | 6/2005 | Younge et al. |
| 2005/0154262 A1 | 7/2005 | Banik et al. |
| 2005/0159646 A1 | 7/2005 | Nordstrom et al. |
| 2005/0159789 A1 | 7/2005 | Brockway et al. |
| 2005/0165276 A1 | 7/2005 | Belson et al. |
| 2005/0171508 A1 | 8/2005 | Gilboa |
| 2005/0182295 A1 | 8/2005 | Soper et al. |
| 2005/0182330 A1 | 8/2005 | Brockway et al. |
| 2005/0197530 A1 | 9/2005 | Wallace et al. |
| 2005/0200324 A1 | 9/2005 | Guthart et al. |
| 2005/0201664 A1 | 9/2005 | Udd et al. |
| 2005/0203382 A1 | 9/2005 | Govari et al. |
| 2005/0222554 A1 | 10/2005 | Wallace et al. |
| 2005/0222581 A1 | 10/2005 | Fischer et al. |
| 2005/0254575 A1 | 11/2005 | Hannuksela et al. |
| 2005/0272975 A1 | 12/2005 | McWeeney et al. |
| 2005/0288549 A1 | 12/2005 | Mathis |
| 2006/0013523 A1 | 1/2006 | Childers et al. |
| 2006/0025679 A1 | 2/2006 | Viswanathan et al. |
| 2006/0036164 A1 | 2/2006 | Wilson et al. |
| 2006/0036213 A1 | 2/2006 | Viswanathan et al. |
| 2006/0041188 A1 | 2/2006 | Dirusso et al. |
| 2006/0057560 A1 | 3/2006 | Hlavka et al. |
| 2006/0058647 A1 | 3/2006 | Strommer et al. |
| 2006/0076023 A1 | 4/2006 | Rapacki et al. |
| 2006/0084945 A1 | 4/2006 | Moll et al. |
| 2006/0095022 A1 | 5/2006 | Moll et al. |
| 2006/0100610 A1 | 5/2006 | Wallace et al. |
| 2006/0111692 A1 | 5/2006 | Hlavka et al. |
| 2006/0142897 A1 | 6/2006 | Green |
| 2006/0161045 A1 | 7/2006 | Merril et al. |
| 2006/0178556 A1 | 8/2006 | Hasser et al. |
| 2006/0184016 A1 | 8/2006 | Glossop |
| 2006/0200026 A1 | 9/2006 | Wallace et al. |
| 2006/0200049 A1 | 9/2006 | Leo et al. |
| 2006/0253108 A1 | 11/2006 | Yu et al. |
| 2006/0264708 A1 | 11/2006 | Horne |
| 2006/0271036 A1 | 11/2006 | Garabedian et al. |
| 2006/0276775 A1 | 12/2006 | Rosenberg et al. |
| 2006/0276827 A1 | 12/2006 | Mitelberg et al. |
| 2006/0293864 A1 | 12/2006 | Soss |
| 2007/0015997 A1 | 1/2007 | Higgins et al. |
| 2007/0038181 A1 | 2/2007 | Melamud et al. |
| 2007/0043338 A1 | 2/2007 | Moll et al. |
| 2007/0055128 A1 | 3/2007 | Glossop |
| 2007/0060847 A1 | 3/2007 | Leo et al. |
| 2007/0060879 A1 | 3/2007 | Weitzner et al. |
| 2007/0065077 A1 | 3/2007 | Childers et al. |
| 2007/0112355 A1 | 5/2007 | Salahieh |
| 2007/0123851 A1 | 5/2007 | Alejandro et al. |
| 2007/0135733 A1 | 6/2007 | Soukup et al. |
| 2007/0135763 A1 | 6/2007 | Musbach et al. |
| 2007/0135803 A1 | 6/2007 | Belson |
| 2007/0156019 A1 | 7/2007 | Larkin et al. |
| 2007/0156123 A1 | 7/2007 | Moll et al. |
| 2007/0161857 A1 | 7/2007 | Durant et al. |
| 2007/0197896 A1 | 8/2007 | Moll et al. |
| 2007/0197939 A1 | 8/2007 | Wallace et al. |
| 2007/0201793 A1 | 8/2007 | Askins et al. |
| 2007/0225559 A1 | 9/2007 | Clerc et al. |
| 2007/0233044 A1 | 10/2007 | Wallace et al. |
| 2007/0249901 A1 | 10/2007 | Ohline et al. |
| 2007/0265503 A1 | 11/2007 | Schlesinger et al. |
| 2007/0270645 A1 | 11/2007 | Ikeda |
| 2007/0270679 A1 | 11/2007 | Nguyen et al. |
| 2007/0276180 A1 | 11/2007 | Greenburg et al. |
| 2007/0282167 A1 | 12/2007 | Barenboym et al. |
| 2007/0287886 A1 | 12/2007 | Saadat |
| 2007/0287999 A1 | 12/2007 | Malecki et al. |
| 2007/0293721 A1 | 12/2007 | Gilboa |
| 2007/0293724 A1 | 12/2007 | Saadat et al. |
| 2007/0299434 A1 | 12/2007 | Malecki et al. |
| 2008/0009750 A1 | 1/2008 | Aeby et al. |
| 2008/0015445 A1 | 1/2008 | Saadat et al. |
| 2008/0039255 A1 | 2/2008 | Jinno et al. |
| 2008/0051629 A1 | 2/2008 | Sugiyama et al. |
| 2008/0058836 A1 | 3/2008 | Moll et al. |
| 2008/0065103 A1 | 3/2008 | Cooper et al. |
| 2008/0097293 A1 | 4/2008 | Chin et al. |
| 2008/0108869 A1 | 5/2008 | Sanders et al. |
| 2008/0139887 A1 | 6/2008 | Fitpatrick |
| 2008/0146874 A1 | 6/2008 | Miller |
| 2008/0177285 A1 | 7/2008 | Brock et al. |
| 2008/0183071 A1 | 7/2008 | Strommer et al. |
| 2008/0208001 A1 | 8/2008 | Hadani |
| 2008/0212082 A1 | 9/2008 | Froggatt et al. |
| 2008/0218770 A1* | 9/2008 | Moll .................. A61G 7/0503 356/614 |
| 2008/0234631 A1 | 9/2008 | Reis |
| 2008/0243064 A1 | 10/2008 | Stahler et al. |
| 2008/0249536 A1 | 10/2008 | Stahler et al. |
| 2008/0262480 A1 | 10/2008 | Stahler et al. |
| 2008/0262513 A1 | 10/2008 | Stahler et al. |
| 2008/0285909 A1 | 11/2008 | Younge et al. |
| 2008/0300592 A1 | 12/2008 | Weitzner et al. |
| 2008/0319311 A1 | 12/2008 | Hamadeh |
| 2009/0024195 A1 | 1/2009 | Rezai et al. |
| 2009/0054884 A1 | 2/2009 | Farley et al. |
| 2009/0076476 A1 | 3/2009 | Barbagli et al. |
| 2009/0082660 A1 | 3/2009 | Rahn et al. |
| 2009/0099420 A1 | 4/2009 | Woodley et al. |
| 2009/0123111 A1 | 5/2009 | Udd |
| 2009/0137952 A1* | 5/2009 | Ramamurthy .......... A61B 5/06 604/95.01 |
| 2009/0138025 A1 | 5/2009 | Stahler et al. |
| 2009/0163851 A1 | 6/2009 | Holloway |
| 2009/0201503 A1 | 8/2009 | Bennion et al. |
| 2009/0221908 A1 | 9/2009 | Glossop |
| 2009/0227997 A1 | 9/2009 | Wang et al. |
| 2009/0247880 A1 | 10/2009 | Naruse et al. |
| 2009/0254083 A1 | 10/2009 | Wallace et al. |
| 2009/0262109 A1 | 10/2009 | Markowitz et al. |
| 2009/0306587 A1 | 12/2009 | Milijasevic et al. |
| 2009/0312756 A1 | 12/2009 | Schlesinger et al. |
| 2009/0318797 A1 | 12/2009 | Hadani |
| 2009/0320527 A1 | 12/2009 | Harper et al. |
| 2009/0324161 A1 | 12/2009 | Prisco |
| 2010/0030023 A1 | 2/2010 | Yoshie |
| 2010/0073150 A1 | 3/2010 | Olson et al. |
| 2010/0081920 A1 | 4/2010 | Whitmore, III et al. |
| 2010/0106140 A1 | 4/2010 | Odland et al. |
| 2010/0114115 A1 | 5/2010 | Schlesinger et al. |
| 2010/0121138 A1 | 5/2010 | Goldenberg et al. |
| 2010/0121269 A1 | 5/2010 | Goldenberg |
| 2010/0125284 A1 | 5/2010 | Tanner et al. |
| 2010/0130823 A1 | 5/2010 | Ando |
| 2010/0175701 A1 | 7/2010 | Reis et al. |
| 2010/0179632 A1 | 7/2010 | Bruszewski et al. |
| 2010/0217184 A1 | 8/2010 | Koblish et al. |
| 2010/0228191 A1 | 9/2010 | Alvarez et al. |
| 2010/0249506 A1 | 9/2010 | Prisco et al. |
| 2010/0280320 A1 | 11/2010 | Alvarez et al. |

(56) References Cited

U.S. PATENT DOCUMENTS

| | | |
|---|---|---|
| 2010/0280525 A1 | 11/2010 | Alvarez et al. |
| 2010/0312096 A1 | 12/2010 | Guttman et al. |
| 2010/0331856 A1 | 12/2010 | Carlson et al. |
| 2011/0009863 A1 | 1/2011 | Stanislaw |
| 2011/0046441 A1 | 2/2011 | Wiltshire et al. |
| 2011/0077681 A1 | 3/2011 | Nagano |
| 2011/0090486 A1 | 4/2011 | Udd |
| 2011/0098533 A1* | 4/2011 | Onoda .................. A61B 1/0051 600/117 |
| 2011/0130718 A1 | 6/2011 | Kidd et al. |
| 2011/0148442 A1 | 6/2011 | Berner |
| 2011/0152880 A1 | 6/2011 | Alvarez et al. |
| 2011/0152883 A1 | 6/2011 | Reis |
| 2011/0172680 A1 | 7/2011 | Younge et al. |
| 2011/0200171 A1 | 8/2011 | Bettel et al. |
| 2011/0261183 A1 | 10/2011 | Ma et al. |
| 2011/0295247 A1 | 12/2011 | Schlesinger et al. |
| 2011/0295248 A1 | 12/2011 | Wallace et al. |
| 2011/0295267 A1 | 12/2011 | Tanner et al. |
| 2011/0295268 A1 | 12/2011 | Roelle et al. |
| 2011/0301662 A1 | 12/2011 | Bar-Yoseph et al. |
| 2011/0306836 A1 | 12/2011 | Ohline et al. |
| 2011/0319815 A1 | 12/2011 | Roelle et al. |
| 2011/0319910 A1 | 12/2011 | Roelle et al. |
| 2012/0071894 A1 | 3/2012 | Tanner et al. |
| 2012/0071895 A1 | 3/2012 | Stahler et al. |
| 2012/0089047 A1 | 4/2012 | Ryba et al. |
| 2012/0116253 A1 | 5/2012 | Wallace et al. |
| 2012/0123327 A1 | 5/2012 | Miller |
| 2012/0136419 A1 | 5/2012 | Zarembo et al. |
| 2012/0143226 A1 | 6/2012 | Belson et al. |
| 2012/0190976 A1 | 7/2012 | Kleinstreuer |
| 2012/0191079 A1 | 7/2012 | Moll et al. |
| 2012/0191083 A1 | 7/2012 | Moll et al. |
| 2012/0191086 A1 | 7/2012 | Moll et al. |
| 2012/0191107 A1 | 7/2012 | Tanner et al. |
| 2012/0239012 A1 | 9/2012 | Laurent et al. |
| 2012/0259244 A1 | 10/2012 | Roberts et al. |
| 2012/0281205 A1 | 11/2012 | Askins |
| 2012/0283747 A1 | 11/2012 | Popovic |
| 2013/0018400 A1 | 1/2013 | Milton et al. |
| 2013/0028554 A1 | 1/2013 | Wong et al. |
| 2013/0030363 A1 | 1/2013 | Wong et al. |
| 2013/0030519 A1 | 1/2013 | Tran et al. |
| 2013/0035537 A1 | 2/2013 | Wallace et al. |
| 2013/0085330 A1 | 4/2013 | Ramamurthy et al. |
| 2013/0085331 A1 | 4/2013 | Ramamurthy et al. |
| 2013/0085333 A1 | 4/2013 | Ramamurthy et al. |
| 2013/0090528 A1 | 4/2013 | Ramamurthy et al. |
| 2013/0090530 A1 | 4/2013 | Ramamurthy |
| 2013/0090552 A1* | 4/2013 | Ramamurthy ........... A61B 5/06 600/424 |
| 2013/0109957 A1 | 5/2013 | Hooft et al. |
| 2013/0144116 A1 | 6/2013 | Cooper et al. |
| 2013/0158477 A1 | 6/2013 | Goldenberg et al. |
| 2013/0165854 A1 | 6/2013 | Sandhu et al. |
| 2013/0165908 A1 | 6/2013 | Purdy et al. |
| 2013/0165945 A9 | 6/2013 | Roelle |
| 2013/0253534 A1 | 9/2013 | Reis |
| 2013/0317276 A1 | 11/2013 | D'Andrea |
| 2013/0317519 A1 | 11/2013 | Romo et al. |
| 2013/0345519 A1 | 12/2013 | Piskun et al. |
| 2014/0046313 A1 | 2/2014 | Pederson et al. |
| 2014/0069437 A1 | 3/2014 | Reis et al. |
| 2014/0142591 A1 | 5/2014 | Alvarez et al. |
| 2014/0200402 A1 | 7/2014 | Snoke et al. |
| 2014/0257334 A1 | 9/2014 | Wong et al. |
| 2014/0264081 A1 | 9/2014 | Walker et al. |
| 2014/0275985 A1 | 9/2014 | Walker et al. |
| 2014/0275988 A1 | 9/2014 | Walker et al. |
| 2014/0276391 A1 | 9/2014 | Yu |
| 2014/0276392 A1 | 9/2014 | Wong et al. |
| 2014/0276594 A1 | 9/2014 | Tanner et al. |
| 2014/0276646 A1 | 9/2014 | Wong et al. |
| 2014/0276934 A1 | 9/2014 | Balaji et al. |
| 2014/0276935 A1 | 9/2014 | Yu |
| 2014/0276936 A1 | 9/2014 | Kokish et al. |
| 2014/0276937 A1 | 9/2014 | Wong et al. |
| 2014/0276938 A1 | 9/2014 | Hsu et al. |
| 2014/0276939 A1 | 9/2014 | Kokish et al. |
| 2014/0309649 A1 | 10/2014 | Alvarez et al. |
| 2014/0316397 A1 | 10/2014 | Brown |
| 2014/0357953 A1 | 12/2014 | Roelle et al. |
| 2014/0357984 A1 | 12/2014 | Wallace et al. |
| 2014/0364870 A1 | 12/2014 | Alvarez et al. |
| 2014/0379000 A1 | 12/2014 | Romo et al. |
| 2015/0031950 A1 | 1/2015 | Drontle et al. |
| 2015/0051592 A1 | 2/2015 | Kintz |
| 2015/0101442 A1 | 4/2015 | Romo |
| 2015/0119637 A1 | 4/2015 | Alavarez et al. |
| 2015/0119638 A1 | 4/2015 | Yu et al. |
| 2015/0142013 A1 | 5/2015 | Tanner et al. |
| 2015/0164594 A1 | 6/2015 | Romo et al. |
| 2015/0164595 A1 | 6/2015 | Bogusky et al. |
| 2015/0164596 A1 | 6/2015 | Romo et al. |
| 2015/0193946 A1 | 7/2015 | Wong et al. |
| 2015/0209112 A1 | 7/2015 | Moll et al. |
| 2015/0265807 A1 | 9/2015 | Park et al. |
| 2015/0327939 A1 | 11/2015 | Kokish et al. |
| 2015/0335480 A1 | 11/2015 | Alvarez et al. |
| 2016/0001038 A1 | 1/2016 | Romo et al. |
| 2016/0007881 A1 | 1/2016 | Wong et al. |
| 2016/0067009 A1 | 3/2016 | Ramamurthy et al. |
| 2016/0067450 A1 | 3/2016 | Kowshik |
| 2016/0151122 A1 | 6/2016 | Alvarez et al. |
| 2016/0184032 A1 | 6/2016 | Romo et al. |
| 2016/0202053 A1 | 7/2016 | Walker et al. |
| 2016/0213884 A1 | 7/2016 | Park |
| 2016/0227982 A1 | 8/2016 | Takahashi |
| 2016/0228032 A1 | 8/2016 | Walker et al. |
| 2016/0235495 A1 | 8/2016 | Wallace et al. |
| 2016/0270865 A1 | 9/2016 | Landey et al. |
| 2016/0279394 A1 | 9/2016 | Moll et al. |
| 2016/0287279 A1 | 10/2016 | Bovay et al. |
| 2016/0287346 A1 | 10/2016 | Hyodo et al. |
| 2016/0296294 A1 | 10/2016 | Moll et al. |
| 2016/0338785 A1 | 11/2016 | Kokish et al. |
| 2016/0346049 A1 | 12/2016 | Allen et al. |
| 2016/0374541 A1 | 12/2016 | Agrawal et al. |
| 2016/0374590 A1 | 12/2016 | Wong et al. |
| 2017/0007337 A1 | 1/2017 | Dan |
| 2017/0007343 A1 | 1/2017 | Yu |
| 2017/0065356 A1 | 3/2017 | Balaji et al. |
| 2017/0071684 A1 | 3/2017 | Kokish et al. |
| 2017/0100084 A1 | 4/2017 | Walker et al. |
| 2017/0100199 A1 | 4/2017 | Yu et al. |
| 2017/0105803 A1 | 4/2017 | Wong et al. |
| 2017/0113019 A1 | 4/2017 | Wong et al. |
| 2017/0119411 A1 | 5/2017 | Shah |
| 2017/0119412 A1 | 5/2017 | Noonan et al. |
| 2017/0119413 A1 | 5/2017 | Romo |
| 2017/0119481 A1 | 5/2017 | Romo et al. |
| 2017/0119484 A1 | 5/2017 | Tanner et al. |
| 2017/0151027 A1 | 6/2017 | Walker et al. |
| 2017/0165011 A1 | 6/2017 | Bovay et al. |
| 2017/0172673 A1 | 6/2017 | Yu et al. |
| 2017/0172680 A1 | 6/2017 | Bowling |
| 2017/0202627 A1 | 7/2017 | Sramek et al. |
| 2017/0209073 A1 | 7/2017 | Sramek et al. |
| 2017/0209224 A1 | 7/2017 | Walker et al. |
| 2017/0209672 A1 | 7/2017 | Hart et al. |
| 2017/0290631 A1 | 10/2017 | Lee et al. |
| 2017/0333679 A1 | 11/2017 | Jiang |
| 2017/0340396 A1 | 11/2017 | Romo et al. |
| 2017/0360418 A1 | 12/2017 | Wong et al. |
| 2017/0365055 A1 | 12/2017 | Mintz et al. |
| 2017/0367782 A1 | 12/2017 | Schuh et al. |
| 2018/0025666 A1 | 1/2018 | Ho et al. |
| 2018/0055589 A1 | 3/2018 | Joseph et al. |
| 2018/0056044 A1 | 3/2018 | Choi et al. |
| 2018/0177383 A1 | 6/2018 | Noonan et al. |
| 2018/0177556 A1 | 6/2018 | Noonan et al. |
| 2018/0177561 A1 | 6/2018 | Mintz et al. |
| 2018/0214011 A1 | 8/2018 | Graetzel et al. |

(56) References Cited

U.S. PATENT DOCUMENTS

| | | | |
|---|---|---|---|
| 2018/0221038 A1 | 8/2018 | Noonan et al. | |
| 2018/0221039 A1 | 8/2018 | Shah | |
| 2018/0250083 A1 | 9/2018 | Schuh et al. | |
| 2018/0271616 A1 | 9/2018 | Schuh et al. | |
| 2018/0279852 A1 | 10/2018 | Rafii-Tari et al. | |
| 2018/0280660 A1 | 10/2018 | Landey et al. | |
| 2018/0289243 A1 | 10/2018 | Landey et al. | |
| 2018/0289431 A1 | 10/2018 | Draper et al. | |
| 2018/0325499 A1 | 11/2018 | Landey et al. | |
| 2018/0326181 A1 | 11/2018 | Kokish et al. | |
| 2018/0333044 A1 | 11/2018 | Jenkins | |
| 2018/0360435 A1 | 12/2018 | Romo | |
| 2019/0000559 A1 | 1/2019 | Berman et al. | |
| 2019/0000560 A1 | 1/2019 | Berman et al. | |
| 2019/0000566 A1 | 1/2019 | Graetzel et al. | |
| 2019/0000568 A1 | 1/2019 | Connolly et al. | |
| 2019/0000576 A1 | 1/2019 | Mintz et al. | |
| 2019/0083183 A1 | 3/2019 | Moll et al. | |
| 2019/0105110 A1* | 4/2019 | Tanner | A61B 6/12 |
| 2019/0105776 A1 | 4/2019 | Ho et al. | |
| 2019/0105785 A1 | 4/2019 | Meyer | |
| 2019/0107454 A1 | 4/2019 | Lin | |
| 2019/0110839 A1 | 4/2019 | Rafii-Tari et al. | |
| 2019/0110843 A1 | 4/2019 | Ummalaneni et al. | |
| 2019/0151148 A1 | 4/2019 | Alvarez et al. | |
| 2019/0228528 A1 | 4/2019 | Mintz et al. | |
| 2019/0167366 A1 | 6/2019 | Ummalaneni | |
| 2019/0175009 A1 | 6/2019 | Mintz | |
| 2019/0175062 A1 | 6/2019 | Rafii-Tari et al. | |
| 2019/0175287 A1 | 6/2019 | Hill | |
| 2019/0175799 A1 | 6/2019 | Hsu | |
| 2019/0183585 A1 | 6/2019 | Rafii-Tari et al. | |
| 2019/0183587 A1 | 6/2019 | Rafii-Tari et al. | |
| 2019/0216548 A1 | 7/2019 | Ummalaneni | |
| 2019/0216550 A1 | 7/2019 | Eyre | |
| 2019/0216576 A1 | 7/2019 | Eyre | |
| 2019/0223974 A1 | 7/2019 | Romo | |
| 2019/0228525 A1 | 7/2019 | Mintz et al. | |
| 2019/0246882 A1 | 8/2019 | Graetzel et al. | |
| 2019/0262086 A1 | 8/2019 | Connolly et al. | |
| 2019/0269468 A1 | 9/2019 | Hsu et al. | |
| 2019/0274764 A1 | 9/2019 | Romo | |
| 2019/0290109 A1 | 9/2019 | Agrawal et al. | |
| 2019/0298160 A1 | 10/2019 | Ummalaneni et al. | |
| 2019/0298458 A1 | 10/2019 | Srinivasan | |
| 2019/0298460 A1 | 10/2019 | Al-Jadda | |
| 2019/0298465 A1 | 10/2019 | Chin | |
| 2019/0307987 A1 | 10/2019 | Yu | |
| 2019/0328213 A1 | 10/2019 | Landey et al. | |
| 2019/0336238 A1 | 11/2019 | Yu | |
| 2019/0365209 A1 | 12/2019 | Ye et al. | |
| 2019/0365479 A1 | 12/2019 | Rafii-Tari | |
| 2019/0365486 A1 | 12/2019 | Srinivasan et al. | |
| 2019/0374297 A1 | 12/2019 | Wallace et al. | |
| 2019/0375383 A1 | 12/2019 | Alvarez | |
| 2019/0380787 A1 | 12/2019 | Ye | |
| 2019/0380797 A1 | 12/2019 | Yu | |

FOREIGN PATENT DOCUMENTS

| | | |
|---|---|---|
| CN | 102665590 | 9/2012 |
| EP | 0 543 539 | 5/1993 |
| EP | 0 776 739 | 6/1997 |
| EP | 1103223 A2 | 5/2001 |
| EP | 1 442 720 | 8/2004 |
| EP | 0 904 796 | 11/2004 |
| JP | 2001296110 A | 8/1999 |
| JP | 2000292627 A | 10/2000 |
| JP | 2001013334 A | 1/2001 |
| JP | 2001201645 A | 7/2001 |
| JP | 2003185897 A | 7/2003 |
| JP | 2004180953 A | 7/2004 |
| JP | 2004251779 A | 9/2004 |
| JP | 2005010064 A | 1/2005 |
| JP | 3649666 | 5/2005 |
| JP | 2006-525087 | 11/2006 |
| JP | 2007-511247 | 5/2007 |
| JP | 2010-046384 | 3/2010 |
| JP | 2011-015992 | 1/2011 |
| JP | 2012-105793 | 6/2012 |
| WO | 9202276 A1 | 2/1992 |
| WO | WO 94/14494 | 7/1994 |
| WO | 9744089 A1 | 11/1997 |
| WO | 9808121 | 2/1998 |
| WO | 9945994 A1 | 9/1999 |
| WO | 0011495 A1 | 3/2000 |
| WO | 0045193 A1 | 8/2000 |
| WO | WO 00/67640 | 11/2000 |
| WO | 0133165 A1 | 5/2001 |
| WO | 0219898 A2 | 3/2002 |
| WO | 0247751 A2 | 6/2002 |
| WO | WO 02/074178 | 9/2002 |
| WO | 03065095 A2 | 8/2003 |
| WO | 03077769 A1 | 9/2003 |
| WO | 03091839 A2 | 11/2003 |
| WO | 2004001469 A1 | 12/2003 |
| WO | WO 04/039273 | 5/2004 |
| WO | WO 04/105849 | 12/2004 |
| WO | WO 05/032637 | 4/2005 |
| WO | 2005055605 A1 | 6/2005 |
| WO | 2005087128 A1 | 9/2005 |
| WO | WO 05/081202 | 9/2005 |
| WO | 2006092707 A1 | 9/2006 |
| WO | 2006099056 A2 | 9/2006 |
| WO | 2007015139 A2 | 2/2007 |
| WO | 2007045028 A1 | 4/2007 |
| WO | WO 09/097461 | 6/2007 |
| WO | 2007109778 A1 | 9/2007 |
| WO | WO 07/146987 | 12/2007 |
| WO | 2008094949 A2 | 8/2008 |
| WO | 2008097540 A2 | 8/2008 |
| WO | 2008131303 A2 | 10/2008 |
| WO | 2009094588 A2 | 7/2009 |
| WO | WO 09/092059 | 7/2009 |
| WO | WO 10/081187 | 7/2010 |
| WO | WO 10/088187 | 8/2010 |
| WO | WO 11/005335 | 1/2011 |
| WO | WO 13/107468 | 7/2013 |
| WO | WO 15/093602 | 12/2013 |
| WO | WO 16/003052 | 1/2016 |

OTHER PUBLICATIONS

Non-Final Rejection for U.S. Appl. No. 12/507,727, dated Dec. 22, 2010 (15 pages).
Prosecution File History for U.S. Pat. No. 8,048,063 (1,405 pages).
Papers from prosecution File History for U.S. Appl. No. 12/106,254 (57 pages).
Papers from prosecution File History for U.S. Appl. No. 11/690,116 (45 pages).
First Chinese Office Action for Chinese Patent Application No. 200780009956.6, dated Feb. 5, 2010 (20 pages).
Non-Final Office Action for U.S. Appl. No. 11/678,016, dated Aug. 31, 2010 (30 pages).
Luna Innovations, "Distributed Sensing System Sensor Array Specification," pp. 1-3, website, retrieved from www.lunainnovations.com.
European Search Report for European Application No. 12819991.6, dated Feb. 25, 2015 (7 pages).
Prosecution File History of U.S. Pat. No. 5,798,521 (69 pages).
Prosecution File History of U.S. Pat. No. 6,256,090 (126 pages).
Prosecution File History of U.S. Pat. No. 6,470,205 (64 pages).
Chinese Office Action for related Chinese Patent Application No. 200780006359.8, dated Aug. 9, 2010 (6 pages).
European Office Action from related European Patent Application No. 07757358.2, dated Dec. 9, 2008 (3 pages).
International Preliminary Report on Patentability for International Patent Application No. PCT/US2007/062617, dated Aug. 26, 2008 (7 pages).
International Search Report for International Patent Application PCT/US2006/026218, dated Dec. 12, 2006 (2 pages).

(56) References Cited

OTHER PUBLICATIONS

International Search Report for International Patent Application No. PCT/US2005/007108, dated Jun. 27, 2005 (4 pages).
International Search Report and Written Opinion for International Patent Application No. PCT/US2008/082236, dated Oct. 16, 2009 (16 pages).
International Search Report and Written Opinion for International Patent Application No. PCT/US2008/001505, dated Dec. 3, 2008 (8 pages).
International Search Report and Written Opinion for International Patent Application No. PCT/US2008/073215, dated Jan. 21, 2009 (12 pages).
International Search Report and Written Opinion for International Patent Application No. PCT/US2007/064728, dated Jul. 31, 2007 (13 pages).
International Search Report and Written Opinion for International Patent Application No. PCT/US2008/060936, dated Nov. 6, 2008 (12 pages).
Written Opinion of the International Searching Authority for International Patent Application No. PCT/US2006/026218, dated Dec. 12, 2006 (7 pages).
Written Opinion of the International Searching Authority for International Patent Application No. PCT/US2005/007108, dated Jun. 27, 2005 (6 pages).
Written Opinion of the International Search Authority for International Patent Application No. PCT/US2007/064728, dated Jul. 31, 2007 (9 pages).
Abouraddy et al., "Towards multimaterial multifunctional fibres that see, hear, sense, and communicate," Nature Materials, May 2007, pp. 336-342, vol. 6.
"Speciality Guidewires," retrieved from the Internet on Jun. 18, 2014:, http://www.galtmedical.com/pdf/Guidewires.pdf (2 pages).
Berthold, III, "Historical Review of Microbend Fiber-Optic Sensors," Journal of Lightwave Technology, Jul. 1995, pp. 1193-1199, vol. 13, No. 7.
Blandino et al., "Three-dimensional shape sensing for inflatable booms," 46th AIAA/ASME/ASCE/AHS/ASC Structures, Structural Dynamics & Materials Conference, Conference Dates: Apr. 18-21, 2005 (10 pages).
Capouilliet et al., "A Fiber Bragg Grating Measurement System for Monitoring Optical Fiber Strain" (9 pages).
Childers et al., "Recent development in the application of optical frequency domain reflectometry to distributed Bragg grating sensing," Luna Innovations and NASA Langley Research Center joint PowerPoint presentation (26 pages).
Danisch et al., "Bend Enhanced Fiber Optic Sensors in a Teleoperation Application," Fiber Optic and Laser Sensors XI, 1993, pp. 73-85, SPIE vol. 2070.
Danisch et al., "Spatially continuous six degree of freedom position and orientation sensor," Sensor Review, 1999, pp. 106-112, vol. 19.
Davis et al., "Fiber-optic bragg grating array for shape and vibration mode sensing," 1994, pp. 94-102, SPIE vol. 2191.
Davis, "Strain Survey of an F/A-18 Stabilator Spindle Using High Density Bragg Grating Arrays," Feb. 2005 (33 pages).
Duncan, "Sensing Shape: Fiber-Bragg-grating sensor arrays monitor shape at a high resolution," Spie's OE Magazine, Sep. 2005, pp. 18-21.
Duncan et al., "A distributed sensing technique for aerospace applications," Luna Innovations, Inc., American Institute of Aeronautics and Astronautics, 2004 (8 pages).
Duncan et al., "Characterization of a fiber optic shape and position sensor," Conference Title: Smart Structures and Materials 2006: Smart Sensor Monitoring Systems and Applications; San Diego, CA, Conference Date: Monday Feb. 27, 2006, Published in: Proc. SPIE, vol. 6167, 616704.
Duncan et al., "Fiber-optic shape and position sensing," Proceedings of the 5th International Conference on Structural Health Monitoring (2005), Structural Health Monitoring, 2005: Advancements and Challenges for Implementation (8 pages).
Duncan et al., "High-accuracy fiber-optic shape sensing," Conference Title: Sensor Systems and Networks: Phenomena, Technology, and Applications for NDE and Health Monitoring 2007, San Diego, California, USA, Conference Date: Monday Mar. 19, 2007, Published in: Proc. SPIE, vol. 6530 (11 pages).
Duncan et al., "Use of high spatial resolution fiber-optic shape sensors to monitor the shape of deployable space structures," Space Technology and Applications Int.Forum-Staif 2005 (7 pages).
Flockhart et al., "Two-axis bend measurement with Bragg gratings in multicore optical fiber," Optics Letters, Mar. 15, 2003, pp. 387-389, vol. 28, No. 6.
Froggatt et al., "Distributed measurement of static strain in an optical fiber with multiple Bragg gratings at nominally equal wavelengths," Applied Optics, Apr. 1, 1998, pp. 1741-1746, vol. 37, No. 10.
Froggatt et al., "High-spatial-resolution distributed strain measurement in optical fiber with Rayleigh scatter," Applied Optics, Apr. 1, 1998, pp. 1735-1740, vol. 37, No. 10.
Froggatt, "Intracore and extracore examination of fiber gratings with coherent detection," Thesis (PhD), 2000 (156 pages).
Froggatt et al., "Distributed Fiber-Optic Strain and Temperature Sensors Using Photoinduced Bragg Gratings," Thesis (Masters of Science), Feb. 1995 (22 pages).
Gander et al., "Bend Measurement using multicore optical fiber," Proceedings of OFS-12, Oct. 1997, pp. 166-169.
Gander et al., "Measurement of bending in two dimensions using multicore optical fibre," European Workshop on Optical Fibre Sensors, Jun. 1998, pp. 64-68, SPIE vol. 3483.
Gifford et al., "Swept-wavelength interferometric interrogation of fiber Rayleigh scatter for distributed sensing applications," Fiber Optic Sensors and Applications V, 2007, pp. 67700F-1-67700F-9, SPIE vol. 6770.
Grant et al., "Investigation of structural properties of carbon-epoxy composites using fiber-bragg gratings," Applications of Photonic Technology 5, 2002, pp. 191-199, Proceedings SPIE vol. 4833.
Grobnic et al., "Localized High Birefringence Induced in SMF-28 Fiber by Femtosecond IR Laser Exposure of the Cladding," Journal of Lightwave Technology, Aug. 2007, pp. 1996-2001, vol. 25, No. 8.
Grossman et al., "Development of microbend sensors for pressure, load, displacement measurements in civil engineering," Downloaded from SPIE Digital Library on Nov. 4, 2010, May 1994, pp. 112-125, vol. 2191.
Hayano et al., "Structural Health Monitoring System Using FBG Sensor Simultaneous Detection of Acceleration and Strain," Department of System Design Engineering, Keio University (14 pages).
Heo et al., "Design of TR-EFPI fiber optic pressure sensor for the medical application," Korea Advanced Institute of Science and Technology (6 pages).
Hill et al., "Fiber Bragg Grating Technology Fundamentals and Overview," Journal of Lightwave Technology, Aug. 1997, pp. 1263-1276, vol. 15, No. 8.
Hotate et al., "Proposal and experimental verification of Bragg wavelength distribution measurement within a long-length FBG by synthesis of optical coherence function," Optics Express, May 26, 2008, pp. 7881-7887, vol. 16, No. 11.
Huang et al., "Continuous arbitrary strain profile measurements with fiber bragg gratings," Smart Materials and Structures, 1998, pp. 248-256, vol. 7.
Janssen et al., "Signal Averaging in the Undergraduate Laboratory," Europe Journal of Physics, 1988, pp. 131-134, vol. 9.
Katsuki et al., "The Experimental Research on the Health Monitoring of the Concrete Structures Using Optical Fiber Sensor," BAM International Symposium, Sep. 16-19, 2003 (7 pages).
Kersey et al., "Fiber Grating Sensors," Journal of Lightwave Technology, Aug. 1997, pp. 1442-1463, vol. 15, No. 8.
Kim et al., "Micromachined Fabry-Perot Cavity Pressure Transducer," IEEE Photonics Technology Letters, Dec. 1995, pp. 1471-1473, vol. 7, No. 12.
Kirby et al., "Optimal sensor layout for shape estimation form strain sensors," Smart Structures and Materials, 1995, pp. 367-376, vol. 2444.

(56) References Cited

OTHER PUBLICATIONS

Klute et al., "Fiber-optic shape sensing and distributed strain measurements on a morphing chevron," 44th AIAA Aerospace Sciences Meeting and Exhibit, Conference dates: Jan. 9-12, 2006, American Institute of Aeronautics and Astronautics (25 pages).
Kreger et al., "Distributed strain and temperature sensing in plastic optical fiber using Rayleigh scatter," Fiber Optic Sensors and Applications VI, 2009, pp. 73160A-1-73160A-8, vol. 7316.
Kreger et al., "High-resolution extended distance distributed fiber-optic sensing using Rayleigh backscatter," Sensor Systems and Networks: Phenomena, Technology, and Applications for NDE and Health Monitoring, 2007, pp. 65301R-1-65301R-10, vol. 6530.
Kunzler et al., "Damage Evaluation and Analysis of Composite Pressure Vessels Using Fiber Bragg Gratings to Determine Structural Health," 2005 (9 pages).
Lawrence et al., "Multi-parameter sensing with fiber bragg gratings," SPIE, 1996, pp. 24-31, vol. 2872.
Lawrence et al., "A Fiber Optic Sensor for Transverse Strain Measurement," Experimental Mechanics, Sep. 1999, pp. 202-209, vol. 39, No. 3.
Lee et al., "Intraoperative Use of Duel Fiberoptic Catheter for Simultaneous In Vivo Visualization and Laser Vaporization of Peripheral Atherosclerotic Obstructive Disease," Catheterization and Cardiovascular Diagnosis, 1984, pp. 11-16, vol. 10.
Lequime et al., "Fiber optic pressure and temperature sensor for down-hole applications," Fiber Optic Sensors: Engineering and Applications, 1991, pp. 652-657, Proceedings SPIE vol. 1511.
Lopatin et al., "Distributed Measurement of Strain in Smart Materials Using Rayleigh Scattering," 32 International SAMPE Technical Conference, conference dates: Nov. 5-9, 2000, pp. 231-241.
Maas, "Shape measurement using phase shifting speckle interferometry," Laser Interferometry IV: Computer-Aided Interferometry, 1991, pp. 558-568, Proceedings SPIE vol. 1553.
Macdonald et al., "Frequency domain optical reflectometer," Applied Optics, May 15, 1981, pp. 1840-1844, vol. 20, No. 10.
Measures et al., "Fiber Optic Strain Sensing," Fiber Optic Smart Structures, 1995, pp. 171-247.
Mihailov et al., "UV-induced polarization-dependent loss (POL) in tilted fibre Bragg gratings: application of a PDL equalizer," IEE Proc.-Optoelectron., Oct./Dec. 2002, pp. 211-216, vol. 149, No. 5/6.
Miller et al., "Fiber-optic shape sensing for flexible structures," Fiber Optic Smart Structures and Skins II, 1989, pp. 399-404, SPIE vol. 1170.
Miller et al., "Shape Sensing Using Distributed Fiber Optic Strain Measurements," Second European Workshop on Optical Fibre Sensors, 2004, pp. 528-531, Proc. of SPIE vol. 5502.
Morey, "Fiber-optic bragg grating sensors," Fiber Optic and Laser Sensors VII, 1989, pp. 98-107, SPIE vol. 1169.
Ohn et al., "Arbitrary strain profile measurement within fibre gratings using interferometric Fourier transform technique," Electronics Letters, Jul. 3, 1997, pp. 1242-1243, vol. 33, No. 14.
Pinet et al., "True challenges of disposable optic fiber sensors for clinical environment," Third European Workshop on Optical Fibre Sensors, 2007, pp. 66191Q-1-66191Q-4, Proceedings SPIE vol. 6619.
Posey et al., "Strain sensing based on coherent Rayleigh scattering in an optical fibre," Electronics Letters, Sep. 28, 2000, pp. 1688-1689, vol. 36, No. 20.
Raum et al., "Performance Analysis of a Fiber-Optic Shape Sensing System," Collection of Technical papers—44th AIAA, 2006, (11 pages).
Raum, "Error Analysis of Three Dimensional Shape Sensing Algorithm," Apr. 26, 2005 (13 pages).
Reyes et al., "Tunable POL of Twisted-Tilted Fiber Gratings," IEEE Photonics Technology Letters, Jun. 2003, pp. 828-830, vol. 15, No. 6.

Satava, "How the Future of Surgery is Changing: Robotics, Telesurgery, Surgical Simulators and Other Advanced Technologies," May 2006, pp. 1-21.
Sato et al., "Ground strain measuring system using optical fiber sensors," SPIE Conference on Sensory Phenomena and Measurement Instrumentation for Smart Structures and Materials, Mar. 1999, pp. 470-479, vol. 3670.
Schreiber et al., "Stress-induced Birefringence in Large-mode-area micro-structured optical fibers," Optics Express, May 16, 2005, pp. 3637-3646, vol. 13, No. 10.
Schulz et al., "Advanced Fiber Grating Strain Sensor Systems for Bridges, Structures, and Highways," (11 pages).
Schulz et al., "Health monitoring of adhesive joints using multi-axis fiber grating strain sensor system," (12 pages).
Soller et al., "High Resolution Optical Frequency Domain Reflectometry for Characterization of Components and Assemblies," Optics Express, Jan. 24, 2005, pp. 666-674, vol. 13, No. 2.
Soller et al., "Optical frequency domain reflectometry for single- and multi-mode avionics fiber-optics applications," IEEE Conference, 2006 pp. 38-39.
Sorin, "Survey of Different Techniques," Optical Reflectometry for Component Characterization, 1997, Chapter 10, Section 10.5, pp. 424-429.
Tian et al., "Torsion Measurement Using Fiber Bragg Grating Sensors," Experimental Mechanics, Sep. 2001, pp. 248-253, vol. 41, No. 3.
Trimble, "A Successful fiber sensor for medical applications," Fiber Optic Sensors in Medical Diagnostics, 1993, pp. 147-150, SPIE vol. 1886.
Udd et al., "Usage of Multi-Axis Fiber Grating Strain Sensors to Support Nondestructive Evaluation of Composite Parts and Adhesive Bond Lines," Structural Health Monitoring Workshop (9 pages).
Udd, "Good Sense," Spie's OE Magazine, Aug. 2002, pp. 27-30.
Udd et al., "Multidimensional strain field measurements using fiber optic grating sensors," Smart Structures and Materials 2000: Sensory Phenomena and Measurement Instrumentation for Smart Structures and Materials, 2000, pp. 254-262, Proceedings SPIE vol. 3986.
Udd et al., "Progress on developing a multiaxis fiber optic strain sensor," Third Pacific Northwest Fiber Optic Sensor Workshop, 1997, pp. 50-56, Proceedings SPIE vol. 3180.
Walker et al., "Shaping the radiation field of tilted fiber Bragg gratings," J. Opt. Soc. Am. B, May 2005, pp. 962-975, vol. 22, No. 5.
Wippich et al., "Tunable Lasers and Fiber-Bragg-Grating Sensors," The Industrial Physicist, Jun./Jul. 2003, pp. 24-27.
Wong et al., "Distributed Bragg grating integrated-optical filters: Synthesis and fabrication," J. Vac. Sci. Technol. B., Nov./Dec. 1995, pp. 2859-2864, vol. 13, No. 6.
Xu et al., "Miniature fiber optic pressure and temperature sensors," Fiber Optic Sensor Technology and Applications IV, 2005, pp. 600403-1-600403-6, Proceedings SPIE vol. 6004.
Xue et al., "Simultaneous Measurement of Stress and Temperature with a Fiber Bragg Grating Based on Loop Thin-Wall Section Beam," Applied Optics, Mar. 2, 2006 (17 pages).
Ye et al., "A Polarization-maintaining Fiber Bragg Grating Interrogation System for Multi-Axis Strain Sensing," Measurement Science and Technology, 2002, pp. 1446-1449, vol. 13.
Zhang et al., "FBG Sensor Devices for Spatial Shape Detection of Intelligent Colonscope," IEEE, Apr. 2004, pp. 835-840.
Zhang, "Novel shape detection systems based on FBG sensor net for intelligent endoscope," Journal of Shanghai University (English Edition), Apr. 2006, pp. 154-155, vol. 10, No. 2.
Zhang et al., "Fiber-Bragg-grating-based seismic geophone for oil/gas prospecting," Optical Engineering, Aug. 2006, pp. 84404-1-84404-4, vol. 45, No. 8.
Wu et al., Sep. 2003, Fabrication of self-apodized short-length fiber Bragg gratings, Applied Optics, 42(25):5017-5023.

* cited by examiner

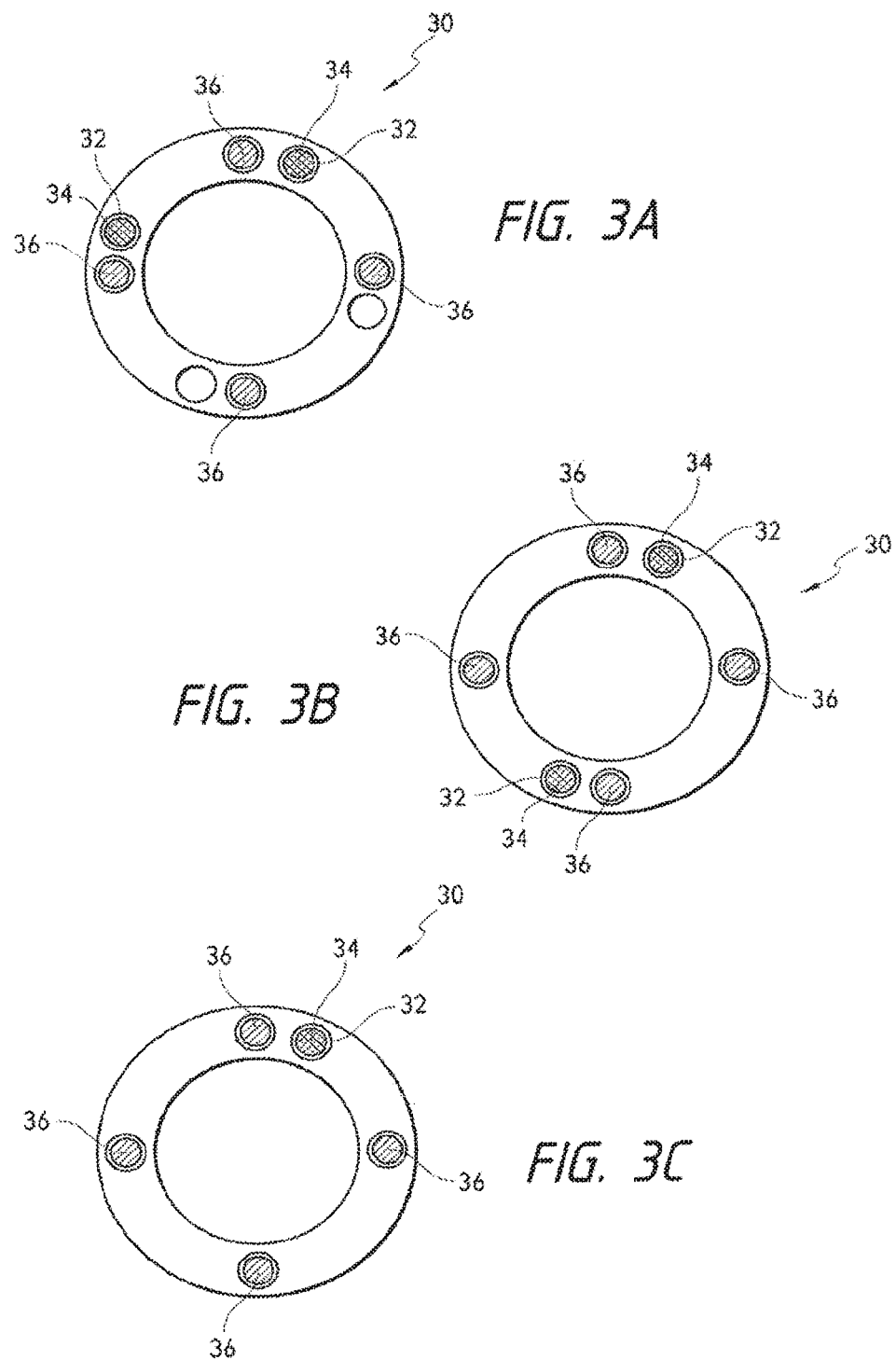

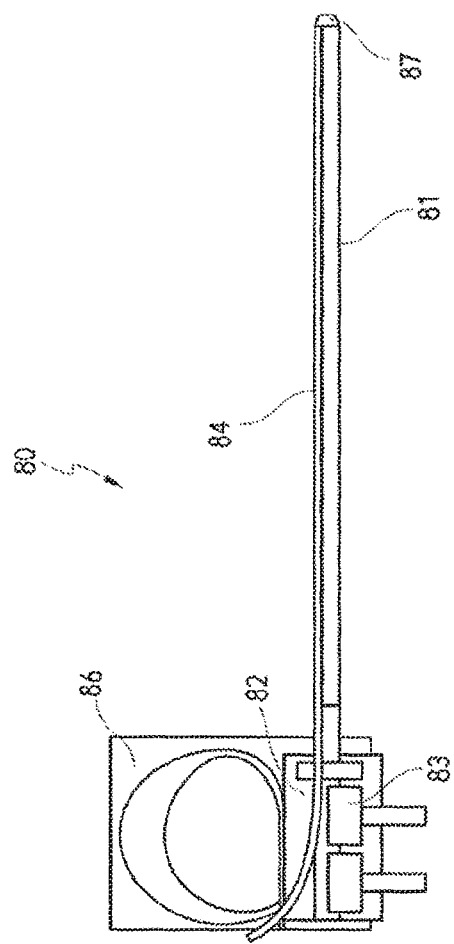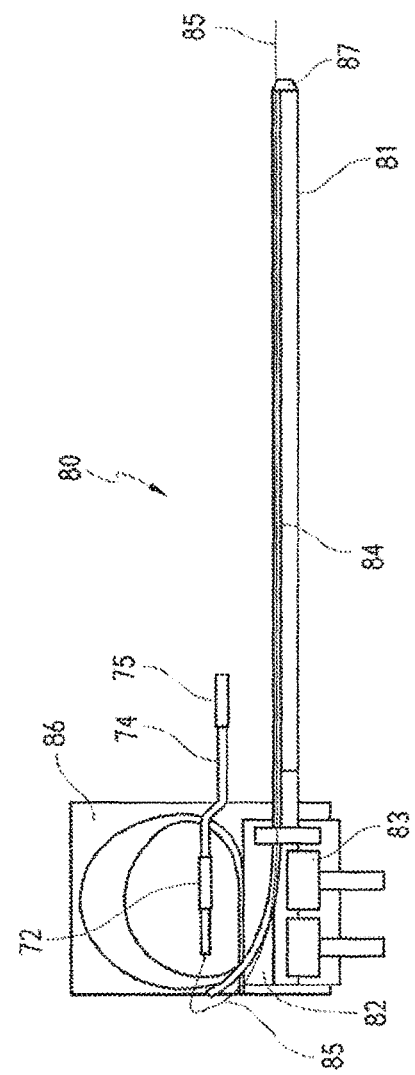

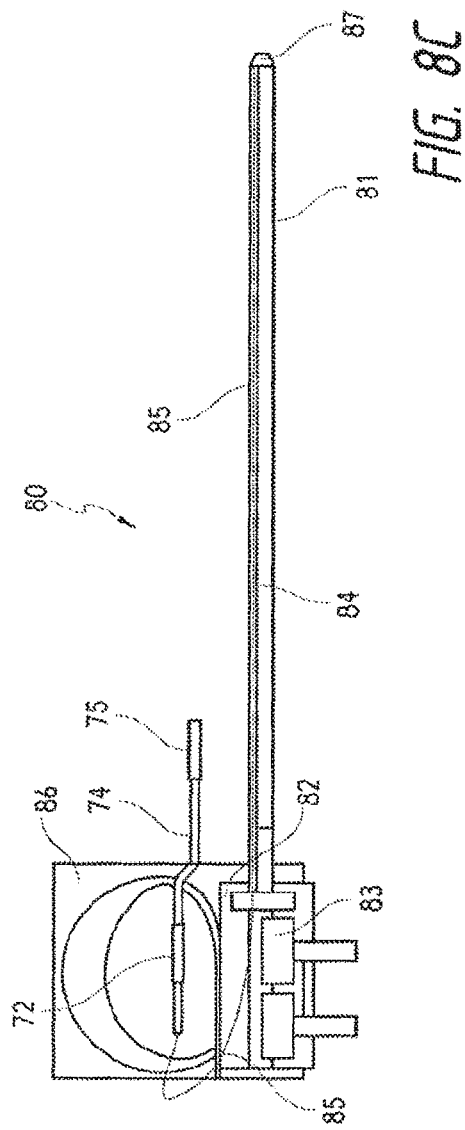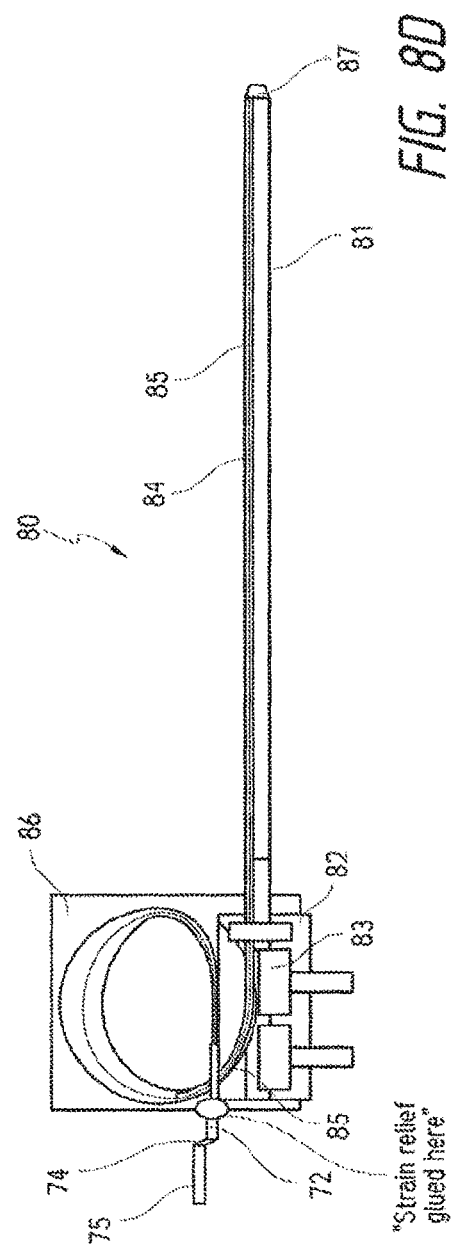

APPARATUS AND METHODS FOR FIBER INTEGRATION AND REGISTRATION

CROSS REFERENCE TO RELATED APPLICATION

This application is a continuation of U.S. patent application Ser. No. 14/860,291 filed Sep. 21, 2015, entitled "Apparatus and Methods for Fiber Integration and Registration," which is a continuation of U.S. Non-Provisional patent application Ser. No. 13/314,057, now U.S. Pat. No. 9,138,166, filed Dec. 7, 2011, entitled "Apparatus and Methods for Fiber Integration and Registration," which claims the benefit of U.S. Provisional Patent Application No. 61/513,488, filed Jul. 29, 2011. The above-referenced patent applications are all incorporated herein by reference in their entireties for all purposes.

This application is also related to and incorporates herein by reference in its entirety for all purposes U.S. patent application Ser. No. 12/837,440, now U.S. Pat. No. 8,780,339, filed Jul. 15, 2010, entitled "Fiber Shape Sensing Systems and Methods."

FIELD OF THE INVENTION

The present apparatus, systems and methods relate generally to apparatus and methods for integrating and/or registering a shape sensing fiber in or to an instrument or device.

BACKGROUND

Currently known minimally invasive procedures for diagnosis and treatment of medical conditions use elongate instruments, such as catheters or more rigid arms or shafts, to approach and address various tissue structures within the body. For various reasons, it is valuable to be able to determine the 3-dimensional spatial position of portions of such elongate instruments relative to other structures, such as the operating table, other instruments, or pertinent tissue structures. Conventional technologies such as electromagnetic position sensors may be utilized to measure 3-dimensional spatial position but may be limited in utility for elongate medical instrument applications due to hardware geometric constraints, electromagnetivity issues, etc. An alternative solution is the use of optical fibers containing optic shape sensors, available from suppliers such as Luna Innovations, Inc., of Blacksburg, Va., Micron Optics, Inc., of Atlanta, Ga., LxSix Photonics, Inc., of Quebec, Canada, and Ibsen Photonics A/S, of Denmark. By integrating an optical fiber into an elongate instrument such as a catheter, the real time 3-dimensional spatial shape of any or all of the length of the catheter may be determined.

Catheter structures may be designed to include an optical fiber. However, large strain changes induced by mechanical structures (such as pinching, twisting, etc.) may disrupt the accuracy of shape algorithms. The addition of components to a catheter may negatively affect the performance of a catheter (such as stiffness, inner and outer diameters, etc.).

There remains a need for apparatus and methods to improve integration and registration of a shape sensing fiber in or to an elongate instrument or other device and/or to a mechanical structure that is meaningful to the instrument or device/system.

BRIEF SUMMARY

In certain variations, various apparatus, systems and methods for integrating and/or registering a shape sensing fiber in various instruments, for example, an elongate instrument are described herein. Such systems and methods may allow for the shape detection of an elongate instrument or other structure.

In certain variations, a system may include an elongate instrument having a proximal end, a distal end and at least one lumen defined therein. The system may also include a shape sensing fiber, where at least a first portion of the fiber is positioned in the lumen of the elongate instrument. A second portion of the fiber may be fixed or otherwise attached in a known location or position relative to the elongate instrument or to another structure such that the coordinate system of the fiber can be matched to the coordinate system of the elongate instrument to register the fiber to the elongate instrument. As a result of this registration, the shape of an elongate instrument may be detected or determined.

In certain variations, a method for registering a fiber to an elongate instrument and/or detecting the shape of an elongate instrument may include one or more of the following steps. An assembly having an elongate instrument and a shape sensing fiber may be operated. The elongate instrument may have a proximal end, a distal end and at least one lumen defined therein, where least a first portion of the fiber may be positioned in the lumen of the elongate instrument. At least a second portion of the fiber may be fixed in a known location or position relative to the elongate instrument or to another structure. A position of the fixed portion of the fiber may be measured or ascertained relative to the elongate instrument to match the coordinate system of the fiber with the coordinate system of the elongate instrument to register the fiber to the elongate instrument.

In certain variations, a system may include an elongate instrument having a proximal end, a distal end and at least one lumen defined therein. The system may also include a shape sensing fiber, wherein at least a first portion of the fiber is positioned in the lumen of the elongate instrument. A second portion of the fiber may be configured in a known shape, plane or other orientation relative to the elongate instrument or to another structure such that the coordinate system of the fiber may be matched to the coordinate system of the elongate instrument to register the fiber to the elongate instrument.

In certain variations, a method of detecting the shape of an elongate instrument may include one or more of the following steps. Operating an assembly having an elongate instrument and a shape sensing fiber, where the elongate instrument may have a proximal end, a distal end and at least one lumen defined therein may be performed. At least a first portion of the fiber may be positioned in the lumen of the elongate instrument and at least a second portion of the fiber may be configured in a known shape, plane or other orientation. A position of the second portion of the fiber may be measured or ascertained relative to the elongate instrument to match the coordinate system of the fiber with the coordinate system of the elongate instrument to register the fiber to the elongate instrument.

In certain variations, a method for detecting the shape of an elongate instrument may include one or more of the following steps. Operating an assembly having an elongate instrument and a shape sensing fiber may be performed. The elongate instrument may have a proximal end, a distal end and at least one lumen defined therein. At least a first portion of the fiber may be positioned in the lumen of the elongate instrument and at least a second portion of the fiber may be fixed in a known location relative to the elongate instrument or to another structure. Saved registration data may be accessed regarding registration between the coordinate system of the fiber and the coordinate system of the elongate instrument from a memory component to determine the shape of the elongate instrument. Optionally, the structure may be a registration fixture which may be positioned in a known location relative to the elongate instrument.

In certain variations, a system may include an elongate instrument having a proximal end, a distal end and one or more lumens defined therein. The system may include a shape sensing fiber, where at least a portion of the fiber may be positioned within the lumen of the elongate instrument. The shape sensing fiber may have a service loop which allows for sliding or displacing of the fiber within the lumen of the elongate instrument when a distal portion of the elongate instrument is articulated, bent, navigated or manipulated. The system may also include a coil positioned within the lumen, and surrounding the fiber. The coil may be slideable within the lumen and the coil may maintain the lumen in an open state during articulation of the elongate instrument.

In certain variations, a system may include an elongate instrument having a proximal end, a distal end and at least one lumen defined therein. The system may include a housing coupled to a proximal portion of the elongate instrument, where the housing includes an interface for receiving an actuating force and transferring the actuating force to the elongate instrument to articulate a distal portion of the elongated instrument. The system may also include a shape sensing fiber. At least a first portion of the fiber may be positioned within the lumen of the elongate instrument, and a second portion of the fiber may be positioned within the housing. The second portion of the fiber may include a service loop which allows for sliding or displacing of the fiber within the lumen of the elongate instrument when the distal portion of the elongate instrument is articulated.

In certain variations, a method of actuating an elongate instrument may include one or more of the following steps. A system may be operatively coupled to a controller. The system may include an elongate instrument; a housing coupled to a proximal portion of the elongate instrument, where the housing comprises an interface for receiving an actuating force and transferring the actuating force to the elongate instrument to articulate a distal portion of the elongate instrument; and a shape sensing fiber. The elongate instrument may have a proximal end, a distal end and at least one lumen defined therein. At least a first portion of the fiber may be positioned within the lumen of the elongate instrument, and a second portion of the fiber may be positioned within the housing. The second portion of the fiber may include a service loop. Actuating motion may be transferred from the controller to the system to articulate the distal portion of the elongate instrument in at least one degree of freedom, where the service loop allows the fiber to slide or be displaced within the lumen of the elongate instrument when the distal portion of the elongate instrument is articulated, thereby controlling the amount of strain the fiber is subjected to and maintaining shape sensing properties of the fiber.

In certain variations, a system may include an elongate instrument having a proximal end, a distal end and at least one lumen defined therein. A housing may be coupled to a proximal portion of the elongate instrument, wherein the housing includes an interface for receiving an actuating force and transferring the actuating force to the elongate instrument to articulate a distal portion of the elongate instrument. The system also includes a shape sensing fiber. At least a first portion of the fiber may be positioned in the lumen of the elongate instrument. At least a second portion of the fiber may be positioned in the housing such that the coordinate system of the fiber can be matched to the coordinate system of the elongate instrument to register the fiber to the elongate instrument. The second portion of the fiber may include a service loop which allows for sliding or displacing of the fiber within the lumen of the elongate instrument when the distal portion of the elongate instrument is articulated.

In certain variations, a method of actuating an elongate instrument may include one or more of the following steps. An assembly may be operatively coupled to a controller. The assembly may include an elongate instrument; a housing coupled to a proximal portion of the elongate instrument, wherein the housing comprises an interface for receiving an actuating force and transferring the actuating force to the elongate instrument to articulate a distal portion of the elongate instrument; and a shape sensing fiber. At least a first portion of the fiber may be positioned in the lumen of the elongate instrument. At least a second portion of the fiber may be positioned in the housing such that the coordinate system of the fiber can be matched to the coordinate system of the elongate instrument to register the fiber to the elongate instrument. The second portion of the fiber may include a service loop. Actuation motion may be transferred from the controller to the assembly to articulate the distal end of the elongate instrument in at least one degree of freedom. The service loop may allow the fiber to slide or displace within the lumen of the elongate instrument when the distal portion of the elongate instrument is articulated, thereby controlling the amount of strain the fiber is subjected to. Saved registration data regarding registration between the coordinate system of the fiber and the coordinate system of the elongate instrument may be accessed from a memory component to determine the shape of the elongate instrument.

In one variation a method for integrating a shape sensing fiber in an elongate instrument may include inserting a fiber into a first lumen of the elongate instrument. The elongate instrument may include a support component positioned therein for maintaining patency of or otherwise supporting the first lumen during articulation of the elongate instrument. A distal end of the fiber may be fixed at a distal end of the elongate instrument and the fiber may remain free to slide or float within the first lumen of the elongate instrument.

In certain variations, an elongate instrument is provided. The elongate instrument may be configured to support the integration of a shape sensing fiber. The elongate instrument may include one or more lumens defined through the elongate instrument and one or more fibers. A distal end of a fiber may be fixed to a distal end of the elongate instrument. A support component may be positioned within the elongate instrument to maintain patency of or otherwise support one or more lumens during articulation of the elongate instrument. This may allow the fiber to slide or float within a lumen of the elongate instrument. Optionally, the fiber may include a service loop. Optionally, a registration fixture may be coupled to the elongate instrument. The registration fixture may have grooves for holding a fiber and/or an elongate instrument in certain shapes or orientations.

In certain variations, a method for registering a shape sensing fiber to an elongate instrument is provided. The method may include fixing at least a portion of the fiber to the elongate instrument or to a structure associated with the elongate instrument or providing an elongate instrument having a fiber fixed thereto or to an associated structure. Zero to six degrees of freedom may be ascertained from the fixed portion of the fiber. The location and/or orientation of the fixed portion of the fiber relative to the elongate instrument or to a structure associated with the elongate instrument may be determined to match the coordinate system of the fiber to the coordinate system of the elongate instrument, thereby registering the fiber to the elongate instrument.

In certain variations, a system is provided. The system may allow for the registering of a shape sensing fiber to an elongate instrument. The system may include a registration fixture configured to hold the elongate instrument and/or the complete length or a partial length of a fiber integrated in the elongate instrument in known positions or orientations such that data regarding the position or orientation of the partial or complete length of the fiber may be collected to calculate a transform between the coordinate system of the fiber and the coordinate system of the elongate instrument.

In certain variations, another method of registering a shape sensing fiber to an elongate instrument is provided. A known shape may be inserted or imposed in a fiber. The location of the known shape relative to a point on the elongate instrument or on a structure associated with the elongate instrument may be determined. The known shape in the fiber may be measured to create a transform between a fiber coordinate system and an elongate instrument coordinate system.

BRIEF DESCRIPTION OF THE SEVERAL VIEWS OF THE DRAWINGS

FIG. 3A-3C illustrate cross sectional views of variations of an elongate instruments having fibers placed at various positions in relation to several control wires.

FIGS. 8A-8D show a variation of a process for integrating a fiber into a catheter assembly

DETAILED DESCRIPTION

Variations of the devices, systems and methods described herein are best understood from the detailed description when read in conjunction with the accompanying drawings. It is emphasized that, according to common practice, the various features of the drawings may not be to-scale. On the contrary, the dimensions of the various features may be arbitrarily expanded or reduced for clarity. The drawings are taken for illustrative purposes only and are not intended to define or limit the scope of the claims to that which is shown.

Steerable Catheters (and Other Elongate Instruments)

Figure 1A:
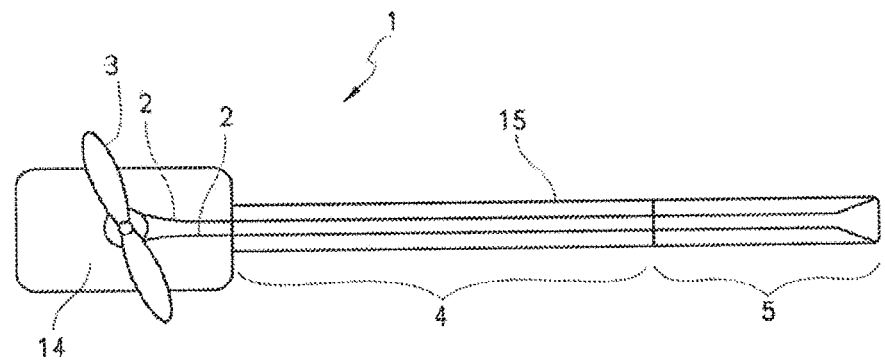
FIG. 1A illustrates a conventional manually-steerable catheter.

Referring to FIG. 1A, a conventional manually-steerable catheter (1) is depicted. Pullwires (2) may be selectively tensioned through manipulation of a handle (3) on the proximal portion of the catheter structure to make a more flexible distal portion (5) of the catheter bend or steer controllably. The pull wires can run from the proximal to distal end of the catheter terminating at a control ring positioned near the distal tip of the catheter. The handle (3) may be coupled, rotatably or slidably, for example, to a proximal catheter structure (14) which may be configured to be held in the hand, and may be coupled to the elongate portion (15) of the catheter (1). A more proximal, and conventionally less steerable, portion (4) of the catheter may be configured to be compliant to loads from surrounding tissues (for example, to facilitate passing the catheter, including portions of the proximal portion, through tortuous pathways such as those formed by the blood vessels), yet less steerable as compared with the distal portion (5).

Figure 1B:
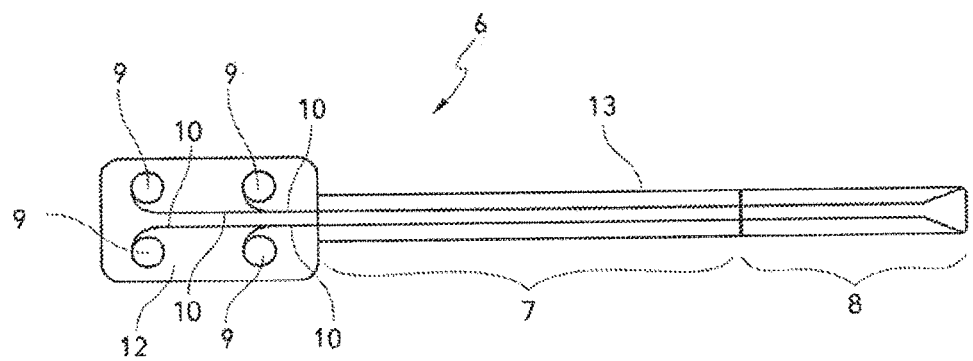
FIG. 1B illustrates a robotically-driven steerable catheter.

Referring to FIG. 1B, a robotically-driven steerable catheter (6), similar to those described in detail in U.S. patent application Ser. No. 11/176,598 and U.S. Provisional Patent Application 61/482,598 filed on May 4, 2011, each of which is incorporated by reference herein in its entirety for all purposes, is depicted. This catheter (6) of FIG. 1B has some similarities with the manually-steerable catheter (1) of FIG. 1A in that it has pullwires (10) coupled to a control ring associated distally with a more flexible section (8) configured to steer or bend when the pullwires (10) are tensioned in various configurations, as compared with a less steerable proximal portion (7) configured to be stiffer and more resistant to bending or steering. The depicted embodiment of the robotically-driven steerable catheter (6) comprises proximal axles or spindles (9) configured to primarily interface not with fingers or the hand, but with an electromechanical instrument driver configured to coordinate and drive, with the help of a computer, each of the spindles (9) to produce precise steering or bending movement of the catheter (6). The spindles (9) may be rotatably coupled to a proximal catheter structure (12) which may be configured to mount to an electromechanical instrument driver apparatus, such as that described in the aforementioned U.S. patent application Ser. No. 11/176,598, and may be coupled to the elongate portion (13) of the catheter (6).

Each of the embodiments depicted in FIGS. 1A and 1B may have a working lumen (not shown) located, for example, down the central axis of the catheter body, or may be without such a working lumen. If a working lumen is formed by the catheter structure, it may extend directly out the distal end of the catheter, or may be capped or blocked by the distal tip of the catheter. It is useful in many procedures to have precise 3-dimensional information regarding the shape of such catheters as well as the position of the distal tip the catheters or other elongate instruments, such as those available from suppliers such as the Ethicon Endosurgery division of Johnson & Johnson, or Intuitive Surgical Corporation. The examples and illustrations that follow are made in reference to a robotically-steerable catheter such as that depicted in FIG. 1B, but as would be appreciated by one of ordinary skilled in the art having the benefit of this disclosure, the same principles may be applied to other elongate instruments, such as the manually-steerable catheter depicted in FIG. 1A, or other elongate instruments, highly flexible or not, from suppliers such as the Ethicon Endosurgery division of Johnson & Johnson, Inc., or Intuitive Surgical, Inc.

Elongate instruments, such as the catheters described above, endoscopes, bronchoscopes, etc., may include various structures or features for integrating and/or for supporting the requirements of a shape sensing fiber (e.g., a fiber optic shape sensor) and its associated algorithms to obtain accurate shape and position measurements of the elongate instrument, while maintaining the ability of the elongate instrument to be accurately driven and articulated.

Examples of Shape Sensing Fibers

Various types of shape sensing fibers may be used with elongate instruments to measure shape and position. It is well known that by applying the Bragg equation (wavelength=2*d*sin(theta)) to detect wavelength changes in reflected light, elongation in a diffraction grating pattern positioned longitudinally along a fiber or other elongate structure maybe be determined. Further, with knowledge of thermal expansion properties of fibers or other structures which carry a diffraction grating pattern, temperature readings at the site of the diffraction grating may be calculated. "Fiberoptic Bragg grating" ("FBG") sensors or components thereof, available from suppliers such as Luna Innovations, Inc., of Blacksburg, Va., Micron Optics, Inc., of Atlanta, Ga., LxSix Photonics, Inc., of Quebec, Canada, and Ibsen Photonics AIS, of Denmark, have been used in various applications to measure strain in structures such as highway bridges and aircraft wings, and temperatures in structures such as supply cabinets.

The use of such technology in shapeable instruments is disclosed in commonly assigned U.S. patent application Ser. Nos. 11/690,116; 11/176,598; 12/012,795; 12/106,254; 12/507,727; 12/192,033; 12/236,478; and Ser. No. 12/837,440. The entirety of each of the above applications is incorporated by reference herein.

In an alternative variation, a single mode optical fiber is drawn with slight imperfections that result in index of refraction variations along the fiber core. These variations result in a small amount of backscatter that is called Rayleigh scatter. Changes in strain or temperature of the optical fiber cause changes to the effective length of the optical fiber. This change in the effective length results in variation or change of the spatial position of the Rayleigh scatter points. Cross correlation techniques can measure this change in the Rayleigh scattering and can extract information regarding the strain. These techniques can include using optical frequency domain reflectometer techniques in a manner that is very similar to that associated with low reflectivity fiber gratings. A more complete discussion of these methods can be found in M. Froggatt and J. Moore, "High-spatial-resolution distributed strain measurement in optical fiber with Rayleigh scatter", Applied Optics, Vol. 37, p. 1735, 1998 the entirety of which is incorporated by reference herein.

Methods and devices for calculating birefringence in an optical fiber based on Rayleigh scatter as well as apparatus and methods for measuring strain in an optical fiber using the spectral shift of Rayleigh scatter can be found in PCT Publication No. WO2006099056 filed on Mar. 9, 2006 and U.S. Pat. No. 6,545,760 filed on Mar. 24, 2000 both of which are incorporated by reference herein. Birefringence can be used to measure axial strain and/or temperature in a waveguide. Using Rayleigh scatter to determine birefringence rather than Bragg gratings offers several advantages. First, the cost of using Rayleigh scatter measurement is less than when using Bragg gratings. Rayleigh scatter measurement permits birefringence measurements at every location in the fiber, not just at predetermined locations. Since Bragg gratings require insertion at specific measurement points along a fiber, measurement of Rayleigh scatter allows for many more measurement points. Also, the process of physically "writing" a Bragg grating into an optical fiber can be time consuming as well as compromises the strength and integrity of the fiber. Such drawbacks do not occur when using Rayleigh scatter measurement.

Integration of Fibers in Steerable Catheters

When integrating a fiber into an elongate instrument, e.g., a manually or robotically steerable catheter, the distal end of the fiber and the distal end of the instrument can be fixed relative to one another. This provides for a reliable correlation between the shape of the fiber sensor and the actual shape of the instrument. If the fiber does not reside within the neutral axis (axis in which path length does not change during bending) of the elongate instrument (as is often the case) it can be beneficial to isolate the fiber from the axial strain of the instrument. This can be achieved by decoupling the fiber and the instrument (i.e., floating the fiber) along the length of the instrument.

Figure 2A:
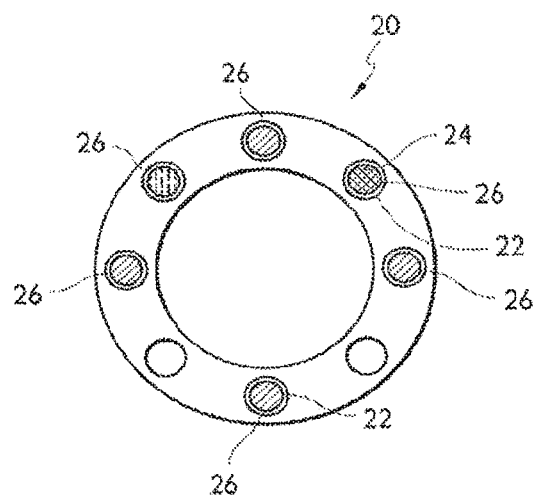
FIG. 2A illustrates a cross sectional view of a variation of an elongate instrument having lumens for incorporating a fiber.

In one variation, as shown in FIG. 2A, one or more lumens 22 may be defined through the elongate instrument 20 for receiving one or more fibers 24, such that a fiber 24 may be allowed to slide freely within the lumen 22 of the elongate instrument 20. By being allowed to slide freely within a lumen 22 of the elongate instrument 20, the maximum strain subjected to the fiber 24 will be reduced to levels low enough for the shape algorithms to process shape, strain, etc data. A free floating fiber 24 may avoid being stretched or compressed during the bending or articulation of an elongate instrument 20. A slidable or free floating fiber may allow the fiber to remain under the maximum allowable strain of the fiber.

Figure 2B:
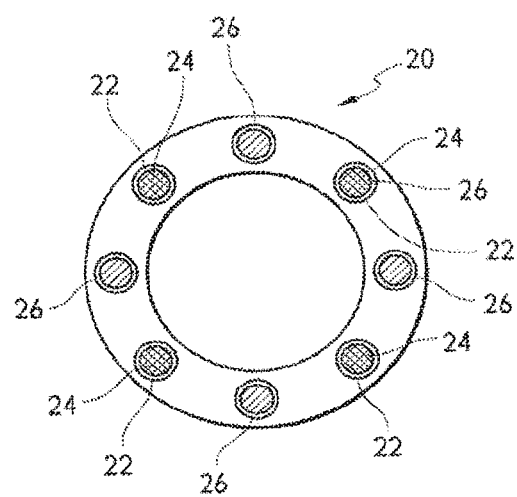
FIG. 2B illustrates a cross sectional view of a variation of an elongate instrument having a symmetrical or uniform structure.

In certain variations, a support component, e.g., a tube (e.g., polyimide), a liner (e.g., PTFE), coil, coil pipes, or braiding (polyimide) may be incorporated into or around any portion of a lumen of an elongate instrument to maintain the patency or openness of the lumen and minimize friction such that a fiber can slide freely or float within the lumen of the elongate instrument, or to provide reliable positioning of the lumen within the elongate instrument, or to reinforce a lumen. Such support components may hold a lumen open and prevent collapse of the lumen during articulation of the elongate instrument to avoid binding or pinching of the fibers. Such support components may be incorporated into an articulation section of an elongate instrument, along the entire length of the catheter, or along other various sections along the length of the catheter. For example, FIGS. 2A-2B show one or more lumens 22 in an elongate instrument 20 having a coil 26 positioned therein, e.g., positioned coaxially with the lumen to surround a fiber positioned within the lumen of the coil. Fibers may be positioned within a lumen of certain support components, such as a tube, coil or coil pipe, positioned within the lumen of the elongate instrument. In one example, the support component may include an expanded coil or coil pipe positioned in a distal articulation section of the elongate instrument and a braid or polyimide braid may be positioned in a proximal section or other portion of the elongate instrument.

Figure 5:
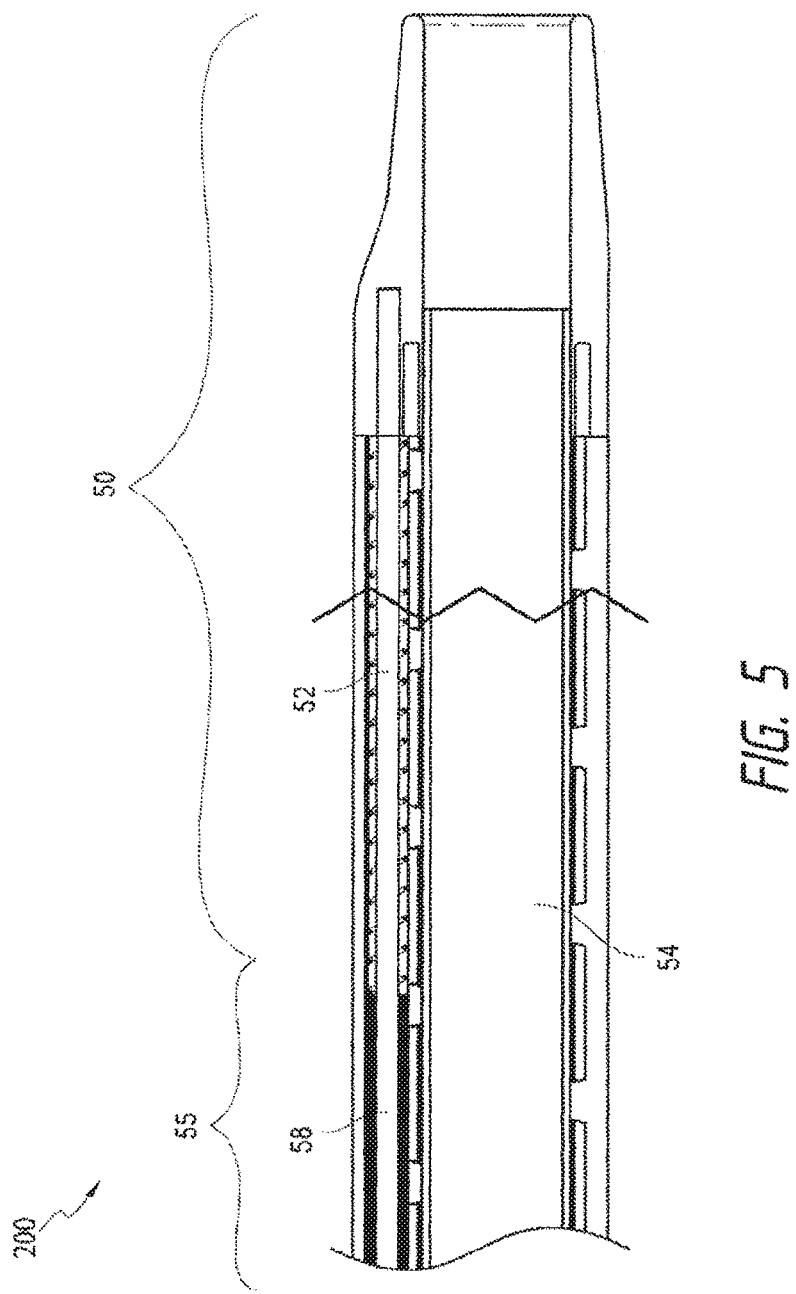
FIG. 5 illustrates a cross sectional view of a variation of an elongate instrument having fiber lumens positioned therein.

FIG. 5 illustrates a variation of an elongate instrument 200 wherein a distal section 50 of the elongate instrument includes a first fiber lumen 52 and a proximal section 55 of the elongate instrument 200 includes a second fiber lumen 58, e.g., axially aligned with the first fiber lumen 52. Both fiber lumens 52, 58 can be integrated into the wall of the elongate instrument 200 leaving an open center working lumen 54 in the elongate instrument 200. Additionally, control wire lumens (not shown) may be integrated into the elongate instrument wall running from a proximal end of the elongate instrument 200 to a distal end. In some cases, in order to controllably and reliably articulate the elongate instrument 200 it can be desirable to construct the elongate instrument distal section 50, e.g., a distal articulation section, such that is has lower axial stiffness than the proximal section 55. The following will describe a variation of a construction that will provide such a configuration while providing for open fiber lumens 52, 58 which may include low-friction bearing surfaces for contact with a fiber.

Figure 5A:
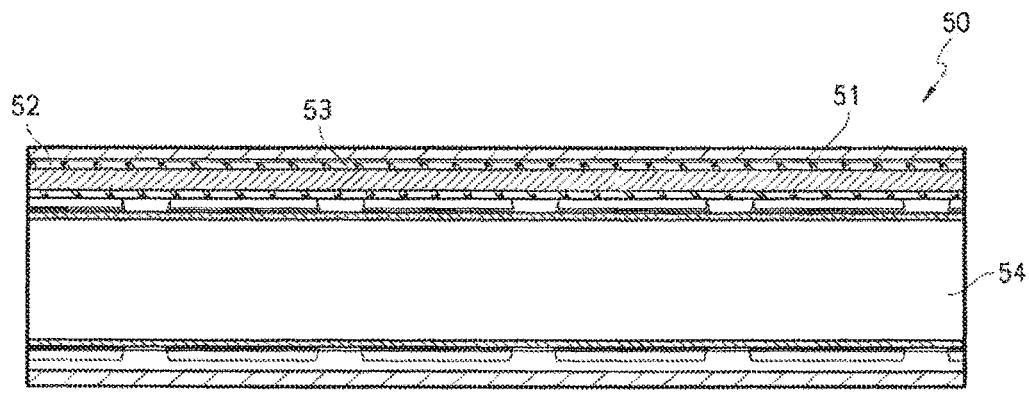
FIGS. 5A-5B illustrate cross sectional views of a variation of an elongate instrument having a coil pipe positioned inside a lumen of the elongate instrument. A fiber is positioned inside the coil pipe.
Figure 5B:
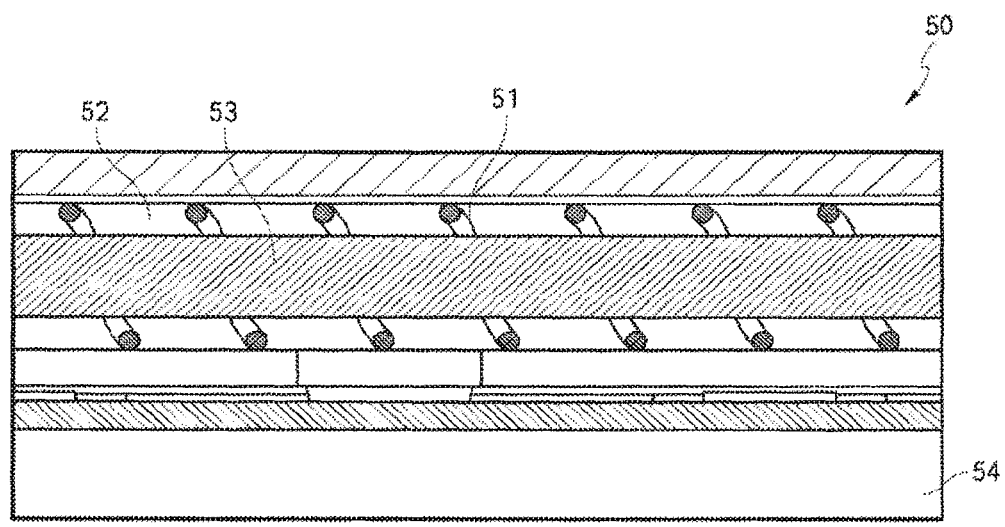

FIGS. 5A-5B illustrate a magnified cross section of the distal section 50 of the elongate instrument 200 showing the center lumen 54 and the first fiber lumen 52 as well as a coil, e.g. a coil pipe 51 or expanded coil pipe, and a fiber 53 positioned within the coil pipe 51. As shown in FIG. 5, the coil pipe 51 can be positioned inside the first fiber lumen 52 in the wall of the distal section 50 of the elongate instrument. In this variation, the coil pipe 51 may have an open pitch and may be fixed at its distal and proximal ends to the elongate instrument 200 such that the coil pipe 51 is free to float or extend and/or compress within the first fiber lumen 52. The coil pipe 51 may have a thin wall thickness, and/or a low axial stiffness. The first fiber lumen 52 surrounding the coil pipe 51 may be composed of an elastomer, e.g., Polyether Block Amide (PEBAX®). The coil pipe-in-lumen construct, while low in axial and bending stiffness, allowing the distal section of the elongate instrument to remain flexible, has high hoop strength and holds the first fiber lumen 52 open during bending. By allowing the coil pipe 51 to float instead of embedding it in the wall of the elongate instrument 200, the coil pipe 51 separates the fiber 53 from the first fiber lumen wall. The fiber 53 is in direct contact with the coil pipe, which may be made from a metal or similar material, and any friction between the fiber and the coil would be less than the friction between the fiber and the lumen wall if the fiber were in contact with the lumen wall. This allows the coil pipe 51 positioned within the first fiber lumen 52 to provide a low-friction bearing surface for contact with the inner fiber 53.

The coil pipe 51 provides one mechanism for floating a fiber 53 inside a lumen 52 that undergoes bending strain such that: the lumen 52 remains patent (open) under bending strain; the fiber 53 to lumen 52 wall interface remains low in friction under bending strain; and/or the addition of the coil or mechanism does not contribute significantly to the overall axial and bending stiffness of the elongate instrument 200.

While the coil or coil pipe 51 is illustrated in FIGS. 5, 5A, and 5B as being integrated into the distal section 50 of the elongate instrument 200, it should be understood that the coil or coil pipe 51 could extend into any length of the proximal section 55 of the elongate instrument 200 or the entire length or substantially entire length of the elongate instrument 200. The coil pipe 51 could be fixed at its distal end to the elongate instrument 200 and/or at its proximal end to the elongate instrument, or could be allowed to be completely free floating within a closed lumen in the elongate instrument 200.

Expanded coil pipes may vary in size. For example, expanded coil pipes having a diameter ranging from about 1-2 mm or mils may be used in an elongate instrument where space constraints are an issue. Depending on the desired stiffness of the elongate instrument, coil pipe stiffness may be reduced by stretching the coil pipe so that tensile and compression stiffness of the coil pipe is decreased below that of other components of the elongate instrument. This reduces the effects of any potential increased bending stiffness or non-uniform bending stiffness that may be caused by the addition of a coil pipe to the elongate instrument.

Figure 5C:
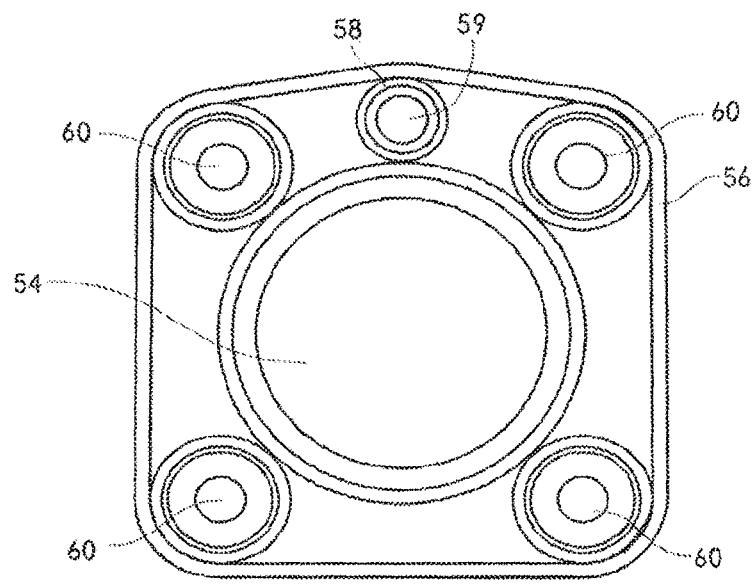
FIGS. 5C-5D illustrate cross sectional views of variations of an elongate instrument having a lumen for a fiber incorporated into the braid of the elongate instrument.
Figure 5D:
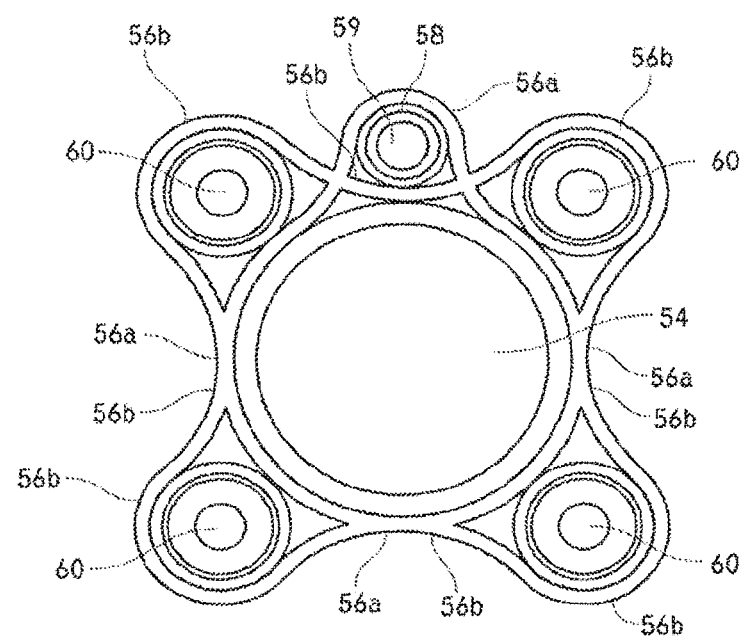

FIGS. 5C-5D each illustrates a cross section of the proximal section 55 of the elongate instrument 200 having the second fiber lumen 58 incorporated into a braid 56 of or in a wall 57 of the elongate instrument 200. Additionally, a set of control wire lumens 60 and the center lumen 54 are provided. In this variation, the second fiber lumen 58 with high hoop strength can be made of polyimide or a similar material providing higher stiffness than PEBAX or other material used to make the first fiber lumen 52, allowing for higher stiffness in the proximal section 55 of the elongate instrument 200 compared to the distal section, if desired. The second fiber lumen 58 along with the control wire lumens 60, and the center lumen 54 may be incorporated into the braid 56 of the elongate instrument 200 or elongate instrument or shaft wall 57. This braid 56 may be encapsulated with a soft polymer, e.g., PEBAX.

FIG. 5C illustrates a variation of a braid pattern which can be used to secure lumens, including the second fiber lumen 58, the center lumen 54, and control wire lumens 60. In this variation, one layer of braid 56 can be laid underneath the control wire lumens 60 and the second fiber lumen 58 surrounding the center lumen 54 while another layer of braid 56 can be laid over the control wire lumens 60 and the second fiber lumen 58.

FIG. 5D illustrates an alternative variation of a braid pattern. The second fiber lumen 58 and control wire lumens 60 are braided into the catheter wall with multiple layers of braid 56a and 56b, which cross and/or wind around each lumen 58, 60. In one variation, a layer of braid 56a may wind around the outer diameter of the second fiber lumen 58, between the control wire lumens 60 and the center lumen 54. Another layer of braid 56b may be wound, e.g., simultaneously, in the opposite direction as the braid 56a, around the outer diameters of the control wire lumens 60 but winding close to the center lumen 54 between each control wire lumen 60. The braid 56b winds between the second fiber lumen 58 and the center lumen 54. The braid pattern creates a diamond like pattern on or in the elongate instrument when viewed from a side view (not shown).

The braid pattern of FIG. 50 holds the second fiber lumen 58 in a fixed or substantially fixed radial position throughout the length or at least a portion of the length of the elongate instrument or the shaft of the elongate instrument 200, allowing for a reliable correlation between the shape and orientation of the fiber 59, positioned in the second fiber lumen 58, and the elongate instrument's shape and orientation. Additionally, the braid pattern of FIG. 50 provides for a smaller, compact cross sectional area of the elongate instrument compared to the previous braid shown in FIG. 5C. The encapsulated braid 56 and lumen 58 construct provides good kink resistance such that the fiber 59, positioned in the lumen 58, is not impinged on or such that any impingement is minimal. The fiber lumen 58 remains close to the center lumen 54 under one or more or all bending configurations such that the fiber 59 assumes the same shape or substantially the same shape of the elongate instrument 200 or the shaft of the elongate instrument 200. Any of the braids described therein may be positioned in any portion of the proximal or distal sections of the elongate instrument or along the entire length or substantially entire length of the elongate instrument.

The braid 56 and lumen 58 construct provides a mechanism or allows for a method for incorporating or integrating a fiber 59 in the wall of an elongate instrument 200 or shaft of the elongate instrument 200, such that: the fiber 59 is provided with an accurate and reliable radial positioning within the elongate instrument and has minimal twist; the fiber 59 assumes the same shape or substantially the same shape of the elongate instrument during elongate instrument bending; and/or the fiber 59 is free to float and is not impinged or minimally impinged during elongate instrument bending.

Tubes, liners, pipes or other support components may be incorporated into an elongate instrument in a symmetrical and balanced configuration. For example, tubes having 90 degree symmetry may be arranged in an elongate instrument to maintain uniform bending stiffness and provide ease in manufacturing.

In certain variations, where shape sensing fibers are incorporated into an elongate instrument in an unbalanced or nonsymmetrical configuration, additional fibers or "dummy fibers" may be introduced into the elongate instrument to create a more symmetric and uniform elongate instrument structure. Additional or "dummy" fibers may be added to the articulation or other section of the elongate instrument and they may be free floating.

FIG. 2B shows an elongate instrument 20 having a symmetrical arrangement of lumens 22. One or more shape sensing fibers 24 and "dummy fibers" are included in the lumens 22 of the elongate instrument 20. Optionally, additional fibers for providing a balanced and symmetric configuration could be shape sensing fibers. The additional shape sensing fibers may provide multiple sensing of the same shape and position, which may be used to reduce any error in shape sensing.

A free floating fiber may contribute negligible bending stiffness to an elongate instrument while providing no or minimal friction or binding between the fiber and lumen of the elongate instrument. Various coatings, e.g., polyimide coatings or other friction reducing compounds such as silicones and other lubrication, may be applied to lumens or fibers to reduce friction between a fiber and lumen. A polyimide coating may also reduce the overall diameter of a fiber so that the fiber may be easily fit into a wall of an elongate instrument, such as a Hansen vascular catheter NORTHSTAR™ which has been described in previously incorporated applications.

Various mechanical structures and materials, such as those discussed supra, may be incorporated into an elongate instrument to avoid or reduce twist of the elongate instrument out of an articulation plane and/or to maintain a longitudinally uniform bending stiffness through an articulation section of the elongate instrument so that there is a constant or consistent radius of curvature in the articulation section. Indeed, various structures and/or materials may be introduced into an elongate instrument to stiffen various parts of the elongate instrument to avoid or reduce twist and to maintain uniform bending stiffness.

Lumens in an elongate instrument may be spaced apart from control wires in any number of degrees or configurations. For example, referring back to FIG. 2B, the fiber lumens 22 are spaced apart from the control wires 26 by 45 degrees.

FIGS. 3A-3C show examples of elongate instruments 30 where the fiber 34 and fiber lumen 32 are placed at various positions at various degrees in relation to control wire 36.

Figure 4A:
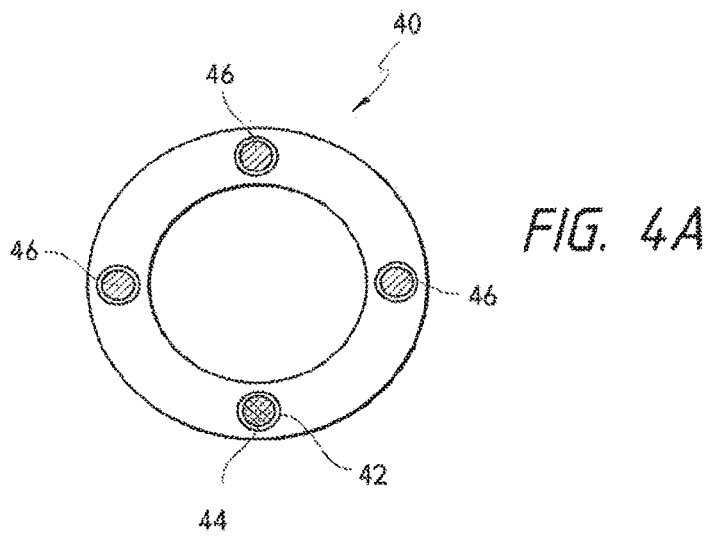
FIGS. 4A-4C illustrate cross sectional views of variations of elongate instruments having fibers placed at various positions in relation to several control wires.
Figure 4B:
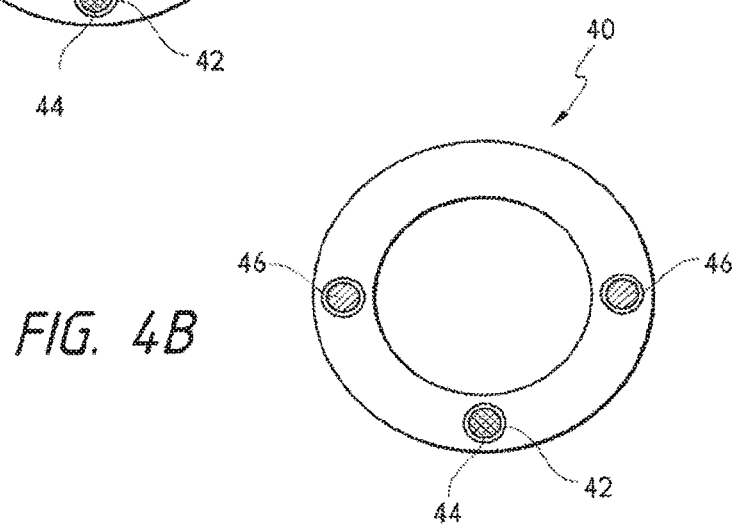
Figure 4C:
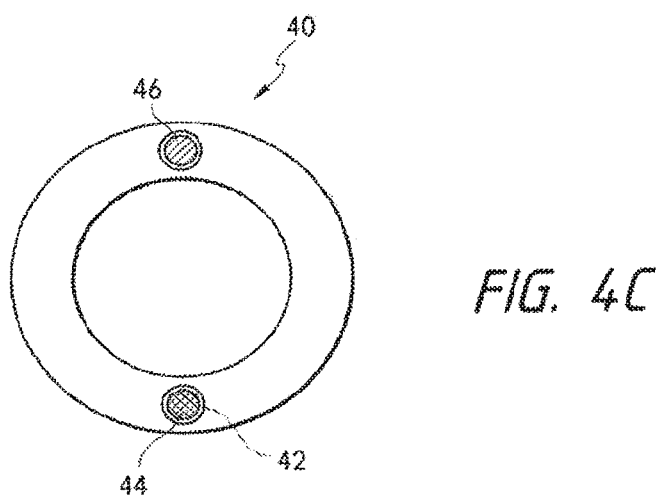

FIGS. 4A-4C show examples of elongate instruments 40 having varying numbers of control wires 46 with fiber 44 positioned in a fiber lumen 42, located in various positions in relation to the control wires 46.

In certain variations, an elongate instrument may have any combination of one or more control wires and one or more fibers. Any number of lumens of an elongate instrument may be populated with control wires and/or fibers and/or support components. For example, an elongate instrument having four lumens may have three lumens populated with control wires and one populated with a fiber. In certain variations, one or more fibers may be positioned in one or more lumens in a wall of an elongate instrument; for example, around the circumference of the elongate instrument. In other variations, one or more fibers may be positioned along a neutral axis of an elongate instrument, (e.g., along the center axis of the elongate instrument or the axis in which path length does not change or has negligible change during bending). In other variations, one or more fibers may be positioned along the outside of an elongate instrument. The fiber may be integrated into an elongate instrument in a manner such that it does not exceed the maximum strain tolerability of the fiber.

In certain variations, an elongate instrument may include a distal tip, distal end or other structures or materials configured to support at least a portion of a fiber distal end or fiber termination.

Figure 6A:
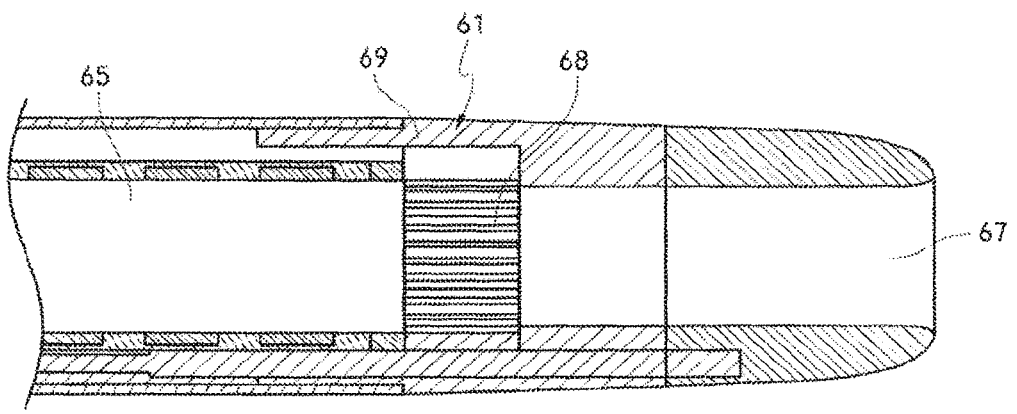
FIGS. 6A-6B illustrate a variation of a fiber termination integrated in the tip of an elongate instrument.
Figure 6B:
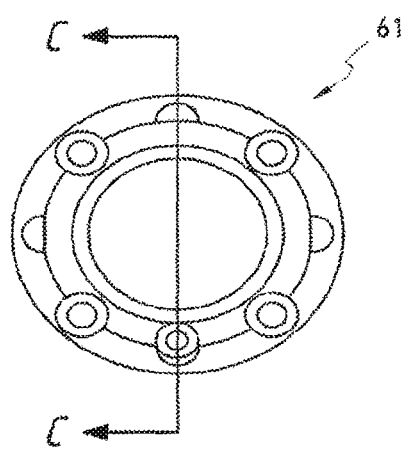

A distal tip of a fiber may include a termination attached thereto. FIGS. 6A and 6B (a cross sectional view) show one variation of a fiber distal end 65 integrated within an elongate instrument distal tip 61. A termination 67 is spliced at junction 68 onto the fiber distal end 65. The termination 67 may be made from a variety of materials having light absorptive properties, such that light travels into the termination 67 and fiber 65 and back reflection is reduced or eliminated (e.g., such that reflection does not disrupt shape sensing algorithms). For example, the termination 67 may be a piece of glass which is highly absorptive. The termination

67 may range in length, e.g., from about 1-3 mm. The termination 67 may have a diameter similar in size to the fiber 65 itself such that the termination 67 may be attached to the fiber 65 and loaded through a lumen of the elongate instrument along with the fiber 65.

Because the junction 68, joint, or splice area where the termination 67 is spliced onto the fiber distal end 65 may be weak or fragile, the elongate instrument may include a distal tip 61 or other structure or material to protect the junction 68, termination 67 and/or fiber distal end 65. The fiber termination 67 and/or junction 68 may be placed in the elongate instrument in a position or section that bends or articulates minimally or in a reduced manner and/or may be protected by the elongate instrument or other structure so that the termination 67 and/or junction 68 don't bend or have minimal bending, and are protected during articulation and use of the elongate instrument, e.g., when the elongate instrument is contacting or ramming into tissue or other structures.

The elongate instrument tip 61 may include a control ring 69 used to terminate control or pull wires at the distal tip of the elongate instrument as previously described. The control ring 69 may be notched and may allow the fiber 65 to extend along the control ring 69 and into the tip 61. The tip 61 and/or control ring 69 may include stainless still, nylon, or other materials that provide stiffness to the tip 61 and control ring 69 sufficient to support the termination 67 and reduce or eliminate lateral bending of the termination 67. Nylon may be melted onto the termination 67 to fix the fiber 65 and/or termination 67 to the distal end or tip 61 of the elongate instrument. The elongate instrument tip 61 may include a stiff or rigid section, e.g., about 2-3 mm in length, that is strong enough to house the splice/junction 68 and termination 67 and prevent them from being loaded with too much strain or strain beyond the maximum strain tolerability of the splice/junction 68, fiber distal end 65, or termination 67 portions. In certain variations stiff materials, such as Nylon or PEBAX 72D may be melted over the junction, termination and/or fiber, e.g., as shown in FIGS. 6A-B.

In certain variations various features that may reduce or eliminate breaking or bending of a fiber termination include the following. The elongate instrument tip may include a clear portion, made from a clear substance, e.g., clear nylon, that allows for visibility of the fiber through the wall of the elongate instrument tip. This helps preserve alignment or align the fiber and/or termination within the elongate instrument tip, during the fixing of the fiber and/or termination to the elongate instrument, e.g., during nylon or other material melt down. The stiff section of the elongate instrument tip, e.g., a stiff nylon section, may be increased or decreased in length to provide a length sufficient to protect the termination. A stiff or rigid sleeve, sheath, tube or cover, (e.g., made from 72D PEBAX, stainless steel, nylon, or polycarbonate) may be positioned or melted over at least portion of the distal section or tip of the elongate instrument, the stiff section of a spine, or the control ring to increase overall stiffness of the elongate instrument tip.

In certain variations, a rigid tube (e.g., stainless steel, nylon, or polycarbonate) may be positioned over the termination to protect the termination. The termination may be glued or otherwise fixed in a rigid tube which may be small enough to slide through a lumen of the elongate instrument. The termination and/or fiber and rigid tube may be slid through the lumen and fixed to the elongate instrument tip or to a nylon tip. Alternatively, the rigid tube may be integrated into the elongate instrument tip or control ring and the fiber and/or termination may be slid through the lumen of the elongate instrument and through the rigid tube and fixed to the elongate instrument by gluing or melting materials around the fiber. The length of the control ring may be modified or increased as necessary to extend beyond the termination to increase the length of the stiff section at the distal end or tip of the elongate instrument to protect the termination. Optionally a spine (e.g., nitinol spine) in the articulation section of the elongate instrument may be cut or designed such that at least a portion of the spine protects the termination and/or stiffens the elongate instrument. Optionally, stiff material, e.g., nylon, may be melted over the termination and/or junction section of the fiber for protection and to reduce strain. The elongate instrument tip or a feature attached to the termination or the termination may be designed in a variety of shapes, e.g., square, triangle, or have modified geometric features to provide strength.

In another variation, the elongate instrument tip may include light absorbing material (e.g., black materials such as black nylon) which may be positioned around the termination to reduce reflections at the tip of the fiber and elongate instrument. The light absorbing materials and other structures positioned in the elongate instrument or at the tip of the elongate instrument may improve or aid the optical properties required for fiber optic shape sensing.

In another variation, the fiber termination or junction may be coated and/or encapsulated to provide protection from fluid, water vapor, or vapor ingress. The distal end of a fiber, junction or the termination may be protected from moisture ingress in order to preserve the fiber's optical qualities. This may be accomplished by coating the termination and any fiber portion that may be stripped or spliced for attachment of the termination to the fiber with a coating material. Suitable coating materials may be thin to maintain the fiber diameter size at a size that is smaller than the size of the lumen in the elongate instrument in which the fiber may be positioned. The coating materials may also be conformal and able to resist or keep out moisture from the fiber. Such materials include, for example, polyimide dip/vapor deposition, parylene vapor deposition, urethane, and silicon. The fiber may be dip coated before insertion into a lumen. Encapsulation material could also be injected or melted from the open end of the lumen before an elongate instrument or catheter is tipped and the lumen end is sealed.

In certain variations an off the shelf fiber can be integrated into an elongate instrument, such as a catheter. The off the shelf fiber can include a bare fiber with a polyimide coating along the length of the fiber and a termination at its distal tip. The off the shelf fiber may be prepared to fulfill shape sensing requirements before or during integration of the fiber into an elongate instrument.

Figure 7:
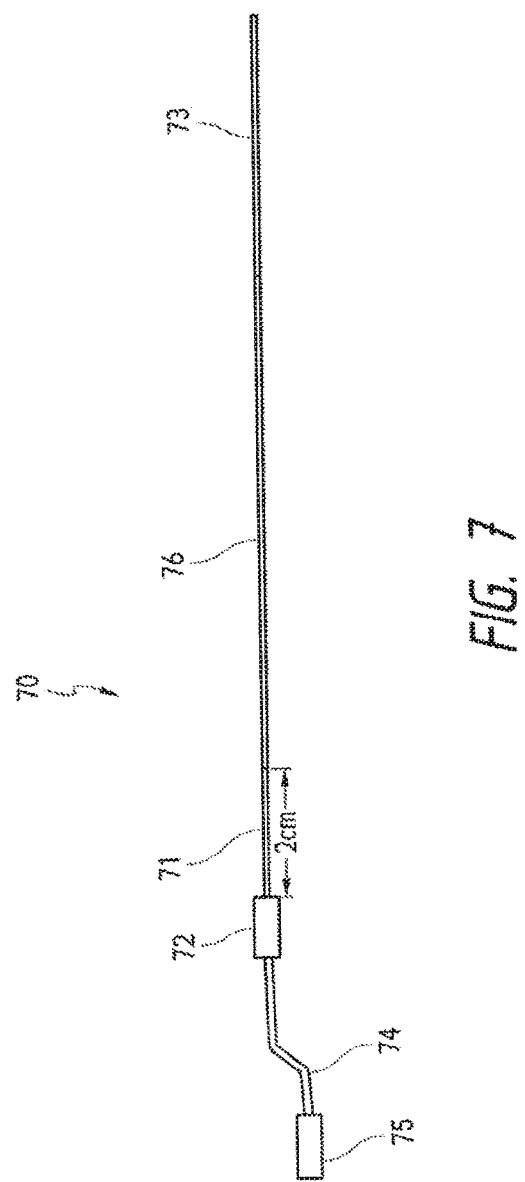
FIG. 7, illustrates a variation of a fiber having various accessories for fulfilling shape sensing requirements when integrated into an elongate instrument.

As shown in FIG. 7, which illustrates a variation of a fiber assembly 70 prior to integration within a catheter assembly, the fiber assembly may include various accessories or elements for fulfilling shape sensing requirements. A section 71 located near a proximal end of the off the shelf fiber 76 may be placed in a well toleranced straight track, hypotube or silica block or tube to provide a straight section 71. The straight section 71 may vary in length, e.g., the section may be about 2 to 4 cm long. The straight section 71 may be used to initialize algorithms. A strain relief 72 and/or jacket may be provided over a portion of the off the shelf fiber 76 proximal to the straight section 71. In certain variations, the strain relief 72 is provided at a proximal end of an off the shelf fiber 76, e.g., where the fiber exits an elongate instrument, providing a gradual exit of the fiber 76 from the elongate instrument. A polyimide tube 73 is provided at a distal end of a fiber 76. In one example, the polyimide tube may be continuous or extend to the proximal end of the fiber and act as the strain relief. Protective tubing 74 and/or a connector 75 may be placed on the most proximal end of the off the shelf fiber 76.

A fiber has a minimum bend radius and may be fragile. As such, it may be desirable to minimize the number of fiber preparation steps performed after the fiber is incorporated or integrated into a catheter or elongate instrument. For example, preparation of the fiber's proximal end may be performed before integration of the fiber into the catheter. Calibration of a fiber may be performed before a pull tube is glued or affixed to a fiber or before the fiber is integrated or incorporated into a catheter or other elongate instrument.

Various processes and methods for integrating a fiber into an elongate instrument, such as a catheter, are described herein.

In alternative variations, a method or process for integrating or incorporating a fiber into a catheter may include the following. To avoid pushing the fragile fiber termination or section through the lumen of a catheter, the termination section of the fiber assembly may be affixed or glued into a long pull tube, e.g., a long polyimide pull tube 75 as illustrated in FIG. 7. The pull tube may be constructed for example from a polyimide tube or tube made from another similar material. Optionally, the pull tube may include a mandrel to stiffen the tube for pushing. The pull tube which is fixably coupled to the fiber is then pushed from the proximal end of the catheter through one of the catheter lumens to the distal end of the catheter. Once the pull tube is pushed far enough through the lumen so that it protrudes past the distal tip of the catheter, the pull tube may be pulled from the distal end until the fiber can be positioned as desired. In one variation the termination junction on the fiber assembly can be positioned in the middle of the control ring. The pull tube can then be cut off of the fiber assembly, and the termination can be melted and embedded into the catheter tip with Pebax or comparable materials in the same manner previously described.

Alternate materials and constructions may be utilized for a pull tube. In one variation the fiber assembly termination can be affixed to mandril which can be glued in a shorter pull tube. In another variation, the fiber assembly termination may be affixed or glued inside a stainless steel tube (e.g., the tube being about 3-6 mm in length). A pull tube and/or wire may then be affixed or glued to the stainless steel tube and the pull tube or wire is then pushed or pulled through a lumen of the catheter.

FIGS. 8A-D show a variation of a process or method for integrating a fiber assembly such as that illustrated in FIG. 7 into an elongate instrument or elongate instrument assembly, such as a robotic catheter assembly. FIGS. 8A-8D shows a robotic catheter assembly 80 having a catheter 81 with a lumen 84 for a fiber, a splayer assembly 82, pulleys 83 and a registration fixture 86, e.g., a shape plate or service loop plate, attached to the splayer 82. The catheter 81 can include control wires fixed near the distal tip of the catheter to a control ring and additional lumens such as working lumens. The catheter 81 can be coupled to the splayer assembly 82 which contains pulleys or spindles that actuate the control wires which run from the splayer 82 to the distal tip 87 of the catheter 81 as described in detail in previously incorporated patent applications. Coupled to the splayer 82 is a registration fixture configured with a groove for receiving a service loop. The registration fixture can be sealed with a fixture lid. In certain variations, registration fixtures may be designed to prevent a fiber from bending below its minimum bend radius. A registration fixture may also be designed to hold, accommodate or provide a service loop along the fiber.

Providing a fiber with extra length or a service loop (e.g., the service loop may have a length of about 1-2 cm or longer) is one mechanism for absorbing a length change in the fiber when the fiber is positioned off of the neutral axis of an elongate instrument. For example, a fiber length change may occur when a catheter, and the fiber integrated therein, is bent or articulated in various degrees of freedom. If a fiber is anchored to an elongate instrument off the neutral or center axis of the elongate instrument, as the elongate instrument is bent, the fiber may take a different path than the elongate instrument. A service loop may accommodate a fiber length change due to axial compression or bending of the elongate instrument or due to manufacturing tolerances of the elongate instrument. A service loop may provide the fiber with extra length such that the fiber may slide in and out of the elongate instrument, as the service loop absorbs the length change. As an elongate instrument bends, the path length of the fiber may change and the amount of fiber present within the elongate instrument may change. A service loop may absorb these length changes. A service loop may allow an elongate instrument to be bent without adding strain to an integrated fiber, e.g., integrated in the walls of the elongate instrument. A service loop may allow a fiber to lengthen or contract within an elongate instrument without exceeding its minimum bend radius. A service loop may have various shapes and configurations and may be positioned anywhere along a fiber, e.g., anywhere along a fiber between a fixed distal section of the fiber (e.g., fixed to a distal section of an elongate instrument) and/or a fixed proximal section of the fiber (e.g., fixed to a proximal section of an elongate instrument or other structure associated with the elongate instrument). A service loop may be free floating and/or positioned in a groove or track or on a surface of a registration fixture.

In certain variations, a registration fixture may be positioned in a known orientation including but not limited to vertically or horizontally relative to a splayer or other structure associated with a catheter and the registration fixture may have a variety of shapes and configurations. The registration fixture may include a groove or track having a variety of shapes for receiving a fiber or service loop of the fiber. The groove or track may allow the service loop to spiral in the left hand or right hand direction or take on a configuration or shape similar to a bird's eye, a jog shape or other curve.

Various examples of registration fixtures are described herein. However, a registration fixture may be any structure on which or within which a fiber, elongate instrument, splayer or other structure may be positioned, coupled to, affixed to or otherwise held in various known or unknown configurations to register the coordinate system of a fiber with the coordinate system of an elongate instrument, splayer or other structure. In certain variations, in use, a register fixture may be located or positioned in any orientation or configuration (e.g., parallel or perpendicular) relative to an elongate instrument, splayer or other structure. In certain variations, the location of the registration fixture relative to the elongate instrument or structure of interest may be known. A registration fixture may or may not be attached or coupled to an elongate instrument. In certain variations, the registration fixture may be attached to a splayer or it may not be attached to an elongate instrument, e.g., a fixture used for in-factory registration or calibration.

Various registration fixtures are described herein.

Figures 9A, 9B:
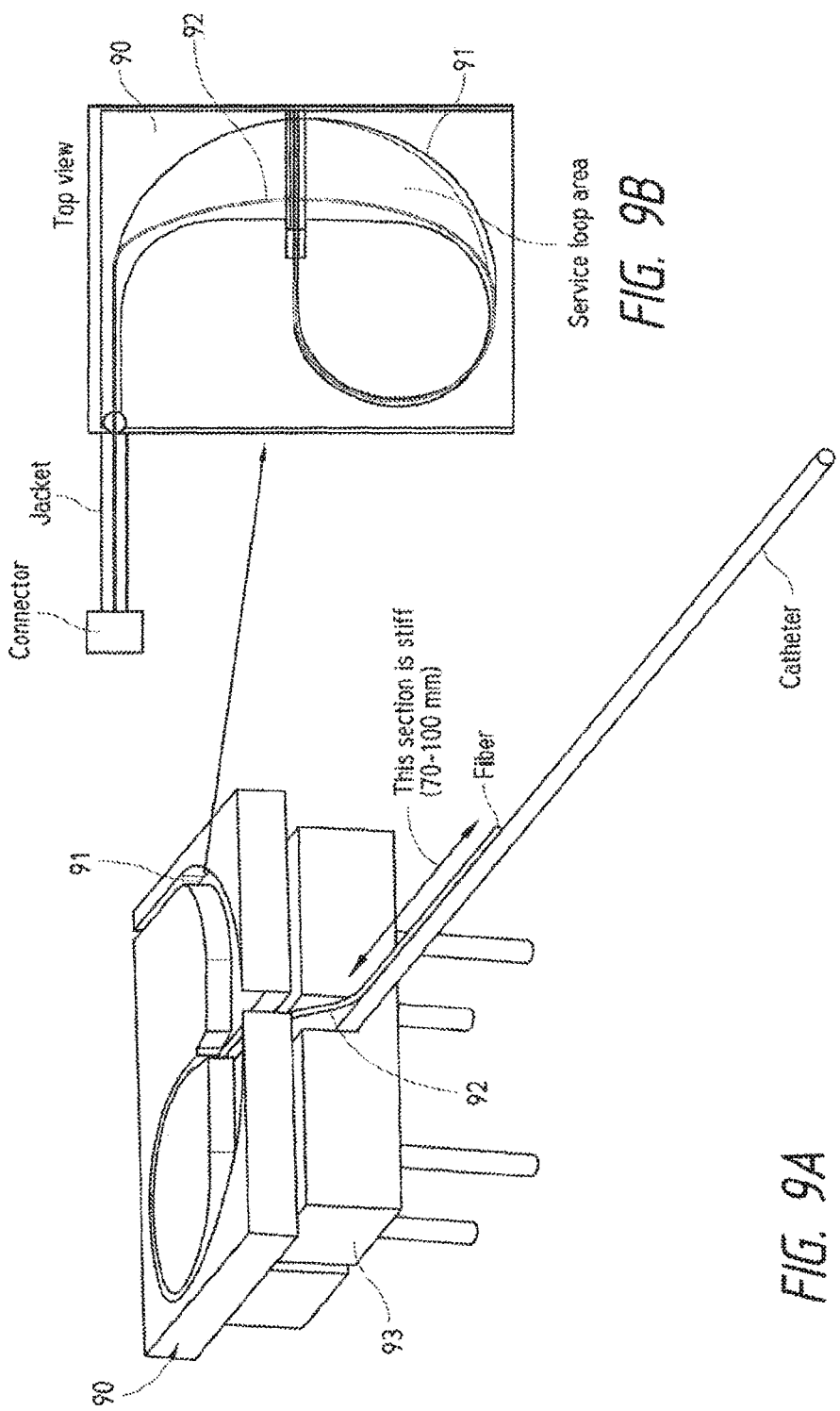
FIG. 9A shows a variation of a registration fixture positioned on a catheter assembly having a groove for positioning a fiber in a bird's eye shape.
FIG. 9B shows a top view of the registration fixture of FIG. 9A.

FIGS. 9A-9B show one example of a registration plate 90 having a groove 91 for positioning a fiber 92 (e.g., a service loop of a fiber), where the registration plate 90 is positioned horizontal to the splayer 93 in an out of plane splayer configuration.

Figure 10B:
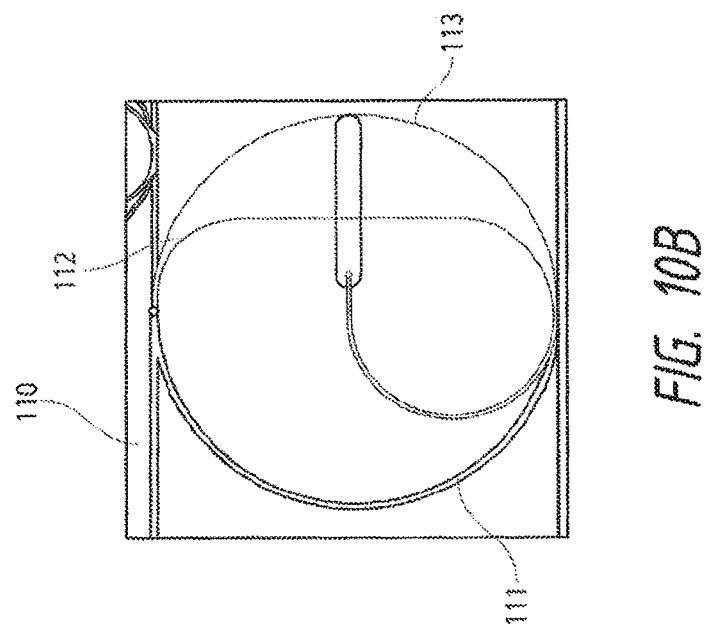
FIGS. 10A-10C show top views of variations of registration fixtures for positioning a fiber in various shapes or configurations.
Figure 10A:
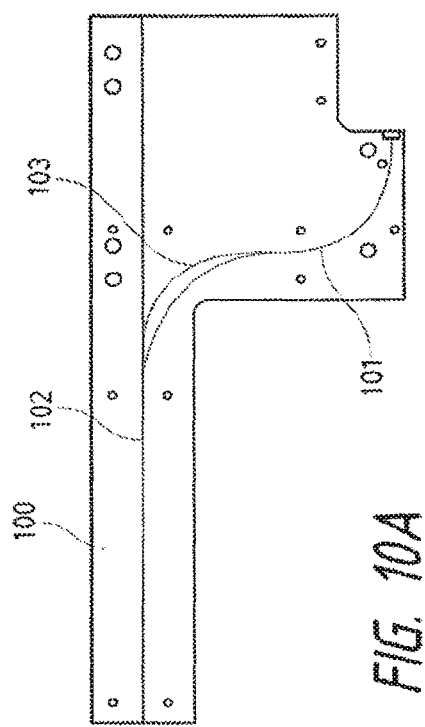

FIG. 10A-10B show variations of registration plates for positioning a fiber in various shapes or configurations.

Figure 10C:
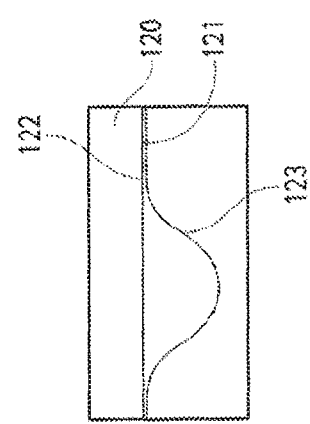

FIG. 10A shows one example of a plate 100 having a groove 101 for positioning a service loop 103 of a fiber 102 in a bird's eye shape. FIG. 10B shows one example of a registration plate 110 having a groove 111 for positioning a service loop 113 of a fiber 112 in a loop shape. FIG. 10C shows one example of a registration plate 126 having a groove 121 for positioning a service loop 123 of a fiber 122 in a jog shape.

Steps for manufacturing a catheter and integrating the fiber into the catheter assembly as shown in FIG. 8A will now be described. It should be noted that alternative and additional steps which may be utilized have been described in detail in applications previously incorporated by reference which are not included herein for clarity. Initially the catheter can be manufactured with methods either well known in the art or previously described providing several lumens including but not limited to the fiber lumen, the working lumen, and lumens for the control wires with the control wires installed and affixed to a control ring near the distal tip of the catheter. Nylon, PEBAX or other similar materials may be melted on the distal tip of the catheter to create a soft tip. The fiber lumen can be kept open or patent when the soft distal tip is created. The catheter can then be coated and the catheter control wires can be installed onto the splayer spindles. The registration plate can be installed onto the splayer with the registration plate removed to prepare for fiber assembly integration.

Figure 15:
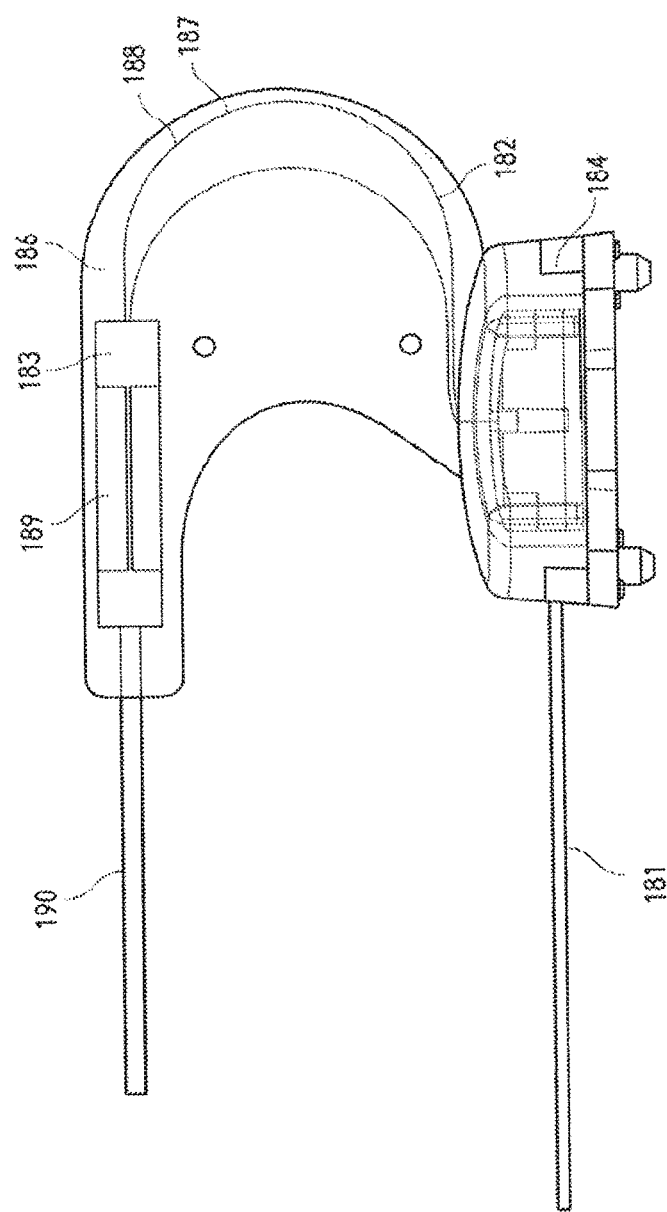
FIG. 15 shows another variation of a registration fixture for receiving fiber slack.

FIG. 15 shows, another variation of a registration fixture 186 for receiving fiber slack or a service loop 188. The registration fixture 186 may be in the form of a plate having a track 187 that guides the fiber 182 from the proximal end of the catheter 181 (without exceeding the minimum bend radius) into a service loop 188 that allows the fiber 182 to have some predetermined amount of travel. The registration fixture 186 may be fixed to a splayer 183. Because it can be difficult to consistently fix the fiber length during integration of the fiber 182 within the registration fixture 186, the proximal end of the fiber 182 can be fixed to an anchor slide 189 which can be a block or other structure made from silica, quartz, glass or other similar material. The anchor slide 189 may reside or be positioned in a pocket 183 on the registration fixture 186, such that the anchor slide 189 is capable of being slid back and forth within the pocket 183 during installation to accommodate different lengths of fiber 182. The anchor slide 189 and the pocket 183 may be configured in rectangular shapes and can be sized such that the anchor slide 189 is prevented from any vertical, yaw, or pitch movement while still providing axial movement. In certain variations, during integration, the anchor slide 189 may be positioned within the pocket 183 to fix a desired length of the fiber 182, and then glued into position. Proximal to the fiber anchor slide 189 may be a strain relief 190 leading out of the fixture 186 which provides strain relief and protection for the fiber 182 until it reaches the next component.

The registration fixture 186 provides a method or mechanism for managing fiber slack at a proximal end of catheter; such that: the minimum bend radius of the fiber is not exceeded; the fiber is fixed on the proximal end, floating on the distal end, and the fiber is allowed to travel some predetermined distance; the fiber is supported after exiting the proximal end; the fiber is held in some position that allows for shape registration; and/or the proximal end anchor of the fiber can be adjusted to accommodate for tolerance stack up.

FIGS. 8B-8D illustrate one variation of a method of integrating a fiber assembly 85 (e.g., similar to the fiber assembly shown in FIG. 7), into the catheter assembly 80 illustrated in FIG. 8A. Before the fiber assembly 85 is slid or inserted into the catheter fiber lumen, the distal tip or termination of the fiber assembly 85 may be affixed to a pull tube as previously described. As shown in FIG. 8B, the pull tube attached to the fiber assembly 85 may be fed through the registration fixture and the fiber assembly 85 can then be inserted into the proximal end of the catheter fiber lumen 84, pulled through the fiber lumen 84 of the catheter, and pulled through the catheter distal tip 87 in the same manner previously described. As shown in FIG. 8C, any excess polyimide pull tube is cut off and nylon may be melted down to secure the fiber 85 to the catheter 81. PEBAX may be shaped on to the catheter to form a soft tip. As shown in FIG. 8D, on the proximal splayer side of the fiber 85, the fiber 85 may be wrapped into a service loop 88 and the protective tube 74 or polyimide and/or strain relief 72 sections on the fiber may be affixed or glued into place, e.g., on the registration fixture 86 allowing the fiber 85 to remain free to float or slide within the catheter fiber lumen. The registration fixture 86 may then be closed and secured once the fiber 85 is in place. In certain variations, a connector 75 used with the fiber may be pigtailed or incorporated into the splayer or may remain bare.

In another variation, a pull tube may not be necessary if the fiber termination can become more robust due to a change in materials, providing a pushable termination. The fiber assembly can remain bare and can be installed without the use of a pull tube. For the bare fiber assembly, a lid, cap, or short tube may be placed over the fiber distal end or termination to protect the termination during installation of the fiber assembly into the catheter assembly. In another example, a termination of attenuative glass may be fused to a fiber tip. The fiber/glass termination may be dip coated in a thin layer of polyimide. If the fiber is fixtured or positioned such that it is straight and does not collide forcefully with other components in the catheter, the fiber may be pushed through the catheter and embedded in nylon or another support structure, such as those described for the pullable termination, at the tip of the catheter A variation of a method for integrating a shape sensing fiber in an elongate instrument may include inserting the fiber into a lumen of the elongate instrument, wherein the elongate instrument has a support component positioned therein for maintaining patency of the lumen during articulation of the elongate instrument; and fixing a distal end of the fiber at a distal end of the elongate instrument, wherein the fiber remains free to slide or float within the lumen of the elongate instrument.

Figure 16:
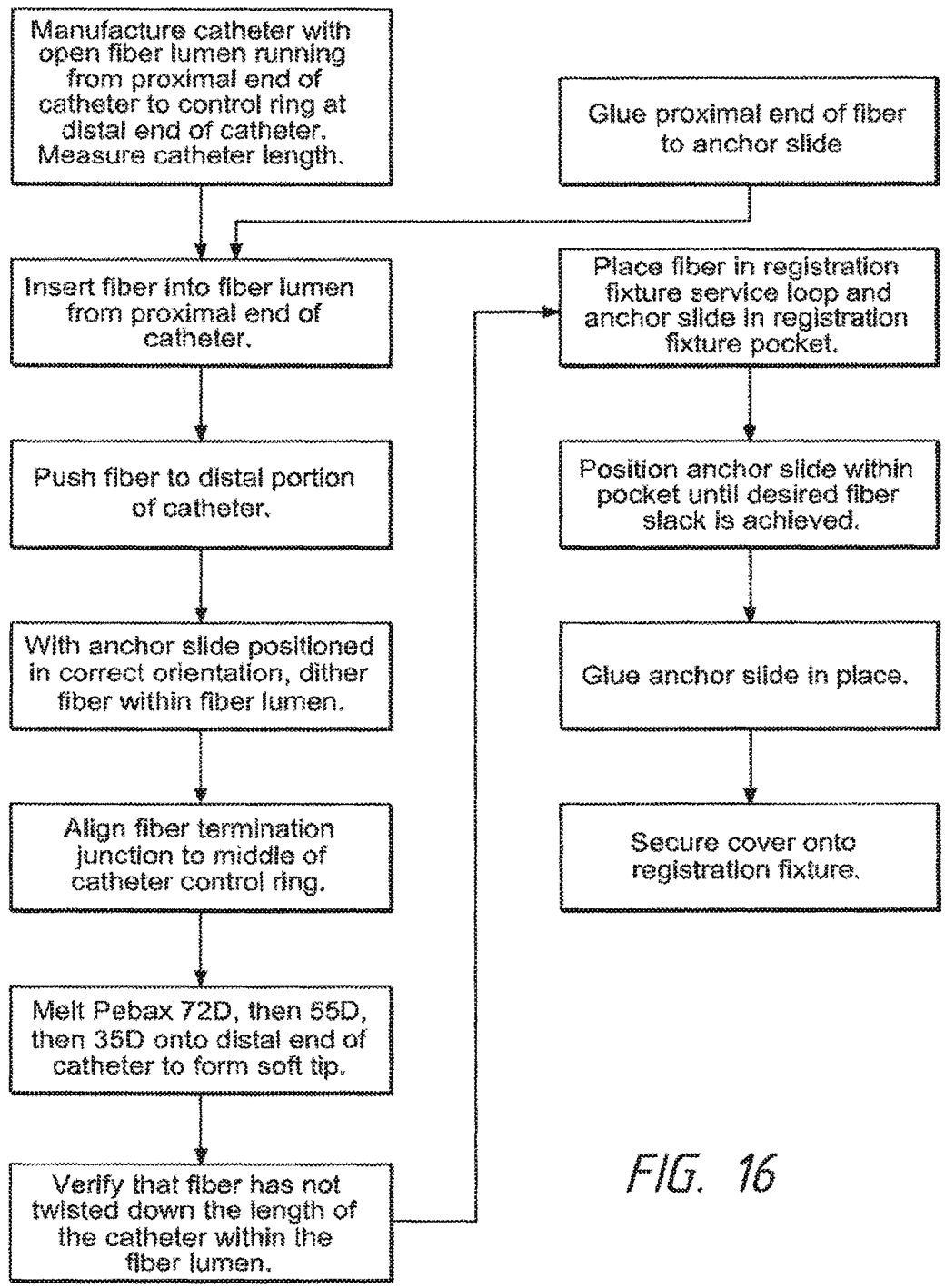
FIG. 16 shows a flow chart for a variation of a method of integrating a fiber into an elongate instrument.

FIG. 16 shows a flow chart for one variation of a method of integrating a fiber into an elongate instrument. Referring to FIG. 16 (and FIG. 15 which illustrates the proximal end of the catheter 181 and fiber 182), a variation of a process for integrating the fiber 182 into the catheter 181 is shown including one or more of the following steps. A catheter shaft 181 is made having an open fiber lumen for the fiber 182 in a manner as previously described. The catheter 181 is integrated into the splayer 183 also as previously described. The fiber 182, e.g., an off the shelf fiber, is prepared by fixing or gluing the proximal end of the fiber 182 to the anchor slide 189. The distal end of the fiber (not shown) can then be slid into the fiber lumen from the proximal end of the catheter 181 and pushed until the distal tip of the fiber 182 reaches a distal section of the catheter 181. The anchor slide 189 on the proximal end of the fiber 182 remains outside the proximal end of the catheter 181 near the splayer 183. With the anchor slide 189 positioned in a correct orientation using for example a fixture (not shown) which holds the anchor slide 189 in a fixed position, the fiber 182 is dithered or slid in a back and forth motion within the fiber lumen to break any friction between the fiber 182 and the fiber lumen wall, allowing the fiber 182 to resolve any twist it may have incurred during insert into the fiber lumen. The distal tip of the fiber 182 can then be properly aligned with respect to the catheter 181, e.g., the termination junction is positioned in the middle of a control ring and Pebax 72D, 55D, and 35D (or like materials) are melted onto the distal end of the catheter 181 to form a soft tip at the distal end of the catheter 181. Alternatively or additionally, nylon may be melted to the termination to secure the termination to the catheter tip. This process results in the distal end of the fiber 182, including the entire termination, being embedded inside the catheter tip.

A verification that the fiber 182 is not twisted can then be performed by either placing the catheter 181 in a known position and monitoring shape data from the fiber 182 to ensure the readings are accurate or by using a fixture to ensure no fiber twist. The proximal section of the fiber 182 which protrudes from the proximal end of the catheter 181 can then be placed into the service loop 188 in the registration fixture 186 and the anchor slide 189 on the proximal end of the fiber 182 can be placed into the pocket 184 of the registration fixture 186. The anchoring slide 189 is free to slide in the axial direction of the fiber 182 within the pocket 184. Thus anchoring slide 189 is adjusted within the pocket 184 until the desired fiber slack within the service loop 188 is obtained. Once in a desired position, the anchor slide 189 can be fixed, for example glued into place. A cover can be placed on the registration fixture 186 to protect and secure the fiber 182 within the service loop 188 and pocket 184.

In another variation, the fiber lumen at the distal control ring can be skived away such that the fiber is clearly visible once inserted. Outer plastic material that has flowed over the control ring can be cut away visually exposing the fiber. This method can allow the fiber to be aligned more accurately. Once aligned, a small amount of fast-curing adhesive can be applied to fill up the skive and provide a rigid, protective, encapsulation around the fiber termination. Various durometers of PEBAX, including but not limited to PEBAX 72D, 55D, and 35D, can then be melted onto the distal end of the catheter to form the catheter soft tip fully embedding and securing the fiber termination within the catheter tip. The fast curing adhesive bond can allow the catheter and fiber assembly to be handled before forming the catheter tip without the risk of misaligning the fiber. Indeed, a catheter or other elongate instrument tip may be encapsulated with PEBAX or other similar material.

In any of the variations described herein, fixturing or jigging may be built to more precisely align the termination splice or junction with a support structure in the catheter tip. Accurate or precise alignment may be important because the splice or junction may be more delicate and fragile than the surrounding structures, e.g., the fiber itself or the termination, e.g., made from glass.

In another variation, a fiber may be incorporated or integrated into a catheter before splayering is performed. The fiber may be placed in a protective enclosure during the final steps of the process and/or splayering.

Figure 17A:
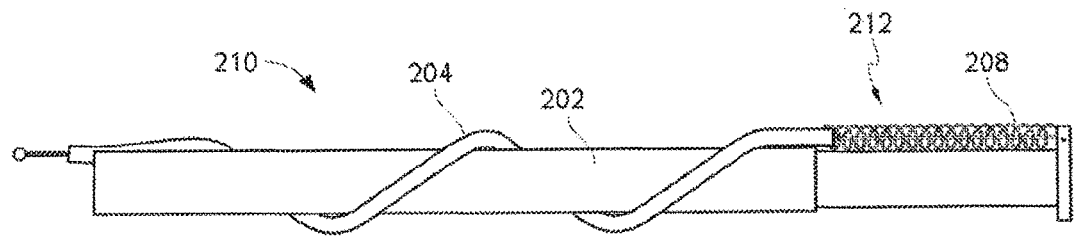
FIGS. 17A-17B show a variation of an elongate instrument having a fiber wrapped around at least a portion of the elongate instrument.
Figure 17B:
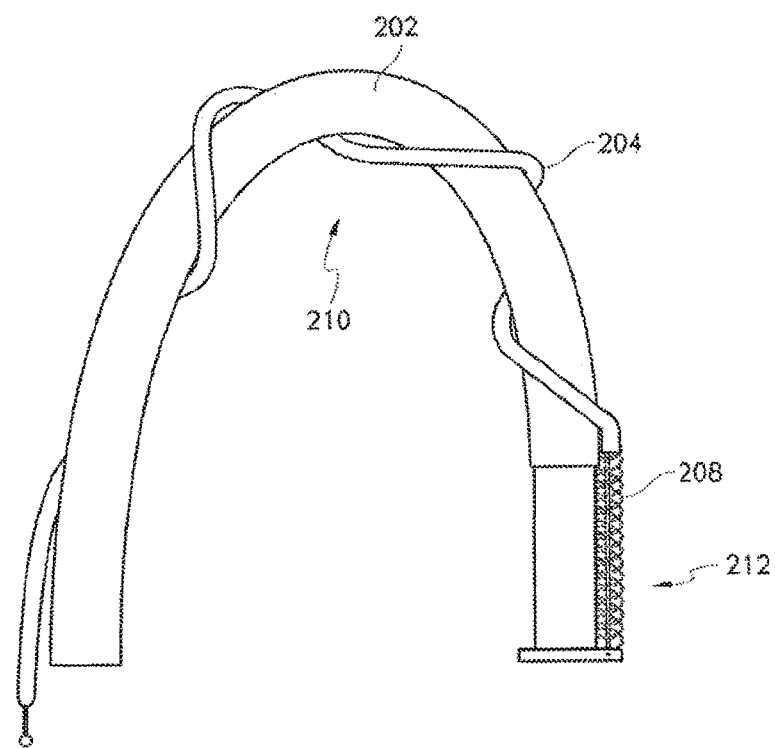

In other variations, other mechanisms may be provided for eliminating the effects of differing strains on varying surfaces of a fiber. These other mechanisms may or may not involve the use of a service loop. In one variation shown in FIGS. 17A-17B, a fiber 204 may be wrapped around an elongate instrument 202, spiraling the fiber 204 around the elongate instrument 202 such that the differing strains or bends on the inside or outside or different surfaces of the fiber 204 cancel each other out. FIG. 17A displays the elongate instrument 202 in a straight configuration and 17B displays the elongate instrument 202 in a bent configuration. In this variation, the fiber 204 can be wrapped around the elongate instrument 202 over a proximal section 210 and then fed into a coil lumen 208 in a distal section 212. Sliding or floating the fiber within the elongate instrument may or may not be performed in such a variation.

In another variation, a fiber may be positioned along the neutral bending axis of a elongate instrument, e.g., a catheter, bronchoscope, or endoscope. The neutral bending axis an imaginary line that runs through any structure, which is not subjected to strain when the structure is subjected to a bend along its length. Since the neutral axis is not axially strained during bending, any material, for example a fiber, that is positioned along this line will not compress or expand during the bending of the structure. Thus positioning a fiber along the neutral bending axis of an elongate instrument would minimize the amount of strain experienced by the fiber. The fiber may be glued, imbedded or affixed to the elongate instrument along the neutral axis while avoiding breakage due to bending because of minima strain experienced by the fiber along the neutral axis. In certain variations, a fiber may be positioned or integrated anywhere within or on a surface of an elongate instrument. For example, a fiber may be positioned along a neutral bending axis of an elongate instrument, within a wall of an elongate instrument or on an outer surface of an elongate instrument. Floating the fiber and providing a service loop may or may not be required.

In another variation, the neutral bending axis of an elongate instrument may be altered by modifying the structure of the elongate instrument. For example, the neutral bending axis of the elongate instrument may be mechanically shifted to coincide with the center of the fiber. An elongate instrument, such as a catheter, may be constructed in such a way that the neutral bending axis of the shaft is not directly along the center of the catheter cross section. The neutral bending axis of a catheter may be shifted by intentionally adding a single or a series of axially stiff components, e.g., a hypodermic tube, along the length of the catheter or by integrating such components into a wall of the catheter. The inclusion of these stiff members will govern the location of the shaft's neutral bending axis and shift it relative to the structure's cross section center. The catheter may or may not have a central working lumen.

In one variation, in order to minimize or eliminate the strain applied to a shape sensing fiber, an axially stiff lumen, such as a hypodermic tube, may be incorporated into an elongate instrument or catheter shaft. This stiff lumen will now govern the neutral axis of the structure. If the fiber resides inside this lumen, it can be concluded that the fiber will not be subjected to any axial strain due to the bending of the structure. This fiber integration approach will allow for the fiber to not need a service loop at the proximal end of the catheter since it will not need to compensate for its overall length inside the catheter.

In certain variations, an elongate instrument configured to support the integration of a shape sensing fiber therein may be provided. The elongate instrument may include a central working lumen, a fiber lumen positioned along the neutral axis of bending of the elongate instrument, and one or more axially stiff components integrated in a wall of the elongate instrument. The axially stiff component may be in the form of a hypodermic tube. Optionally, the elongate instrument may not include a central working lumen.

Registration of a Fiber Integrated in an Elongate Instrument

Various mechanisms and methods for registering a fiber to an elongate instrument, to a splayer, component, fixture, or other structure which may or may not be coupled to or associated with an elongate instrument, or to other structures or devices are provided herein. In registration, the objective is to relate the coordinate system of the fiber to the coordinate system of the instrument of interest; this involves relating the x, y, z, position and orientation of the two coordinate system (all 6 degrees of freedom). Registration may involve the use of certain mechanical registration structures (e.g., structures that are meaningful to an elongate instrument) and/or alignment algorithms. Registration may also involve other steps such as locating the tip or other points of interest of the fiber and their orientation with relation to the instrument. These pieces of information (for instance the orientation and location of the tip), can be used for such applications such as instinctive driving described in detail in applications previously incorporated by reference. In certain variations, a coordinate system of a shape sensing fiber may be registered with an elongate instrument, catheter, splayer or other associated structures through the use of mechanical structure and/or algorithms. In certain variations, registration may allow a shape sensing fiber to be used in an instrument such as a catheter for localization, e.g., particular, instinctive, driving, shape feedback, and positional driving.

Methods and apparatus for registration or calibration of a fiber coordinate system to a robotic catheter assembly coordinate system will be described herein. It should be understood that similar methods and apparatus may be used for registration of a fiber with any system, for example any flexible elongate member including but not limited to manual catheters, endoscopes, bronchoscopes, or guide wires as well as any system with rigid linkages.

Figure 11:
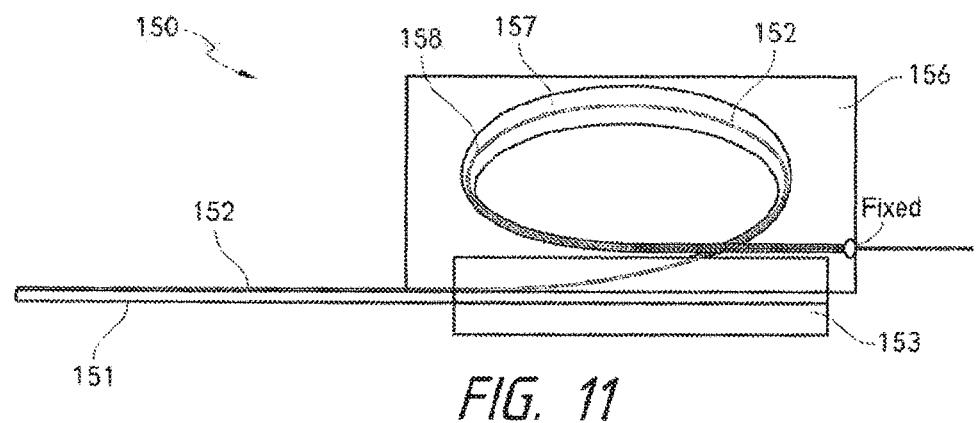
FIGS. 11-12 show a variation of a registration fixture for registering a shape sensing fiber to an elongate instrument
Figure 12:
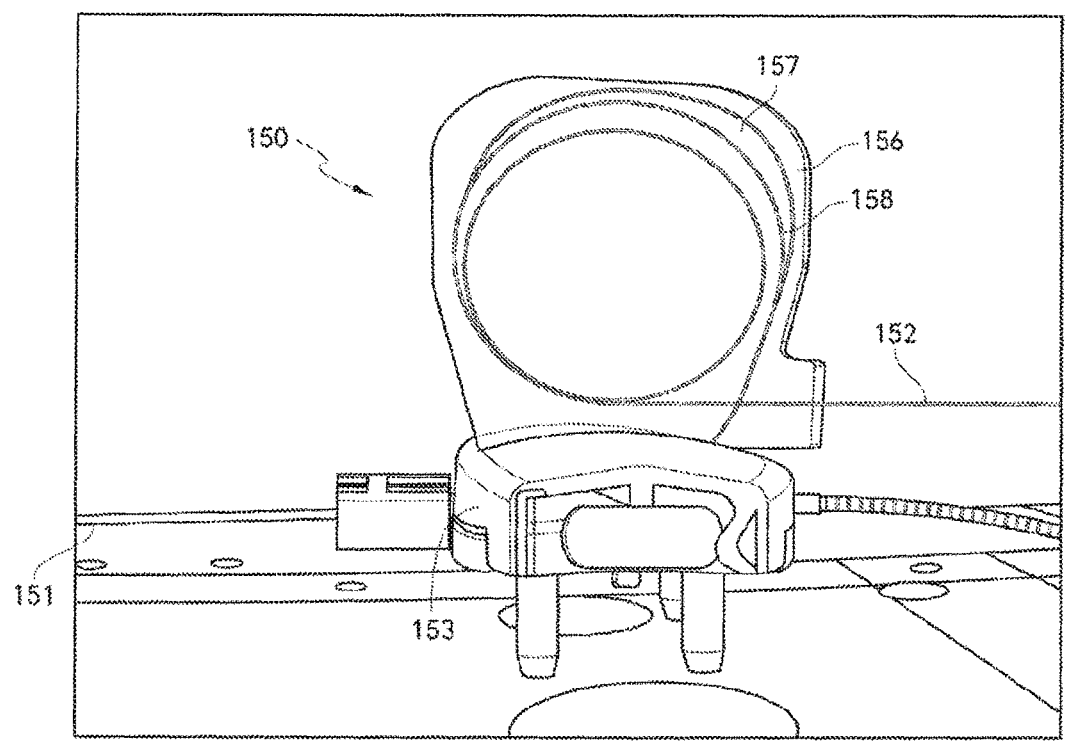

FIGS. 11 and 12 illustrate an example of a catheter assembly 150 with an integrated fiber 152. As previously described in detail, the fiber can be fixed to the distal tip of the catheter 151, run down the length of a lumen within the catheter, and be integrated or positioned into components of the splayer 153 or a structure associated with the splayer. The fiber 152 can be fixed in six degrees of freedom, less than 6 degrees of freedom or no degrees of freedom at its proximal end or origin to the splayer 153 or a structure fixed to the splayer, e.g., a registration fixture 156.

In order to register a fiber coordinate system to a catheter coordinate system, it may be desirable to use a full fiber length registration method including placing the entire or substantially the entire catheter assembly including the splayer and catheter with integrated fiber in known positions and orientations in a full fiber length registration fixture (e.g., a slide or plate or other structure) and then collecting data from fiber sensors within the fiber. The data collected from this process is used to calculate a transform or transformation matrix between the fiber coordinates and the catheter or splayer coordinates, which are physically tied to the registration fixture. The origin of the fiber coordinate system may be on the partial fiber length registration fixture (which may be affixed to the splayer) and the location of the partial fiber length registration fixture is determined through this registration process.

Also, the location of the fiber within the catheter may be determined. The orientation in roll and/or insert of the fiber distal tip glued or affixed within the catheter distal tip may be determined. The fiber includes a local coordinate system and the fiber can provide the location of the fiber tip. Registration provides the location of the catheter relative to the fiber.

Registration using the full fiber length registration method, which may use the entire or substantially the entire length of the fiber, can be used in one variation where an origin or proximal section of a fiber may or may not be fixed to the splayer or a partial fiber length registration fixture. The transformation of or the transformation matrix from the fiber coordinate system to the physical coordinate system of the splayer or catheter can be determined by placing the catheter with integrated fiber and splayer in a well machined and toleranced full fiber length registration fixture having known mechanical structures (such as curves, points, or grooves).

Figure 13:
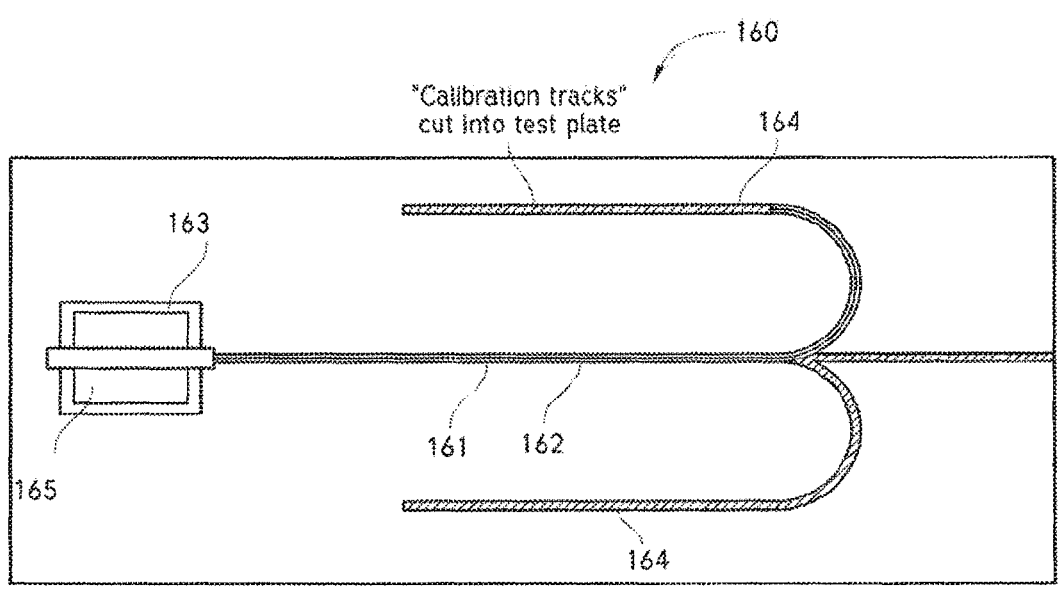
FIG. 13 shows a variation of a registration fixture for registering a shape sensing fiber to an elongate instrument.

FIG. 13 shows a variation of a full fiber length registration fixture 160 for registering a shape sensing fiber 162 to a catheter 162. In particular, FIG. 13 shows a full fiber length registration fixture 160 for registering or calibrating shape using the entire or substantially the entire fiber 162 length. The full fiber length registration fixture 160 may have a splayer holder 163 as well as several grooves 164 including two grooves each with a 180 degree u-turn shape and a straight line groove. The splayer holder 165, grooves 164 and the full fiber length registration fixture 160 may be manufactured or cut out of glass or another similar material as a single unit resulting in tight tolerances as small as +/−0.001" for example resulting in minimal angular error and accurate known location of the grooves 164 relative to the splayer holder 163. The splayer holder 163 is configured to serve as a receptacle for receiving or attaching to the base of a splayer 165 while the grooves 164 provide for several various shapes in which the entire or substantially the entire shape of the catheter 161 with fiber 162 may be fit. Where there is a systematic shape sensing error, averaging the registration from the different shapes to determine a final registration may result in a more accurate transformation matrix.

Various shapes for performing full fiber length registration on the full fiber length registration fixture may be utilized, e.g., shapes that extend in the forward, left, right, up, and/or down directions. The longer the lever arm or length of the fiber for calibration, the smaller the angular error should be. The accuracy of the registration procedure may depend on the accuracy of measurements that may be obtained and/or the fixture type or design.

In an alternative variation, the full fiber length registration fixture can include a splayer holder and instead of grooves can include various points placed in known locations relative to the splayer holder. With this full fiber length registration fixture, the tip of the catheter may be touched to the known points to calculate a transformation matrix between the fiber coordinate system and a physical coordinate system of the splayer or elongate instrument.

As described full fiber length registration involves registration and/or calibration on the entire or substantially entire length of a shape sensing fiber. When using full fiber length registration, assuming the shape sensing has close to zero error, having a long lever arm may allow for a more accurate calculation of the coordinate system transformation and provide a more accurate registration. Full fiber length registration may not require the use of fiducials in the mechanical registration fixture or structure if the fiber origin or a section at the fiber proximal end is fixed with the tolerance needed to maintain alignment out of the factory and is not able to rotate or change position once it is registered or calibrated.

However, in certain applications, the fiber origin may not be fixed with the tolerance needed to maintain alignment out of the factory. Also, the natural twist or roll during full fiber registration of the catheter in which the fiber is integrated may also provide a source of error during registration. If the elongate instrument twists while positioned in the grooves in the registration plate, the determined location of the fiber may no longer be accurate as the error lies within the diameter of the elongate instrument. In certain variations, an elongate instrument may not twist and/or the elongate instrument may have a diameter of about 2 mm (such as a vascular catheter) where 2 mm may be on the order of a shape sensing error such that any error due to twist is negligible. Thus additional registration or calibration beyond full fiber length registration may be necessary.

An alternative or additional registration or calibration method includes partial fiber length registration, e.g., at the proximal end of the fiber, or at least a partial length of the fiber registration. Partial fiber length registration can involve registration on any partial length or section of a shape sensing fiber. In certain variations, at least a section or portion of a fiber may be fixed or grounded relative to an elongate instrument or to a structure associated with an elongate instrument, such as a partial fiber length registration fixture (e.g., a plate or slide) or the splayer, such that the fiber may be registered to the elongate instrument or to a structure associated with the elongate instrument and the fiber may provide shape sensing or measuring of the elongate instrument. Partial fiber length registration may be performed in an ongoing manner, e.g., during use of an elongate instrument. Optionally, partial fiber length registration may be performed where no portion of the fiber is fixed to an elongate instrument or associated structure.

Referring back to FIGS. 11-12 a variation of a partial fiber length registration fixture 156 providing for partial fiber length registration to register a shape sensing fiber to a catheter is shown. The registration fixture 156 is in the form of a vertical plate (e.g., a sharkfin) that is mountable on a center axis of the splayer 153. A groove 157 or track may be cut into the plate. The groove 157 may receive the shape sensing fiber 152, such that at least a portion of the fiber 152 sits inside the groove 157. A fiber 152 may include a service loop 158 which allows the length of the fiber 152 within an elongate instrument to increase or decrease with the bending of the catheter 151. The service loop 158 may be positioned within the groove 157 and a proximal section or origin of the fiber 152 may be fixed to fixture 156. The service loop 158 can help maintain accuracy of shape sensing through the fiber. In one variation, the service loop 158 may maintain less than about a 15 mm radius of curvature. The fiber may optionally have about a 2 cm straight section at its proximal end to allow shape algorithms to initialize.

Figure 14A:
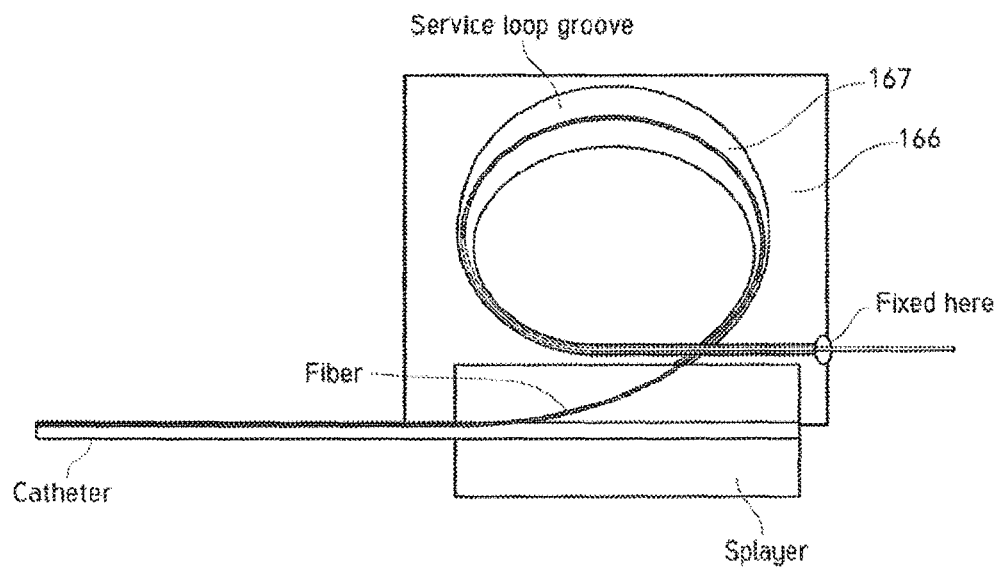
FIG. 14A-14B show variations of registration fixtures for performing registration.
Figure 14B:
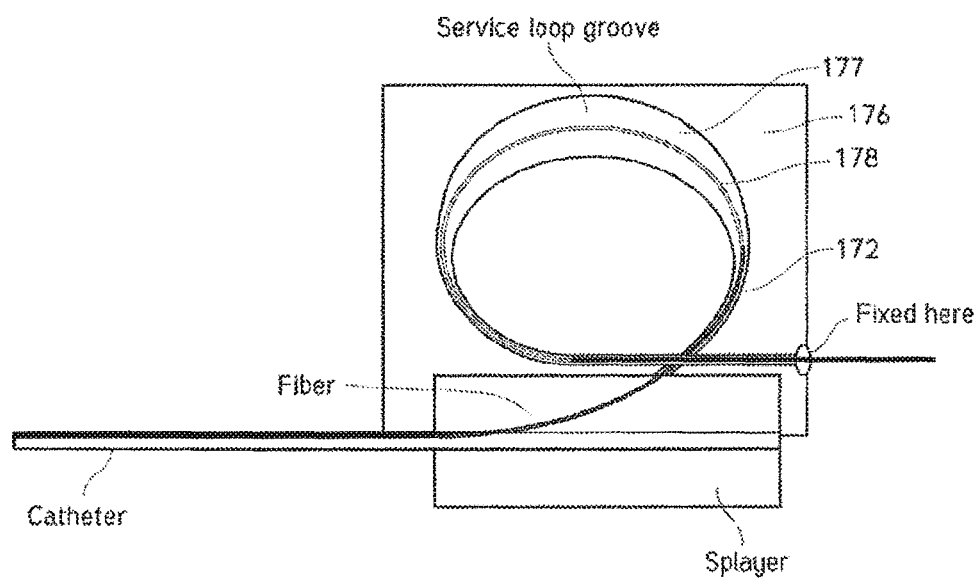

FIG. 14A-14B show two alternative variations of partial fiber length registration fixture 166 structures including a known 2D shape having a 90 degree circle plus a straight section. The tolerance of the grooves 157 or tracks in the fixture 166 may be about 250 microns because an angular error of about 0.05 degrees may lead to a 1 mm error on a 1 m straight length. Tolerances may be relaxed if angles are corrected for a known plane and/or a known heading.

In the partial fiber length registration fixture 176 shown in FIG. 14B, various points along the service loop 178 of the fiber 172 may be used to find two Euler angles to align the fiber 172 to a particular plane. This would reduce the tolerances to having a level plane (within about 200 microns) and provide a shallow track or groove 177 that holds the fiber 172. A straight section along the fiber 172 may be used to correct heading. The straight section may have a pitch tolerance of about 200 microns to reduce mechanical alignment error.

In certain variations, successive information further down the fiber shape, e.g., distally, may be used to correct for heading error, e.g., in situations where the reference or structure is readjusted to be the shaft of a catheter. This type of an adjustment would allow a comparison of the fiber shape to a catheter model. Optionally, the straight section of the hypotube near the proximal end of a catheter may be used to correct the heading from a splayer, e.g., where there is excessive error from the service loop or if the catheter becomes non-orthogonal to the splayer. Readjustments for the origin of the catheter shaft, based upon known fiber lengths in the splayer, may be made.

Registration structures or fixtures may take on additional alternative configurations. In one variation, a mechanical structure may be incorporated into a vertical handle or other functional, ergonomic structure on top of or adjacent a splayer. In certain variations, a fiber service loop may travel in plane or out of plane. Registration structures or fixtures may be positioned parallel to a splayer, bringing a fiber out of plane. For example, a plate may be positioned above or below a splayer and pulleys. Where a registration plate is located below the pulleys, the fiber may extend easily in plane with the service loop, e.g., where the fiber is placed in the lower lumen of a catheter. An example of an out of plane, horizontal mechanical registration structure or fixture is shown in FIG. 9A. As described supra, a service loop may have a variety of shapes or configurations. A service loop may spiral in a left hand or right hand direction and/or have a configuration similar to a bird's eye or jog shape as shown in FIGS. 10A-10C.

In some variations, in order to register the coordinate system of the fiber with the coordinate system of the catheter, full fiber length registration and/or the partial fiber length registration can be performed using the registration fixtures described in detail above. The method of registration, i.e., whether to use full fiber length registration, partial fiber length registration or both, depends on the mechanical stability of the 6 degrees of freedom at the origin of the fiber. In one variation, where all six degrees of freedom of the fiber origin can be securely fixed with regard to a section of the catheter or associated structure, a full length fiber registration can be performed as described above, e.g., during manufacturing, providing all six degrees of orientation of the catheter. In another variation, where the fiber origin can be partially fixed with less than six degrees of freedom, then both full fiber length and partial fiber length registration can be performed. In another variation, where the fiber origin is floating where no degrees of freedom are fixed, full fiber length registration and/or partial fiber length registration and/or a registration technique, such as known shape registration, can be performed.

Six degrees of freedom of a fiber can be fixed in certain variations where a section of the fiber, e.g., a section located at the proximal end or beginning of the fiber, is fixed or anchored relative to the elongate instrument or to a structure associated with the elongate instrument. Once a fiber is fixed relative to an elongate instrument or to a structure associated with the elongate instrument, the fiber may measure where that fixed point is relative to every other point on the fiber. In order to convert that relative position into an absolute position (e.g., the position of the tip of an elongate instrument) the location of that fixed point may be determined relative to some known reference (e.g., an elongate instrument, splayer, robot, or patient). In one variation, a point on the fiber may be fixed or glued down to something static, such that the fixed point of the fiber does not move. The location of the fixed point is then determined. All six degrees of freedom at the fixed point of the fiber are known, and every other point on the fiber may be measured relative to that fixed point. An anchored or fixed section of a fiber provides a stable starting position and origin for measuring the shape of the fiber, such that a relative measurement of the fiber shape (a measurement of one point on a fiber relative to another point on the fiber) may be converted into an absolute measurement of the elongate instrument shape.

In certain variations, a section of the fiber may be attached or affixed to an anchoring mechanism, where the anchoring mechanism may be glued or otherwise affixed or coupled to or positioned on an elongate instrument or a structure associated with the elongate instrument to fix, position, or anchor the fiber in place. Examples of anchoring mechanisms include but are not limited to a hypotube, tube or block made from silica, quartz, glass or other similar material. The anchoring mechanism may help maintain a section of the fiber in a straight configuration, providing a launch region on the fiber which may allow the start or beginning of the fiber to be located. In certain variations, the launch section of a fiber may be in a straight configuration to initialize a particular algorithm. In other variations, a launch section of a fiber may not be straight but may have one or more curves. The anchoring mechanism may be used to fix or anchor a section of the fiber or the origin of the fiber, preventing the fixed section or origin from moving in any of the six degrees of freedom such that an accurate registration of the fiber may be performed.

In certain variations, a system for measuring a shape of an elongate instrument includes a fiber and an anchoring mechanism where the fiber may be affixed to the anchoring mechanism and the anchoring mechanism may be affixed to the elongate instrument or to a structure associated with the elongate instrument. The anchoring mechanism may be in the form of a block, plate or slide. The anchoring mechanism may be made from silica, glass, quartz or a similar material and include a groove or track in which the fiber may be affixed or glued to bond the fiber to the anchoring mechanism. For example, the block may include a groove or track and the fiber may be affixed to the block within the groove or track. Optionally, the fiber may be affixed or glued to a surface of the block, e.g., where the block does not have a groove. The anchoring mechanism may be made from a material having a similar or identical thermal coefficient to that of the fiber.

In another case, it may be difficult to mechanically fix all six degrees of freedom of the fiber. For instance, the position of the fiber could be fixed well, as can the yaw and pitch by using a thin slot, but since the fiber is so thin, it could roll freely in the track. In a case such as this, less than 6 degrees of freedom can be determined from the fiber origin and from full fiber length registration. Thus, the remaining degrees of freedom can be determined using partial fiber length registration fixtures prior to and possibly during the procedure or during use of the catheter or elongate instrument if the fiber position changes in any degree of freedom. For instance, these other degrees of freedom can be determined by a heading, plane, or known shape in the service loop or splayer as previously described. This scheme can also be used if an error through the service loop or a section of the early shape measurement induces an error in one or more of the degrees of freedom of the origin; a secondary plane, shape, or heading can be used to correct these unknowns or errors in real time.

In alternative variations, the fiber origin may not be mechanically secured so no degrees of freedom can be fixed or determined from the origin of the fiber. In such a case, full fiber length registration, partial fiber length registration and/or one or more features or shapes can be used to determine one or more degrees of freedom. For instance, a plane from the service loop and a heading from the hypotube in the catheter may be used to determine all six degrees of freedom. In another variation, a well machined shape track (tolerance track shape track positioned in the device in a well-toleranced way) may be used to determine all six degrees of freedom of the system.

The above processes for registering a fiber may be used together or in the alternative to determine or measure one or more of the six degrees of freedom of a catheter or other elongate instrument. However, in certain variations, it may be difficult to obtain accurate or precise measurements in certain sections of a fiber, e.g., in the service loop. Thus, while one or more degrees of freedom may be measured based on a point on the fiber that is fixed or glued down, a known shape on the fiber may also be located to provide the remaining degrees of freedom. The known shape may be used to measure or detect one or more degrees of freedom to help correct for one or more errors that may have accumulated when measuring sections of the fiber, such as a service loop, that have tight bends or that may be difficult to measure. The tighter the bends imposed on a fiber are, the more difficult it may be for the fiber to maintain accuracy of its shape measurement. Use of the known shape registration technique in combination with the fixed fiber registration information may improve overall shape measuring accuracy.

In certain variations, a process for registering a fiber may or may not require fixing a point on the fiber. A known shape may be imposed or placed on the fiber and the shape may be recognized in a measurement coming from the fiber. The imposed shape is located in the measurement from the fiber and then lined up or registered with the known mechanical shape, machined to precise tolerances, providing an on the fly registration. The location of the shape in space and/or the orientation of the shape may be known or determined. For example, the shape may be referenced to certain data on a splayer. In certain variations, the shape may be located on a fixture, e.g., plate or slide, where the shape is toleranced tightly and the location of the shape is known relative to another point on the fixture, plate or slide.

The known shape registration technique may be used in combination with fixed fiber registration information obtained according to the fixed fiber registration techniques described above. In other variations, the known shape registration techniques may be used alone to ascertain one or more degrees of freedom or all six degrees of freedom of an elongate instrument by registering a fiber to an elongate instrument.

In another variation, twist or slide of the fiber may be difficult to detect or measure using the fixed fiber technique, so twist or slide may be detected or measured at a different point on the fiber, e.g., on a different plane, using the known shape technique.

In certain variations, the known shape may be placed anywhere in an elongate instrument, catheter or splayer, e.g., a known 2D or 3D shape. The physical structure for maintaining a shape may be located in a position that maintains the fiber shape and allows the shape to be recognized. The shape may be in a position where it is mechanically fixed relative to some other known structure or reference that has a known location. The shape may be structurally integrated into an elongate instrument, catheter, splayer, or fixture referenced to a splayer or robot, an introduction site (e.g., a known jog shape at a stabilizer at an introduction site) or into another component or structure associated with an elongate instrument. The above structures and sites may be used as references. Optionally, the shape may be reliably referenced to a known spot, origin or structure, such as something affixed or glued to a patient or to a physical organ.

The properties or configurations of known shapes used in the known shape registration technique may depend on the particular degrees of freedom to be obtained. For example, a bird's eye, jog, spiral and/or straight line shape in a fiber may be utilized. In certain variations, one or more known shapes (different or similar) may be placed along different lengths or sections of a fiber. The shapes may be used or read to measure or detect one or more degrees of freedom to calibrate out any errors that may have accumulated from measurements taken using the fixed fiber registration technique.

In certain variations, known shapes may be placed in an elongate instrument or other structure associated with the elongate instrument, e.g., by being mechanically placed therein. A lumen of an elongate instrument may be provided with a jog shape or other suitable shape. In certain variations, a straight hypotube holding a proximal section of a fiber may provide a known shape. The hypotube shape is straight and recognizable and its location is also known. The stiffness of the hypotube may be altered to make it stiffer and more accurate. A straight line shape may be placed in various sections of an elongate instrument or fiber and utilized as a known shape. A known shape may be straight, curved or any other possible configuration. A known recognition shape may be placed anywhere along the length of a fiber, elongate instrument, catheter, plate, splayer or other structure. Any known shape may allow for the measurement or ascertaining of one or more degrees of freedom.

Information about the shapes in a fiber in a fixture, splayer, or other structure located anywhere along the fiber may be used for performing registration or alignment. In certain variations, the shapes may be used for performing registration or alignment depending on the tolerances of the manufacturing process. In certain variations, the shapes may be used to confirm or reacquire registration or alignment information or to reacquire or check one or more degrees of freedom.

In certain variations, various registration techniques are provided that allow for all six degrees of freedom of a coordinate frame to be solved or ascertained with respect to another coordinate frame. In one variation, a fiber origin may be glued or otherwise affixed to an elongate instrument or structure associated with an elongate instrument and full fiber length registration or calibration may be utilized to ascertain all six degrees of freedom of an elongate instrument by registering the coordinate system of the fiber to the coordinate system of the elongate instrument.

Figure 18:
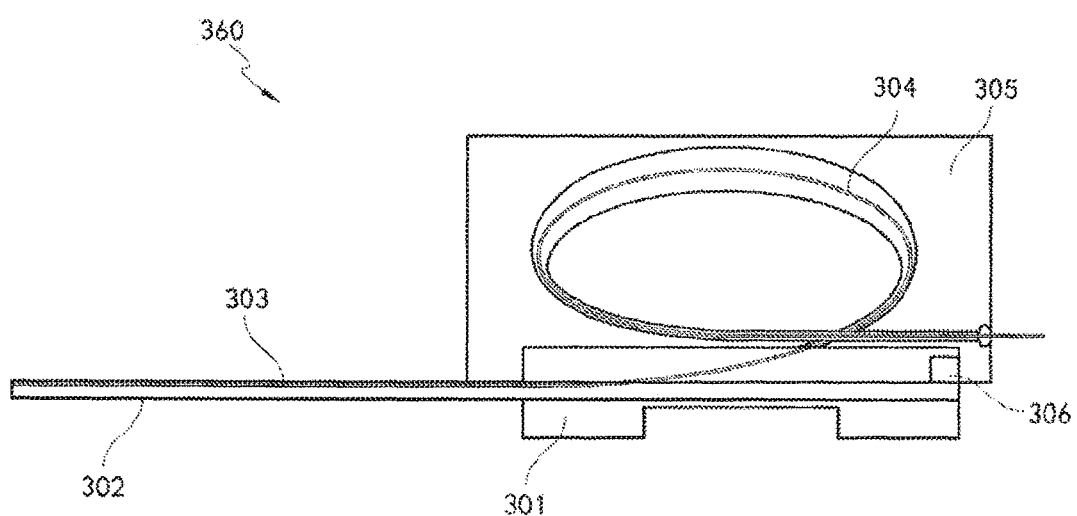
FIG. 18 shows a variation of a manually steerable elongate instrument having an integrated fiber.

Any of the various devices, systems or methods described herein for integrating or registering a fiber in or to an elongate instrument or other structure may apply to, be performed on or be incorporated in any manually and/or robotically controlled or steerable elongate instruments or catheters. FIG. 18 shows on example of a manually operated elongate instrument or catheter assembly 300 having a base 301 or handle, a control knob 306, a catheter 302, an integrated fiber 303, and a service loop 304 held in a registration fixture 305, which may be coupled to the base 301, the catheter 302 or handle or any other structure fixed or coupled to the catheter.

Figure 19:
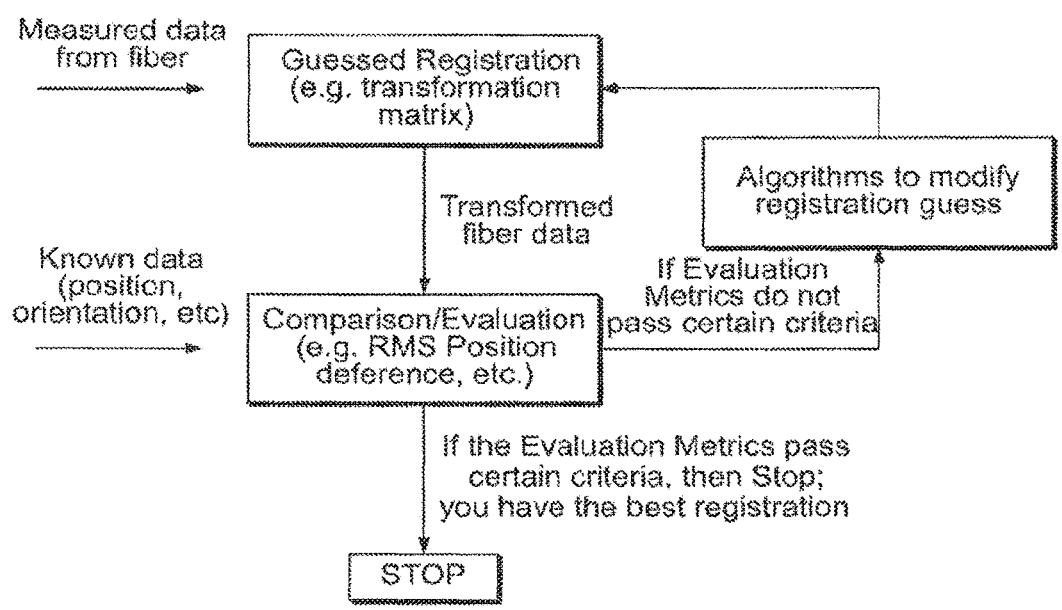
FIG. 19 shows a flow chart showing one variation of a method for registering a fiber to an elongate instrument or other structure.

FIG. 19 shows a flow chart showing one example of a method for registering a fiber to an elongate instrument or other structure. Registration may result in producing a transformation matrix. Translations or rotations in any of the degrees of freedom may also constitute registration. The registration process involves matching two subsets of points or orientations between a "known" data set (e.g., from a fixture, images, etc.) and a "measured" data set (e.g., a data set obtained from the fiber or sensor of interest). The registration may be found iteratively. A guess of the registration can be made and applied to the measured data. This transformed data is then compared to the known data, for instance through RMS positional error or any other desired metric. If this metric is determined to show that the known and transformed measured data have low error, then the cycle ends, and the registration has been found. If the metric shows that the known and transformed measured data do not adequately line up with each other, then the metric is used to produce another guess and the cycle may be repeated over again.

Figure 20:
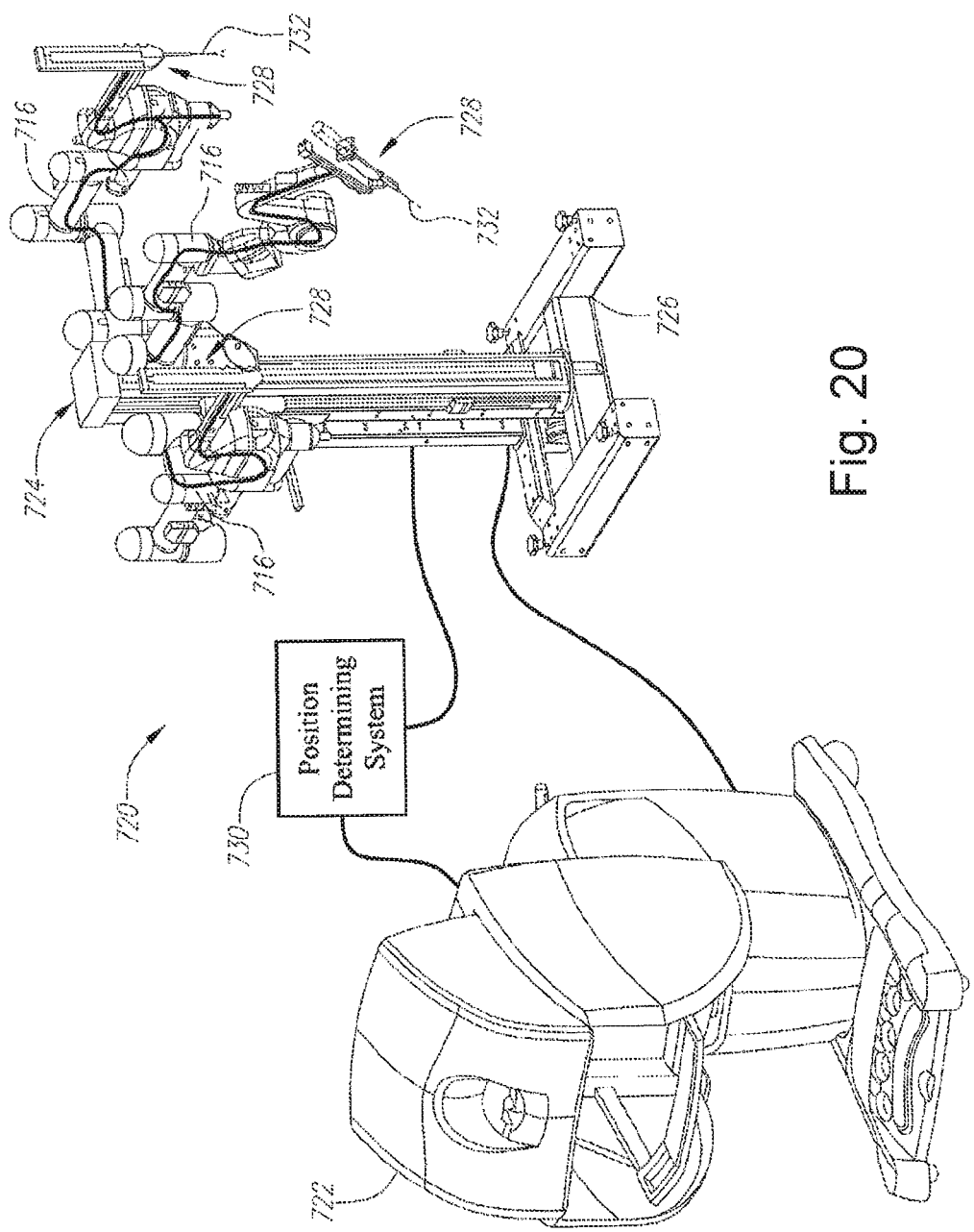
FIG. 20 shows a perspective view of a surgical system with a shape sensing system mounted therein.

FIG. 20 is the same as FIG. 25A of U.S. patent application Ser. No. 12/837,440, now U.S. Pat. No. 8,780,339, which was previously incorporated by reference. Referring to FIG. 20, a position determining system 730 is depicted operatively coupled to each of the fibers 716. The position determining system 730, generally comprising an optical radiation emitter and detector, and a computing system to analyze detected optical radiation, may be operatively coupled to each of the fibers 716 via the cart 726. The position determining system 730 is configured to analyze data from the fibers 716 as the arms 728 are maneuvered and determine changes in elongation of the fibers 716. Some systems, such as those available from Luna Innovations, Inc., may be configured to utilize sensed deflection data to determine the spatial positioning or shape of a particular fiber or bundle of fibers. Although it is referred to herein as a "position determining system," such system may also analyze, calculate and/or determine other information using the data from the fibers, including without limitation, stress, strain or elongation, forces, and/or temperature. The positioning determining system 730 is also operatively coupled to the operator control station 722 or control system of the instrument system, such that position information as determined by the position determining system 730 may be relayed to the operator control system 722 to assist in navigation and control of the instrument system. In this illustration, the surgical workstation 724 carries three robotically controlled arms 728, and the movement of the arms 728 is remotely controllable from the control station 722. In other variations, the cart 726 may carry a varying number of arms 728 (i.e., one or more arms; or two or four arms) depending on the particular configuration.

In certain variations, a housing, e.g., a splayer or instrument driver, may be coupled to a proximal portion of any of the elongate instruments or devices described herein. The housing may include an interface for receiving an actuating force and transferring the actuating force to the elongate instrument to articulate a distal portion of an elongate instrument. A shape sensing fiber may be integrated in the elongate instrument and may include a first portion positioned within the lumen of the elongate instrument. Optionally, the fiber may also include a second portion positioned within the housing, where the second portion can include a service loop which allows for sliding of the fiber within the lumen of the elongate instrument when the distal portion of the elongate instrument is articulated.

In any of the variations described herein, the particular shape that may be utilized in a fiber for registration purposes may depend on the a variety of factors, such as, the amount of error accrued going through that shape, how much slack is needed in a service loop, and any spatial restriction imposed by the particular system in which the fiber is being utilized. For example, in a robotic catheter system, space may be restricted due to the positioning of a guide wire manipulator or other component of the system. Examples of fiber shapes have been described supra, and include but are not limited to a bird's eye, jog or spiral shape or any other shape.

In certain variations, whether using a full or partial length registration fixture or any other known shape, the shape may include curves with large bends and a minimum number of turns to help minimize error. A shape may also be configured in a manner that allows the data to have long lever arms, e.g., a shape may cover the largest volume possible as permitted by the space available, to achieve an optimal registration. A shape may be configured in a manner, e.g., that balances a desired shape that minimizes error while occupying an adequate amount of space on a registration fixture (e.g., a shark fin or plate). In one variation, a shape may include a u-turn having a large bend radius.

As described supra, in certain variations a region of the fiber, e.g., the proximal region or origin of a fiber may be configured to facilitate registration of a fiber to an elongate instrument. In one variation, a portion of a fiber may be fixed in one to six degrees of freedom by fixing or gluing the fiber to a block, where the block is in a fixed location relative to an elongate instrument or splayer.

In another variation, a fiber may positioned or configured into a known shape, plane, line, vector, orientation or other position within a registration fixture that is attached to or fixed in a known location relative to an elongate instrument, splayer or other structure. One to six degrees of freedom of the fiber may be deduced based on the known shape or other orientation. Optionally, an unknown arbitrary shape may be utilized from which zero degrees of freedom of the fiber may be deduced.

Once the proximal or other region of the fiber is configured in any manner described herein, one or more or a combination of registration techniques may be utilized to obtain one to six degrees of freedom of the fiber relative to the elongate instrument, a splayer, a housing, a catheter, a registration fixture or other structure of interest. One to six degrees of freedom of the fiber may be measured or ascertained relative to an elongate instrument, e.g., via a structure or fixture whose location relative to an elongate instrument is known. In one variation, a fiber may be fixed in six degrees of freedom such that all six degrees of freedom of the fiber can be deduced in a fixture which may hold the entire or substantially the entire length of the fiber. The fixture may or may not be attached to the elongate instrument. The resulting registration or calibration may not change where the fiber is fixed or glued in place. If less than six degrees of freedom of the fiber are obtained, the remaining degrees of freedom may be deduced dynamically to register the fiber to the elongate instrument dynamically, during use of the elongate instrument.

In another variation, where the fiber is in a known shape or is configured in a known plane or other orientation in a fixture, (e.g., a fixture attached to the elongate instrument), one to six degrees of freedom may be deduced during use of the elongate instrument. A fiber positioned in a known 2D shape may be utilized to determine one to six degrees of freedom. A fiber configured in a known plane may be utilized to determine at least one degree of freedom.

In other variations, other features may be utilized to register a fiber to an elongate instrument or other structure during use of that instrument or other device or structure. For example, various shapes in an anatomy coupled with a CT image or 3D model; a known shape in an introducer through which the elongate instrument passes; the known location of a leader and a sheath splayer; and/or other features may be utilized to register a fiber to a desired instrument or other structure.

In any of the variations described herein, the shape of the fiber or elongate instrument may be obtained by collecting data along the fiber from the proximal end to the distal end of the fiber. In certain variations, registration data (e.g., full length or partial length) may be stored on the splayer EEPROM, on a USB, a server, or other portable memory device, from which the data may be accessed.

In another variation, a fiber may be placed or configured in a known shape in various locations for obtaining registration data. For example, the fiber may be placed in a known shape between the registration fixture and the Lune box or controller. In another example, a known shape may be placed between the service loop or registration fixture and the distal end of the fiber, e.g., at the introducer site. In another example, a known shape may be placed on a table or patient bed which may allow the fiber to be registered to the bed to minimize or avoid movement from an RCM or setup joint.

In certain variations, a system may include an elongate instrument having a proximal end, a distal end and at least one lumen defined therein. The system may also include a shape sensing fiber, where at least a first portion of the fiber is positioned in the lumen of the elongate instrument. A second portion of the fiber may be fixed or otherwise attached in a known location or position relative to the elongate instrument or to another structure such that the coordinate system of the fiber can be matched to the coordinate system of the elongate instrument to register the fiber to the elongate instrument. In certain variations, registration may allow the shape of an elongate instrument to be detected or determined, e.g., based on the shape of the fiber.

The second portion of the fiber may be fixed such that one or more degrees of freedom of the fixed portion the fiber may be measured or ascertained relative to the elongate instrument or other structure. Optionally, the second portion of the fiber may have a known shape.

In certain variations, the system may include a registration fixture. The second portion of the fiber may be fixed in a known location on the registration fixture and the registration fixture may be in a known location relative to the elongate instrument. The registration fixture may have grooves or slots for holding at least a portion of the fiber and/or at least a portion of the elongate instrument in a known shape, orientation or position.

In certain variations, the second portion of the fiber may be configured in a known position or orientation in a registration fixture such that data can be collected regarding the position or orientation of at least a partial length of the second portion of the fiber. The collected data may be used to calculate a transform between the coordinate system of the fiber and the coordinate system of the elongate instrument or other structure, to perform registration.

In certain variations, a housing may be coupled to a proximal portion of the elongate instrument. The housing may include an interface for receiving an actuating force and transferring the actuating force to the elongate instrument to articulate a distal portion of the elongated instrument. The registration fixture may be positioned on or in the housing. A portion of the fiber may be positioned within the housing, where the portion of fiber includes a service loop. The service loop may allow for sliding or displacing of the fiber within the lumen of the elongate instrument when the distal portion of the elongate instrument is articulated.

In certain variations, the system may be removably coupled to an instrument driver and a controller which controls actuation of the elongate instrument. Actuation motion may be transferred from the controller to the system via the instrument driver to articulate the distal end of the elongate instrument in at least one degree of freedom. Any variation of the system or assemblies described herein may be disposable.

In certain variations, a method for registering a fiber to an elongate instrument and/or detecting the shape of an elongate instrument may include one or more of the following steps. An assembly having an elongate instrument and a shape sensing fiber may be operated. The elongate instrument may have a proximal end, a distal end and at least one lumen defined therein, where least a first portion of the fiber may be positioned in the lumen of the elongate instrument. At least a second portion of the fiber may be fixed in a known location or position relative to the elongate instrument or to another structure. A position of the fixed portion of the fiber may be measured or ascertained relative to the elongate instrument to match the coordinate system of the fiber with the coordinate system of the elongate instrument to register the fiber to the elongate instrument.

In certain variations, one or more degrees of freedom of the fixed portion the fiber may be measured or ascertained relative to the elongate instrument. Optionally, one or more degrees of freedom of a portion of the fiber configured in a known shape, plane or other orientation may be measured or ascertained relative to the elongate instrument. Measuring or ascertaining or matching of the coordinate systems may be performed while the elongate instrument is positioned within an anatomical region. The registration may allow the shape of the elongate instrument to be detected.

In certain variations, saved registration data regarding registration between the coordinate system of the fiber and the coordinate system of the elongate instrument may be accessed from a memory component to determine the shape of the elongate instrument.

In certain variations, the assembly may be removably coupled to an instrument driver and a controller which controls actuation of the elongate instrument, wherein actuation motion is transferred from the controller to the elongate instrument via the instrument driver to articulate the distal end of the elongate instrument in at least one degree of freedom.

In certain variations, the assembly may include a registration fixture. The second portion of the fiber may be fixed in a known location on the registration fixture and the registration fixture may be in a known location relative to the elongate instrument. One or more degrees of freedom of the second portion of the fiber may be measured or ascertained relative to the registration fixture and the elongate instrument. A registration fixture may have grooves for holding at least a portion of the fiber in a known shape, orientation or position.

In certain variations, data may be collected regarding the position or orientation of at least a partial length of the fixed portion of the fiber configured in a known position or orientation in a registration fixture. The collected data may be used to calculate a transform between the coordinate system of the fiber and the coordinate system of the elongate instrument or other structure.

In certain variations, a system may include an elongate instrument having a proximal end, a distal end and at least one lumen defined therein. The system may also include a shape sensing fiber, wherein at least a first portion of the fiber is positioned in the lumen of the elongate instrument. A second portion of the fiber may be configured in a known shape, plane or other orientation relative to the elongate instrument or to another structure such that the coordinate system of the fiber may be matched to the coordinate system of the elongate instrument to register the fiber to the elongate instrument.

In certain variations, one or more degrees of freedom of the second portion of the fiber may be measured or ascertained relative to the elongate instrument. In certain variations, the second portion of the fiber may be positioned between a distal end of the fiber and a service loop located at a proximal end of the fiber. The second portion of the fiber may be held within a registration fixture associated with the elongate instrument. In one variation, the second portion of the fiber may have a u-turn configuration with a large bend radius to minimize measurement error and fit within a registration fixture associated with the elongate instrument. In certain variations, the second portion of the fiber may be configured in a known position or orientation in a registration fixture such that data can be collected regarding the position or orientation of at least a partial length of the second portion of the fiber. The collected data may be used to calculate a transform between the coordinate system of the fiber and the coordinate system of the elongate instrument or other structure.

In certain variations, a method of detecting the shape of an elongate instrument may include one or more of the following steps. Operating an assembly having an elongate instrument and a shape sensing fiber, where the elongate instrument may have a proximal end, a distal end and at least one lumen defined therein may be performed. At least a first portion of the fiber may be positioned in the lumen of the elongate instrument and at least a second portion of the fiber may be configured in a known shape, plane or other orientation. A position of the second portion of the fiber may be measured or ascertained relative to the elongate instrument to match the coordinate system of the fiber with the coordinate system of the elongate instrument to register the fiber to the elongate instrument.

In certain variations, one or more degrees of freedom of the second portion of the fiber may be measured or ascertained relative to the elongate instrument. In certain variations, the second portion of the fiber may be positioned between a distal end of the fiber and a service loop located at a proximal end of the fiber. In other variations, a second portion of the fiber may be positioned on a portion of the fiber fixed to an operating table or bed.

In other variations, a second portion of the fiber may be held within a registration fixture associated with the elongate instrument. Optionally, data may be collected regarding the position or orientation of the second portion of the fiber configured in a known shape, plane or other orientation in a registration fixture. The collected data may be used to calculate a transform between the coordinate system of the fiber and the coordinate system of the elongate instrument or other structure.

In certain variations, a method for detecting the shape of an elongate instrument may include one or more of the following steps. Operating an assembly having an elongate instrument and a shape sensing fiber may be performed. The elongate instrument may have a proximal end, a distal end and at least one lumen defined therein. At least a first portion of the fiber may be positioned in the lumen of the elongate instrument and at least a second portion of the fiber may be fixed in a known location relative to the elongate instrument or to another structure. Saved registration data may be accessed regarding registration between the coordinate system of the fiber and the coordinate system of the elongate instrument from a memory component to determine the shape of the elongate instrument. Optionally, the structure may be a registration fixture which may be positioned in a known location relative to the elongate instrument.

In certain variations, one or more degrees of freedom of the fixed portion the fiber may be measured or ascertained relative to the elongate instrument. This step may be performed while the elongate instrument is positioned within an anatomical region. In certain variations, one or more degrees of freedom of a portion of the fiber configured in a known shape, plane or other orientation may be measured or ascertained relative to the elongate instrument.

In certain variations, an assembly may be removably coupled to an instrument driver and a controller which controls actuation of the elongate instrument, wherein actuation motion is transferred from a controller to the elongate instrument via the instrument driver to articulate the distal end of the elongate instrument in at least one degree of freedom.

In certain variations, a system may include an elongate instrument having a proximal end, a distal end and one or more lumens defined therein. The system may include a shape sensing fiber, where at least a portion of the fiber may be positioned within the lumen of the elongate instrument. The shape sensing fiber may have a service loop which allows for sliding or displacing of the fiber within the lumen of the elongate instrument when a distal portion of the elongate instrument is articulated. The system may also include a coil positioned within the lumen, and surrounding or at least partially or substantially surrounding the fiber. The coil may be slideable within the lumen and the coil may maintain the lumen in an open state during articulation of the elongate instrument.

In certain variations, the coil may be positioned in a distal section of first lumen. In certain variations, a fiber may be free floating within the coil.

In certain variations, a proximal section of the first lumen may be incorporated into a braid in the elongate instrument. The braid may optionally be configured to wind around the proximal section of the lumen as well as a working lumen and control wire lumen of the elongate instrument, in a diamond braid pattern.

In certain variations, the elongate instrument may have a tip which is reinforced to support or protect at least a portion of a fiber termination positioned therein. The elongate instrument tip may include a control ring and the fiber may extend through or along the control ring.

In certain variations, a system may include an elongate instrument having a proximal end, a distal end and at least one lumen defined therein. The system may include a housing coupled to a proximal portion of the elongate instrument, where the housing includes an interface for receiving an actuating force and transferring the actuating force to the elongate instrument to articulate a distal portion of the elongated instrument. The system may also include a shape sensing fiber. At least a first portion of the fiber may be positioned within the lumen of the elongate instrument, and a second portion of the fiber may be positioned within the housing. The second portion of the fiber may include a service loop which allows for sliding or displacing of the fiber within the lumen of the elongate instrument when the distal portion of the elongate instrument is articulated.

In certain variations, the interface may be configured to couple to an actuator. The actuating force may be delivered via robotic control in a robotically controlled or steerable elongate instrument system. In certain variations, the interface may include a knob for a user to manually deliver such actuation force.

In certain variations, at least a portion of the sensing fiber may be fixed relative to the elongate instrument or to a structure associated with the elongate instrument. At least a portion of the fiber positioned within the lumen of the elongate instrument may be decoupled or free floating relative to the lumen of the elongate instrument.

In certain variations, the housing may include a registration fixture. At least a portion of the service loop may be held within a groove or track of the registration fixture. The service loop may be configured to slide in a single plane within the registration fixture. The service loop may have a shape configured to fit substantially within the registration fixture.

In certain variations, the registration fixture may include a pocket positioned thereon. The fiber may include an anchoring mechanism affixed to a proximal portion of the fiber, wherein the anchoring mechanism may be configured to slide within the pocket in no more than one degree of freedom or in one or more degrees of freedom. The fiber may include an anchoring mechanism affixed to a proximal portion of the fiber, wherein the anchoring mechanism may be affixed within the pocket to fix a known fiber length. Optionally, the anchoring mechanism may include a silica block or straight tube.

In certain variations, a method of actuating an elongate instrument may include one or more of the following steps. A system may be operatively coupled a to a controller. The system may include an elongate instrument; a housing coupled to a proximal portion of the elongate instrument, where the housing comprises an interface for receiving an actuating force and transferring the actuating force to the elongate instrument to articulate a distal portion of the elongate instrument; and a shape sensing fiber. The elongate instrument may have a proximal end, a distal end and at least one lumen defined therein. At least a first portion of the fiber may be positioned within the lumen of the elongate instrument, and a second portion of the fiber may be positioned within the housing. The second portion of the fiber may include a service loop. Actuating motion may be transferred from the controller to the system to articulate the distal portion of the elongate instrument in at least one degree of freedom, where the service loop allows the fiber to slide or be displaced within the lumen of the elongate instrument when the distal portion of the elongate instrument is articulated, thereby controlling the amount of strain the fiber is subjected to and maintaining shape sensing properties of the fiber.

In certain variations, the housing may include a registration fixture. At least a portion of the service loop may be held within a groove or track of the registration fixture. The service loop may be configured to slide in a single plane within the registration fixture. The service loop may have a shape configured to fit substantially within the registration fixture. In certain variations, at least a portion of the fiber positioned within the lumen of the elongate instrument may be decoupled or free floating relative to the lumen of the elongate instrument.

In certain variations, a system may include an elongate instrument having a proximal end, a distal end and at least one lumen defined therein. A housing may be coupled to a proximal portion of the elongate instrument, wherein the housing includes an interface for receiving an actuating force and transferring the actuating force to the elongate instrument to articulate a distal portion of the elongate instrument. The system also includes a shape sensing fiber. At least a first portion of the fiber may be positioned in the lumen of the elongate instrument. At least a second portion of the fiber may be positioned in the housing such that the coordinate system of the fiber can be matched to the coordinate system of the elongate instrument to register the fiber to the elongate instrument. The second portion of the fiber may include a service loop which allows for sliding or displacing of the fiber within the lumen of the elongate instrument when the distal portion of the elongate instrument is articulated.

In certain variations, at least a portion of the second portion of the fiber may be fixed such that one or more degrees of freedom of the fixed portion the fiber may be measured or ascertained relative to the elongate instrument. In certain variations, at least a portion of the second portion of the fiber may be configured in a known shape, plane or other orientation such that one or more degrees of freedom of the portion of the fiber may be measured or ascertained relative to the elongate instrument. In certain variations, at least a portion of the fiber positioned within the lumen of the elongate instrument may be decoupled or free floating relative to the lumen of the elongate instrument.

In certain variations, the system may be removably coupled to an instrument driver and a controller which controls actuation of the elongate instrument, wherein actuation motion is transferred from the controller to the system via the instrument driver to articulate the distal portion of the elongate instrument in at least one degree of freedom. Any of the systems described herein may be disposable.

In certain variations, the housing may include a registration fixture. Optionally, a fixed portion of the fiber and the service loop may be positioned on a single registration fixture. The registration fixture may include grooves for holding at least a portion of the service loop. A service loop may be configured to slide in a single plane within the registration fixture. In certain variations, a registration fixture may include grooves for holding at least a portion of the fiber or at least a portion of the elongate instrument in a known shape, orientation or position.

In certain variations, a method of actuating an elongate instrument may include one or more of the following steps. An assembly may be operatively coupled to a controller. The assembly may include an elongate instrument; a housing coupled to a proximal portion of the elongate instrument, wherein the housing comprises an interface for receiving an actuating force and transferring the actuating force to the elongate instrument to articulate a distal portion of the elongate instrument; and a shape sensing fiber. At least a first portion of the fiber may be positioned in the lumen of the elongate instrument. At least a second portion of the fiber may be positioned in the housing such that the coordinate system of the fiber can be matched to the coordinate system of the elongate instrument to register the fiber to the elongate instrument. The second portion of the fiber may include a service loop. Actuation motion may be transferred from the controller to the assembly to articulate the distal end of the elongate instrument in at least one degree of freedom. The service loop may allow the fiber to slide or displace within the lumen of the elongate instrument when the distal portion of the elongate instrument is articulated, thereby controlling the amount of strain the fiber is subjected to. Saved registration data regarding registration between the coordinate system of the fiber and the coordinate system of the elongate instrument may be accessed from a memory component to determine the shape of the elongate instrument.

In certain variations, at least a portion of the second portion of the fiber may be fixed such that one or more degrees of freedom of the fixed portion the fiber may be measured or ascertained relative to the elongate instrument. In certain variations, at least a portion of the second portion of the fiber may be configured in a known shape, plane or other orientation such that one or more degrees of freedom of the portion of the fiber may be measured or ascertained relative to the elongate instrument. In certain variations, at least a portion of the fiber positioned within the lumen of the elongate instrument may be decoupled or free floating relative to the lumen of the elongate instrument.

In certain variations, a system may be removably coupled to an instrument driver and a controller which controls actuation of the elongate instrument, wherein actuation motion is transferred from the controller to the system via the instrument driver to articulate the distal portion of the elongate instrument in at least one degree of freedom. In certain variations, the housing may include a registration fixture. Optionally, the service loop may have a shape configured to fit substantially within a registration fixture.

In any of the variations described herein, an elongate instrument may include one or more lumens. For example, the elongate instrument may include a primary lumen and one or more secondary lumens.

Each of the individual variations described and illustrated herein has discrete components and features which may be readily separated from or combined with the features of any of the other variations. Modifications may be made to adapt a particular situation, material, composition of matter, process, process act(s) or step(s) to the objective(s), spirit or scope of the present invention.

Methods recited herein may be carried out in any order of the recited events which is logically possible, as well as the recited order of events. Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

This disclosure is not intended to be limited to the scope of the particular forms set forth, but is intended to cover alternatives, modifications, and equivalents of the variations described herein. Further, the scope of the disclosure fully encompasses other variations that may become obvious to those skilled in the art in view of this disclosure. The scope of the present invention is limited only by the appended claims.

What is claimed is:

1. A system comprising:
    an elongate instrument comprising: an elongate body having a proximal end, a distal end, and a lumen extending from the proximal end to the distal end, a splayer coupled to the proximal end of the elongate body, and one or more control wires extending through the elongate body and coupled to the distal end of the elongate body with a control ring, wherein the one or more control wires are configured to control movement of the distal end of the elongate body;
    a shape-sensing fiber, wherein at least a first portion of the fiber, including a first end, is positioned within the lumen of the elongate body, wherein at least a second end of the fiber is fixed to an anchor slide, wherein the anchor slide fixes the second end of the fiber to a reference structure in one or more degrees of freedom at a fixed point separate from and proximal to the elongate instrument, wherein the reference structure facilitates the calibration of the fiber to a known structure of the reference structure, and wherein every location on the fiber is measurable relative to the fixed point to determine a relative position and shape of the fiber, a distal end of the shape-sensing fiber coupled to a termination having light absorptive properties, wherein the fiber and the termination are coupled to each other within the control ring;
    at least one computer-readable memory having stored thereon executable instructions; and
    one or more processors in communication with the at least one computer-readable memory and configured to execute the instructions to cause the system to at least:
        register the fiber during use of the elongate instrument by comparing the shape of the fiber to a model,
    wherein the fiber is fixed in six degrees of freedom at the fixed point, with the position of the fiber relative to the elongate body known in all six degrees of freedom at the fixed point, such that an absolute measurement of position, orientation, and shape of the elongate body is quantifiable from the relative position and shape of the fiber.

2. The system of claim 1, wherein the reference structure is a robotic arm, and wherein the elongate instrument is attached to and robotically steerable by the robotic arm.

3. The system of claim 1, wherein the reference structure is a patient bed or a patient table.

4. The system of claim 1, wherein the reference structure is on a patient.

5. The system of claim 1, wherein the elongate instrument is selected from the group comprising a catheter, an endoscope and a bronchoscope.

6. The system of claim 1, wherein the first end of the fiber is fixed to the distal end of the elongate body.

7. The system of claim 1, wherein at least a portion of the fiber positioned within the lumen of the elongate body is decoupled or free floating relative to the lumen.

8. The system of claim 1, wherein the second end of the fiber is fixed in a straight configuration.

9. The system of claim 1, wherein the second end of the fiber is affixed to the fixed point with glue.

10. The system of claim 1, wherein the second end of the fiber is affixed to the fixed point by an anchoring mechanism selected from the group consisting of a hypotube, a tube, a block, a plate and a groove.

11. The system of claim 1, wherein the system is configured to match a coordinate system of the fiber to a coordinate system of the elongate body instrument at the fixed point.

12. The system of claim 1, further comprising:
    a controller operatively coupled to the elongate instrument and configured to control actuation of the elongate instrument; and
    an instrument driver and an interface for generating an actuating force and transferring the actuating force to the elongate instrument to articulate a distal portion of the elongate instrument in at least one degree of freedom.

13. The system of claim 12, wherein the elongate instrument is removably coupled to the instrument driver.

14. The system of claim 1, wherein the position of the fiber relative to the elongate body is determined during a calibration process performed during manufacturing.

15. The system of claim 14, wherein the calibration process comprises:
    collecting calibration data from the elongate instrument and the fiber; and
    using the calibration data to calculate a transform between the coordinate system of the fiber and the coordinate system of the elongate body.

16. The system of claim 15, wherein the calibration data is stored for the elongate body and retrievable during use.

17. The system of claim 16, further comprising a computing device and memory with the calibration data stored thereon, the computing device configured to apply the calibration data to transform the measured location, position, and shape of the fiber and determine the absolute measurement of position, shape, and orientation of the elongate body.

18. The system of claim 17, wherein the orientation of the elongate body is used to enable instinctive driving of the elongate instrument.

19. The system of claim 1, wherein the fiber is positioned along a neutral bending axis of the elongate instrument.

20. A system comprising:
    an elongate instrument comprising: an elongate body having a proximal end, a distal end, and a lumen extending from the proximal end to the distal end, a splayer coupled to the proximal end of the elongate body, and one or more control wires extending through the elongate body and coupled to the distal end of the elongate body with a control ring, wherein the one or more control wires are configured to control movement of the distal end of the elongate body;
    a shape-sensing fiber, wherein at least a first portion of the fiber, including a first end, is positioned within the lumen of the elongate body, wherein at least a second end of the fiber is fixed to an anchor slide, wherein the anchor slide fixes the second end of the fiber to a reference structure in one or more degrees of freedom at a fixed point separate from and proximal to the elongate instrument, a distal end of the shape-sensing fiber coupled to a termination having light absorptive properties, wherein the fiber and the termination are coupled to each other within the control ring, wherein the reference structure facilitates the calibration of the fiber to a known structure of the reference structure;

at least one computer-readable memory having stored thereon executable instructions; and one or more processors in communication with the at least one computer-readable memory and configured to execute the instructions to cause the system to at least:
register the fiber during use of the elongate instrument based on the shape of the fiber and a model of the known structure of the reference structure.

21. The system of claim 1 wherein the termination is positioned within the lumen of the elongate body.

22. The system of claim 1 wherein the termination is made from glass.

23. The system of claim 1 wherein the termination is spliced to the distal end of the shape sensing fiber.

\* \* \* \* \*